US009518261B2

(12) United States Patent
Freier et al.

(10) Patent No.: US 9,518,261 B2
(45) Date of Patent: Dec. 13, 2016

(54) MODULATION OF ENHANCER RNA MEDIATED GENE EXPRESSION

(71) Applicants: Ionis Pharmaceuticals, Inc., Carlsbad, CA (US); Christopher K. Glass, San Diego, CA (US); Michael G. Rosenfeld, San Diego, CA (US); Wenbo Li, San Diego, CA (US); Michael T. Lam, La Jolla, CA (US)

(72) Inventors: Susan M. Freier, San Diego, CA (US); Christopher K. Glass, San Diego, CA (US); Michael G. Rosenfeld, San Diego, CA (US); Wenbo Li, San Diego, CA (US); Michael T. Lam, La Jolla, CA (US)

(73) Assignees: Ionis Pharmaceuticals, Inc., Carlsbad, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 14/403,103

(22) PCT Filed: May 22, 2013

(86) PCT No.: PCT/US2013/042163
§ 371 (c)(1),
(2) Date: Nov. 21, 2014

(87) PCT Pub. No.: WO2013/177248
PCT Pub. Date: Nov. 28, 2013

(65) Prior Publication Data
US 2015/0176005 A1 Jun. 25, 2015

Related U.S. Application Data

(60) Provisional application No. 61/650,426, filed on May 22, 2012.

(51) Int. Cl.
C12N 15/11 (2006.01)
C07H 21/04 (2006.01)
C12Q 1/68 (2006.01)
C12N 15/113 (2010.01)
C12N 15/85 (2006.01)

(52) U.S. Cl.
CPC ............ *C12N 15/113* (2013.01); *C12N 15/85* (2013.01); *C12N 2310/11* (2013.01); *C12N 2310/113* (2013.01); *C12N 2310/315* (2013.01); *C12N 2310/3231* (2013.01); *C12N 2310/3341* (2013.01); *C12N 2310/341* (2013.01)

(58) Field of Classification Search
None
See application file for complete search history.

(56) References Cited

U.S. PATENT DOCUMENTS

| 4,981,957 A | 1/1991 | Lableu et al. |
| 5,034,506 A | 7/1991 | Summerton et al. |
| 5,118,800 A | 6/1992 | Smith et al. |
| 5,166,315 A | 11/1992 | Summerton et al. |
| 5,185,444 A | 2/1993 | Summerton et al. |
| 5,319,080 A | 6/1994 | Leumann |
| 5,359,044 A | 10/1994 | Cook et al. |
| 5,393,878 A | 2/1995 | Leumann |
| 5,446,137 A | 8/1995 | Maag et al. |
| 5,466,786 A | 11/1995 | Buhr et al. |
| 5,514,785 A | 5/1996 | Van Ness et al. |
| 5,519,134 A | 5/1996 | Acevedo et al. |
| 5,567,811 A | 10/1996 | Mistura et al. |
| 5,576,427 A | 11/1996 | Cook et al. |
| 5,591,722 A | 1/1997 | Montgomery et al. |
| 5,597,909 A | 1/1997 | Urdea et al. |
| 5,610,300 A | 3/1997 | Altmann et al. |
| 5,627,053 A | 5/1997 | Usman et al. |
| 5,639,873 A | 6/1997 | Barascut et al. |
| 5,646,265 A | 7/1997 | McGee |
| 5,670,633 A | 9/1997 | Cook et al. |
| 5,698,685 A | 12/1997 | Summerton et al. |
| 5,700,920 A | 12/1997 | Altmann et al. |
| 5,792,847 A | 8/1998 | Buhr et al. |
| 5,801,154 A | 9/1998 | Baracchini et al. |
| 6,268,490 B1 | 7/2001 | Imanishi et al. |
| 6,525,191 B1 | 2/2003 | Ramasamy |
| 6,582,908 B2 | 6/2003 | Fodor et al. |
| 6,600,032 B1 | 7/2003 | Manoharan et al. |
| 6,670,461 B1 | 12/2003 | Wengel et al. |
| 6,673,661 B1 | 1/2004 | Liu et al. |

(Continued)

FOREIGN PATENT DOCUMENTS

| WO | WO 98/39352 | 9/1998 |
| WO | WO 99/14226 | 3/1999 |

(Continued)

OTHER PUBLICATIONS

Kaikkonen et al., "Non-coding RNAs as regulators of gene expression and epigenetics" Cardiovascular Research (2011) 90(3): 430-440.
Lam et al., "Rev-Erbs repress macrophage gene expression by inhibiting enhancer-directed transcription" Nature (2013) 498(7455): 511-555.
Li et al., "Functional roles of enhancer RNAs for oestrogen-dependent transcriptional activation" Nature (2013) 498(7455): 516-520.
Orom et al., "Long non-coding RNAs and enhancers" Curr Opin Genet Dev. (2011) 21(2): 194-198.
Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.
Allshire, "Molecular biology. RNAi and heterochromatin—a hushed-up affair." Science (2002) 297(5588): 1818-1819.
Altmann et al., "Second Generation Antisense Oligonucleotides Inhibition of PKCO. and c—RAF Kinase Expression by Chimeric Oligonucleotides Incorporating 6'—Substituted Carbocyclic Nucleosides and 2'—O—Ethylene Glycol Substituted Ribonucleosides" Nucleosides Nucleotides (1997) 16: 917-926.

(Continued)

*Primary Examiner* — Dana Shin
(74) *Attorney, Agent, or Firm* — Ionis Pharmaceuticals, Inc. Patent Dept.

(57) ABSTRACT

Disclosed herein are methods and compounds for inhibiting gene expression by inhibiting enhancer RNAs (eRNAs). Such methods and compounds are useful for reducing expression of certain genes, many of which are associated with a variety of diseases and disorders.

10 Claims, No Drawings

(56) References Cited

U.S. PATENT DOCUMENTS

| | | |
|---|---|---|
| 6,770,748 B2 | 8/2004 | Imanishi |
| 6,794,499 B2 | 9/2004 | Wengel et al. |
| 7,034,133 B2 | 4/2006 | Wengel et al. |
| 7,053,207 B2 | 5/2006 | Wengel |
| 7,399,845 B2 | 7/2008 | Seth et al. |
| 7,427,672 B2 | 9/2008 | Imanishi et al. |
| 7,547,684 B2 | 6/2009 | Seth et al. |
| 7,696,345 B2 | 4/2010 | Allerson et al. |
| 2001/0053519 A1 | 12/2001 | Fodor et al. |
| 2003/0228597 A1 | 12/2003 | Cowsert et al. |
| 2004/0171570 A1 | 9/2004 | Allerson et al. |
| 2005/0130923 A1 | 6/2005 | Bhat et al. |
| 2007/0031844 A1 | 2/2007 | Khvorova et al. |
| 2008/0039618 A1 | 2/2008 | Allerson et al. |
| 2009/0012281 A1 | 1/2009 | Swayze et al. |
| 2011/0293643 A1 | 12/2011 | Wilkes |

FOREIGN PATENT DOCUMENTS

| | | |
|---|---|---|
| WO | WO 00/63364 | 10/2000 |
| WO | WO 01/49687 | 7/2001 |
| WO | WO 03/004602 | 1/2003 |
| WO | WO 2004/011624 | 2/2004 |
| WO | WO 2004/035765 | 4/2004 |
| WO | WO 2004/106356 | 12/2004 |
| WO | WO 2005/021570 | 3/2005 |
| WO | WO 2005/121371 | 12/2005 |
| WO | WO 2006/047842 | 5/2006 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2010/036696 | 4/2010 |
| WO | WO 2010/036698 | 4/2010 |
| WO | WO 2011/017521 | 2/2011 |
| WO | WO 2011/139702 | 11/2011 |
| WO | WO 2012/065143 | 5/2012 |
| WO | WO 2013/033230 | 3/2013 |
| WO | WO 2013/177248 | 11/2013 |

OTHER PUBLICATIONS

Altmann et al., "Second Generation of Antisense Oligonucleotides: From Nuclease Resistance to Biological Efficacy in Animals" Chimia (1996) 50(4): 168-176.

Altmann et al., "Second-generation antisense oligonucleotides: structure-activity relationships and the design of improved signal-transduction inhibitors." Biochem. Soc. Trans. (1996) 24: 630-637.

Altschul et al., "Basic Local Alignment Search Tool" J. Mol. Biol. (1990) 215:403-410.

Baker et al., "2'-O-(2 Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272: 11944-12000.

Braasch et al., "Locked nucleic acid (LNA): fine-tuning the recognition of DNA and RNA" Chem. Biol. (2001) 8:1-7.

Braasch et al., "Novel Antisense and Peptide Nucleic Acid Strategies for Controlling Gene Expression" Biochemistry (2002) 41(14): 4503-4510.

Branch et al., "A good antisense molecule is hard to find," TIBS (1998) 23:45-50.

Carroll. et al., "Genome-wide analysis of estrogen receptor binding sites" Nature Genetics (2006) 38: 1289-97.

Chen et al., "Changes in Attitude, Changes in Latitude: Nuclear Receptors Remodeling Chromatin to Regulate Transcription" Molecular Endocrinology (2006) 20: 1-13.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Core et al., "Nascent RNA Sequencing Reveals Widespread Pausing and Divergent Initiation at Human Promoters" Science (2008) 322: 1845-8.

Creyghton et al., "Histone H3K27ac separates active from poised enhancers and predicts developmental state" Proc. Natl. Acad. Sci. USA (2010) 107: 21931-21936.

Crooke et al., "Basic Principles of Antisense Therapeutics" Antisense Research and Application (1998) Chapter 1:1-50.

Crooke et al., "Pharmacokinetic Properties of Several Novel Oligonucleotide Analogs in mice" J. Pharmacol. Exp. Ther. (1996) 277(2):923-937.

De Santa et al., "A large fraction of extragenic RNA pol II transcription sites overlap enhancers" PLoS Biol (2010) 8: 1-17.

Ebisuya et al., "Ripples from neighbouring transcription" Nat Cell Biol (2008) 10: 1106-1113.

Elayadi et al., "Application of PNA and LNA oligomers to chemotherapy" Curr. Opinion Invenst. Drugs (2001) 2:558-561.

Feng et al., "A Circadian Rhythm Orchestrated by Histone Deacetylase 3 Controls Hepatic Lipid Metabolism" Science (2011) 331: 1315-1319.

Fontaine et al., "The Nuclear Receptor Rev-erbα Is a Liver X Receptor (LXR) Target Gene Driving a Negative Feedback Loop on Select LXR-Induced Pathways in Human Macrophages" Molecular Endocrinology (2008) 22: 1797-1811.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

Fullwood et al., "An oestrogen-receptor-α-bound human chromatin interactome" Nature (2009) 462: 58-64.

Gautschi et al., "Activity of a Novel bcl-2/bcl-xL-Bispecific Antisense Oligonucleotide Against Tumors of Diverse Histologic Origins" J. Natl. Cancer Inst. (2001) 93(6): 463-471.

Genbank Accesion No. JN964177.1, Skarnes et al., Mus Musculus Targeted KO-First, Conditional Ready, LacZ-Tagge Mutan Allele Mmp9:tm1a(EUCOMM)Wtsi; Transgenic. Submitted Oct. 28, 2011; ownloaded from the internet <http://www.ncbi.nlm.nih.gov/nucleotie/35479976?report=genbank&lo.> on Dec. 7, 2013, pp. 1-11; p. 1, 5.

Giguere et al., "Isoform-specific amino-terminal domains dictate DNA-binding properties of ROR alpha, a novel family of orphan hormone nuclear receptors" Genes Dev. (1994) 8: 538-553.

Gu et al., "Base Pairing Properties of D- and L-Cyclohexene Nucleic Acids (CeNA)" Oligonucleotides (2003) 13(6): 479-489.

Gu et al., "Enzymatic Resolution and Base Pairing Properties of D- and L-Cyclohexenyl Nucleic Acids (CeNA)" Nucleosides, Nucleotides & Nucleic Acids (2005) 24(5-7): 993-998.

Gu et al., "Synthesis of enantiomeric-pure cyclohexenyl nucleoside building blocks for oligonucleotide synthesis" Tetrahedron (2004) 60(9) 2111-2123.

Guttman M et al., "Chromatin signature reveals over a thousand highly conserved large non-coding RNAs in mammals" Nature (2009) 458:223-227.

Hadjur et al., "Cohesins form chromosomal cis-interactions at the developmentally regulated IFNG locus" Nature (2009) 460: 410-3.

Hah et al., "A rapid, extensive, and transient transcriptional response to estrogen signaling in breast cancer cells" Cell (2011) 145: 622-34.

Hall et al., "Establishment and Maintenance of a Heterochromatin Domain" Science (2002) 297: 2232-2237.

Harismendy et al., "9p21 DNA variants associated with coronary artery disease impair interferon-γ signalling response" Nature (2011) 470: 264-8.

Heintzman, et al., "Distinct and predictive chromatin signatures of transcriptional promoters and enhancers in the human genome" Nat. Genet. (2007) 39: 311-318.

Heinz et al., "Simple combinations of lineage-determining transcription factors prime cis-regulatory elements required for macrophage and B cell identities" Mol. Cell. (2010) 38: 576-589.

(56) References Cited

OTHER PUBLICATIONS

Horvath et al., "Stereoselective synthesis of (−)-ara-cyclohexenyl-adenine" Tetrahedron Letters (2007) 48: 3621-3623.
Hou. et al., "Cell type specificity of chromatin organization mediated by CTCF and cohesin" Proc. Natl. Acad. Sci. (2010) 107: 3651-6.
http://www.ncbi.nlm.nih.gov/geo/ GSE27823.
Huang et al., "Coronin 2A mediates actin-dependent de-repression of inflammatory response genes" Nature (2011) 470: 414-418.
International Search Report for application PCT/US13/42163 syrf Dec. 17, 2013.
Jenuwein, "Molecular biology. An RNA-guided pathway for the epigenome." Science (2002) 297(5590): 2215-2218.
Jin et al. "Identifying estrogen receptor alpha target genes using integrated computational genomics and chromatin immunoprecipitation microarray" Nucleic Acids Res. (2004) 32: 6627-35.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.
Kagey. et al., "Mediator and cohesin connect gene expression and chromatin architecture" Nature (2010) 467:430-5.
Kapranov et al., "RNA maps reveal new RNA classes and a possible function for pervasive transcription" Science (2007) 316:1484-1488.
Khalil et al., "Many human large intergenic noncoding RNAs associate with chromatin-modifying complexes and affect gene expression" Proc. Natl Acad Sci USA (2009) 106:11667-11672.
Kim et al., "Widespread Transcription at Neuronal Activity-Regulated Enhancers" Natue (2010) 465:182-187.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kumar et al., "The first analogues of LNA (locked nucleic acids): phosphorothioate-LNA and 2'-thio-LNA" Bioorg Med Chem Lett. (1998) 8:2219-2222.
Kwon et al., "Sensitive ChIP-DSL technology reveals an extensive estrogen receptor α-binding program on human gene promoters" Proc. Natl. Acad. Sci. (2007) 104: 4852-7.
Letsinger et al., "Cholesteryl-conjugated oligonucleotides: Synthesis, properties, and activity as inhibitors of replication of human immunodeficiency virus in cell culture" PNAS (1989) 86:6553-6556.
Leumann et al., "DNA Analogues: From Supramolecular Principles to Biological Properties" Bioorganic & Medicinal Chemistry (2002) 10:841-854.
Lin et al., "Whole-Genome Cartography of Estrogen Receptor α Binding Sites" PLoS Genet. (2007) 3: e87.
Maher et al., "Comparative hybrid arrest by tandem antisense oligodeoxyribonucleotides or oligodelxyribonucleoside methylphosphonates" Nuc. Acid. Res. (1988) 16(8): 3341-3358.
Manoharan et al., "Chemical Modifications to Improve Uptake and Bioavailability of Antisense Oligonucleotides" Arm. N.Y. Acad. Sci. (1992) 660: 306-309.
Manoharan et al., "Cholic Acid-Oligonucleotide Conjugates for Antisense Applications" Bioorg. Med. Chem. Lett. (1994) 4:1053-1060.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Lipidic Nucleic Acids" Tetrahedron Lett. (1995) 36(21):3651-3654.
Manoharan et al., "Oligonucleotide Conjugates: Alteration of the Pharmacokinetic Properties of Antisense Agents" Nucleosides & Nucleotides (1995) 14(3-5):969-973.
Martin, "Ein neuer Zugang zu 2'-0-Alkylribonucleosiden und Eigenschaften deren Oligonucleotide" Helv. Chim. Acta (1995) 78: 486-504.

Meissner et al., "Genome-scale DNA methylation maps of pluripotent and differentiated cells" Nature (2008) 454: 766-770.
Mishiro, T. et al., "Architectural roles of multiple chromatin insulators at the human apolipoprotein gene cluster" EMBO J. (2009) 28: 1234-45.
Mishra et al., "Improved leishmanicidal effect of phosphorotioate antisense oligonucleotides by LDL-mediated delivery" Biochim. Biophys. Acta (1995) 1264:229-237.
Nativio et al., "Cohesin is required for higher-order chromatin conformation at the imprinted IGF2-H19 locus" PLoS Genet. (2009) 5(11): e1000739.
Nauwelaerts et al., "Cyclohexenyl nucleic acids: conformationally flexible oligonucleotides" Nucleic Acids Research (2005) 33(8): 2452-2463.
Nauwelaerts et al., "Structural Characterization and Biological Evaluation of Small Interfering RNAs Containing Cyclohexenyl Nucleosides" J. Am. Chem. Soc. (2007) 129(30): 9340-9348.
New England Biolabs 1998/99 Catalog (cover page and pp. 121 and 284).
Newman et al., "Connecting transcriptional control to chromosome structure and human disease" Cold Spring Harb. Symp. Quant. Biol. (2011) 75: 227-235.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Orom et al., "Long noncoding RNAs with enhancer-like function in human cells" Cell (2010) 143:46-58.
Orum et al., "Locked nucleic acids: A promising molecular family for gene-function analysis and antisense drug development" Curr. Opinion Mol. Ther. (2001) 3:239-243.
Pal-Bhadra et al., "Heterochromatic silencing and HP1 localization in *Drosophila* are dependent on the RNAi machinery." Science (2004) 303(5658): 669-672.
Pennacchio et al. "In vivo enhancer analysis of human conserved non-coding sequences" Nature (2006) 444:499-502.
Ponting et al., "Evolution and functions of long noncoding RNAs" Cell (2009) 136: 629-641.
Prabhakar et al., "Close sequence comparisons are sufficient to identify human cis-regulatory elements" Genome Res. (2006) 16:855-863.
Prasanth et al., "Eukaryotic regulatory RNAs: an answer to the 'genome complexity' conundrum" Genes Dev. (2007) 21:11-42.
Preitner et al., "The Orphan Nuclear Receptor REV-ERBα Controls Circadian Transcription within the Positive Limb of the Mammalian Circadian Oscillator" Cell (2002) 110: 251-260.
Reynolds et al., "Rational siRNA design for RNA interference" Nature Biotechnology (2004) 22(3):326-330.
Robeyns et al., "Oligonucleotides with cyclohexene-nucleoside building blocks: crystallization and preliminary X-ray studies of a left-handed sequence GTGTACAC." Acta Crystallogr Sect F Struct Biol Cryst Commun. (2005) F61(6): 585-586.
Robeyns et al., "Structure of the Fully Modified Left-Handed Cyclohexene Nucleic Acid Sequence GTGTACAC" J. Am. Chem. Soc. (2008) 130(6): 1979-1984.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sanghvi et al., "Heterocyclic Base Modifications in Nucleic Acids and Their Applications in Antisense Oligonucleotides" Antisense Research and Applications (1993) pp. 273-288.
Schlaeger et al., "Tie2Cre-mediated gene ablation defines the stem-cell leukemia gene (SCL/tall)-dependent window during hematopoietic stem-cell development" Blood (2005) 105: 3871-3874.
Shea et al., "Synthesis, hybridization properties and antiviral activity of lipid-oligodeoxynucleotide conjugates" Nucl. Acids Res., (1990) 18, 3777-3783.
Singh et al., "LNA (locked nucleic acids): synthesis and high-affinity nucleic acid recognition" Chem. Commun. (1998) 455-456.

(56) References Cited

OTHER PUBLICATIONS

Singh et al., "Synthesis of 2'-amino-LNA: A novel conformationally restricted high-affinity oligonucleotide analogue with a handle" J. Org. Chem. (1998) 63: 10035-10039.

Solt et al., "Regulation of circadian behaviour and metabolism by synthetic REV-ERB agonists" Nature (2012) 485: 62-68.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.

Struhl et al. "Transcriptional noise and the fidelity of initiation by RNA polymerase II" Nat Struct Mol Biol (2007) 14: 103-105.

Svinarchuk et al., "Inhibition of HIV proliferation in MT-4 cells by antisense oligonucleotide conjugated to lipophilic groups" Biochimie (1993) 75:49-54.

Tsai et al., "Long Noncoding RNA as Modular Scaffold of Histone Modification Complexes" Science (2010) 329: 689-93.

Verbeure et al., "RNase H mediated cleavage of RNA by cyclohexene nucleic acid (CeNA)" Nucleic Acids Research (2001) 29(24): 4941-4947.

Verdel et al., "RNAi-mediated targeting of heterochromatin by the RITS complex." Science (2004) 303(5658): 672-676.

Vester et al., "Chemically modified oligonucleotides with efficient RNase H response" Med. Chem. Lett. (2008) 18: 2296-300.

Visel et al., "VISTA Enhancer Browser—a database of tissue-specific human enhancers" Nucleic Acids Research (2007) 35:D88-92.

Volpe et al., "Regulation of heterochromatic silencing and histone H3 lysine-9 methylation by RNAi." Science (2002) 297(5588): 1833-1837.

Wahlestedt et al., "Potent and nontoxic antisense oligonucleotides containing locked nucleic acids" PNAS (2000) 97(10): 5633-5638.

Wang et al., "A Straightforward Stereoselective Synthesis of D- and L-5-Hydroxy-4-hydroxymethyl-2-cyclohexenylguanine" J. Org. Chem. (2001) 66: 8478-8482.

Wang et al., "Cyclohexene Nucleic Acids (CeNA) Form Stable Duplexes with RNA and Induce RNase H Activity" Nucleosides, Nucleotides & Nucleic Acids (2001) 20 (4-7): 785-788.

Wang et al., "Cyclohexene Nucleic Acids (CeNA): Serum Stable Oligonuceotides that Activate RNase H and Increase Duplex Stability with Complementary RNA" J. Am. Chem. (2000) 122: 8595-8602.

Wang et al., "Reprogramming Transcription Via Distinct Classes of Enhancers Functionally Defined by eRNA" Nature (2011) 474:390-394.

Wang et al., "Stereocontrolled Synthesis of Ara-type Cyclohexenyl Nucleosides" J. Org. Chem. (2003) 68: 4499-4505.

Welboren et al., "ChIP-Seq of ERalpha and RNA polymerase II defines genes differentially responding to ligands" EMBO J. (2009) 28: 1418-28.

Woolf et al., "Specificity of antisense oligonucleotides in vivo" Proc. Natl. Acad. Sci. USA (1992) 89: 7305-7309.

Wu et al., "Poly A-transcripts expressed in HeLa cells" PLoS One (2008) 3:e2803.

Yang et al., "ncRNA- and Pc2 Methylation-Dependent Gene Relocation between Nuclear Structures Mediates Gene Activation Programs" Cell (2011) 147:773-88.

Yin et al. "The Orphan Nuclear Receptor Rev-erbα Recruits the N-CoR/Histone Deacetylase 3 Corepressor to Regulate the Circadian Bmall Gene" Molecular Endocrinology (2005) 19: 1452-1459.

Zhang et al. "PowerBLAST: A New Network BLAST Application for Interactive or Automated Sequence Analysis and Annotation" Genome Res. (1997) 7: 649 656.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

Feng et al., "The Evf-2 noncoding RNA is transcribed from the Dlx-5/6 ultraconserved region and functions as a Dlx-2 transcriptional coactivator." Genes & Development (2006) 20: 1470-1484.

SEQUENCE LISTING

<160> NUMBER OF SEQ ID NOS: 203

<210> SEQ ID NO 1
<211> LENGTH: 338
<212> TYPE: DNA
<213> ORGANISM: Mus musculus

<400> SEQUENCE: 1

```
tgtggggtg gcaatggagg aagttggggg tagggagaga agtgttcttg ctttgatgga      60
ttccaagccc tgggttctcc ctccctccgc agttggtaag aaagaaccag cagcaatcct    120
gaaggcgagt gaagtggtac ccactgctta cccactgttc caggcacctc tgtaacaggc    180
ccacatggga aacactgtta ttagcacttg tttttaagat gggggaaatg gtaggttgtg    240
tcgatagctg gggtcacaca atgagctgaa gcttggattt cggcagtcca atcccagagt    300
gggagccccc attggcctac tcactctgcc tgccaagt                            338
```

<210> SEQ ID NO 2
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2

```
attgtgtgac cccagc                                                     16
```

<210> SEQ ID NO 3
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 3
caagcttcag ctcatt                                                        16

<210> SEQ ID NO 4
<211> LENGTH: 27001
<212> TYPE: DNA
<213> ORGANISM: Mus musculus

<400> SEQUENCE: 4
tccttccttc cttccttcct tccttccttt cttccttcct tcccacctgt tctctctctc          60
tctctctctc tctctctctc tgttattgtt cttttggttt tgttttgggg ttttttttggt        120 tttttttggtt ttttggttttt ttggtttttt ttttttttgg tttttcaaga cagggcttct      180
ctgtatatcc ctggctgtcc tggaactcac tctgtagacc aggctggcct cgaactcaga        240
aatccgcctg cctctgcctc ccaagtgcta ggattaaagg tgtgtgccac cacacccagc        300
tttttgtttc attcttttga gacacagttt ctctgtgatt ctgtgtagct ttgactgtcc        360
tggaactcac tatgtacaca ggctagcctg gagctcagag gtccacccgt tctgcctcc         420 taagtgctgg gatcacaggc gggtgccacc acctcccatc ctaagtacat tcgtttcttg        480 ttttaaatt tatttttac actccatatt ctatcccca ccccaccccc atgcaccctc           540
cgactgctct acatcccaca cctccacccc accccacccc gcttccaagt ggatgttccc        600 aaccccaag cccacctgac ctaatctccc tggggcctcc agtctcttga gggttagatg         660
catcatctct tactaaagta cgttctcaaa tgcataaatg gttgttcttt aggaagccat        720
gggaaatcct cactttgtca atagcaaatc tagagatgta cattgggaat ctgactggtc       780
ccaggtcctc tgggccctga gttcacttct gctccctaat gtgtggcaca cctgagaatg       840
tgcagctcat aagctgatgg gtggagccca gatgacaccc cggcccgcag gtgcacaggg       900
cagacttaga ttgtctggtt ctcagctctg gctctttgac ctgctgccca gcctgtctca       960
gcccaggcct caggcagcag ttcacctcat tgcctcaaga gggagctcca aggttgccaa      1020
gataggaaat tgttggaagc gggtgactga ccaggccagc cttttcctgt ccccagctgc      1080
agctgccccc ttggagaagc agtggtggcc acttactctg cctgtgggcc ctgagggcac      1140
ctgctctggg ctctagaacc ttacagaagc caccttgttt ccaaggccag atgttgcaca      1200
tgtaaatctc tgatgtgagt ggcaggtagc ctcaagttgt ccctttaact tccttcagct     1260
tcagtctcct cacctgaaag gaaagactga aaattcaaac acaggtgcca accagggaga     1320
aaggaggaga ggcagggagg gtggggatg ggatgggaac ctgagtaaga tacaaagata     1380
caacaaaaac tccaaaccgt tcttctgagt gggcaaaccg ccatacacgt aacctcagca     1440
cttgggaggt ggaaacggga ggatcaggag tcaaggccat cctcagctcc atactgagct     1500
cctggataac ctgataaatt aacatctgac tttatatctc aatctccagg gctactgtga     1560
taactgtgac aatctggggc ctttgttttg tttctgatga ttttggagcc tggaagacca     1620
agctccaagt gtcagtggat tcgttctgag gattcaatct gtgggttgca ggcagccatg     1680
gctcactgtg tcctctgtgt ccccgtcccc ccccccgcc cccaggttgg tctcaaactt     1740
ggatgagctt ggagtcctcg tcctccacct ctgagtgctg ggatggtagt tgtgcctcgc     1800
ctcactggct tgcaggtgca ggagatcaac ccagagcaag cactgtactt accaagccac     1860 acccccaagtc atcattttca gaggagaccc tcacatgtga gtgaaggcta agtgtagctt    1920
```

```
gggagagagg gtggactgtg aggggggcag gggggcagc ctttggaaca ccagcagctc    1980
tgtccttggt ctggtgccgt ttccctgttc tggtaaattc tgacttcact actgcttcct    2040
aacatagggc acaactgaga acataacaga tgcccaacct ggaccatttc cccttattta    2100
tctacgtaaa actgagtctc ggtacattcg agttgcagga tccaccttag cctctgggta    2160
gtggggagag ggcacacagc tgggtgctcc cccattagaa tttaagatga tttttttttc    2220
ctagtaaaca gagctttcag aaaagcagag agagaagcct gtctgacagg gttgggtggt    2280
aatggggatg ggctgcagag aatgcggaga gttctaaagg accctggatg tcagcaaagc    2340
ccagggaagg gggcagctct acttggctcc ctgacagtga agcatgttct ctgccacctg    2400
gtccctctcc tggagccgtc cctgcaaaag tgaagcctgg atccctaggc agacattgct    2460
ccttcttctg tgagccccca gcttttaat ctcttactta tcctgcctgg gtagaaggtg    2520
tttttgccac tgctacaact tacaccaacc tggcctcaac tatgtcgggg ttgttgctgc    2580
tgtttcgaga taagacctcc ctctgtagct caggctggcc tcctagtcgc agcaatcctc    2640
tggcctccaa gtcgcagcaa tcctctggcc tccaagtcac agccgtcctc tggcctcggc    2700
ctcccaagtg ctgggatccc agggatgagt catatcaccc tccaagggg cagtgattag    2760 tggtggtgat caataattat taaatagtta agggctgtgg tggtaggaat ggaaatggct    2820
atcccacagc tcatgtgttg gttaactgtt tggaaagaat tggtgggtgt ggccttgttg    2880
gagggggtgt gtcactgggg atttaaaaaa ccattcccag tgtgtctctc tgcttccttc    2940 tttttggatca agatgaggat tctcagctgt tccttctgcc gtgcctttac tccaccacca    3000
tgggccctaa ctctctgaag ccataagctc aacatttcct tcttttataa gttgccttgg    3060
gtttagctga gtatcacagc gtgttgtcct gggagcttgt cctggggtaa cagaagagct    3120
cagaagttct agcttggagg gctgaggtga gaacttagat ctagaatagg ctggccacag    3180
agcaagagcc tgtctcagaa gcaagggaaa ccttaggcaa catctgatgg tttattttgg    3240
aataaaaaag aacttttgct tccatttgtt ttgtttattt tgggttttt tttggggggg    3300 ggttcttcat tatttagaga atactttatt agttttgta atcaaaccca cgtagataag    3360
accttacata tttaacacag tgcattgccc ctgtacaaat ggggaaaaaa ttaagtccaa    3420
catttctaga ccaatatggc tgtccatttc tgttcaatgc caactcaaca cagtaaactg    3480 gatactttt tccaaagttg acagcacttt tgcttccatt tgtaatgcac cgtagttcag    3540
ccacctccaa atgctactgc ttagaaatac tttaattggg agctcggtag ttaaaagcac    3600
tggctgctct ggaagagggc ctggatttga ttcccgcccc actatgtgac tcacaaccct    3660
agtctcaggg gacctgggat gccctcttct ggcctctttg ggtccaagca tgcatgtggc    3720
agtggccata cagacaaaca cttatatcca taaaataaca aaaataggtc tcgaaagaaa    3780
tagtttaata ggaggctgga aagatggctc agtggttagg agtgctcact gccttctaga    3840
ggtcagtgtg ggtcccagca cccacgtcag atggctcaca cccacatata gctccagagc    3900
cagggatcag tgctctattc tggacttcat ttatgctata tagactgtac acacacacac    3960
acatgcacac acatacatgc ccacacacac ttgcacacac acatgtgcat acatacatgc    4020
ccacacatac atgcacacac acttgtgcac acatacatgc ccacacacac ttgcacacat    4080
acatacccac acatacatac ccacacacac ttgcacacac atgcacagat ggatgaggta    4140
cagtctgtgg ccttcaggtc catagagcag gcttgctgcc tcctcaccct gaaatgggat    4200
gtcctgcaac tcaggcgag ctcagtgccc tcggtgtgtg cagccgtcca tctgggaaca    4260
aggataccag cgtgagttac tgacactcgt cacagagctc acctgctgcg gcatccatga    4320
```

```
gcaggacagg ctggcttgtc agcccacagc aggtgaggca gggaggaaag gcatgcacag    4380
gccaggggat gtgtgtgctg gagaagagga agcggataga atgcagtggg aagtaaaaag    4440
aagccatggt gctgagaaca tgctcaccag acagaagaga ggagcctccg agagtgctaa    4500
gtctgtgatg ctacgactcg gggtcctctc tggcacatgg gtagatggcc ggatggtgag    4560
atgaataaga tggatgggaa gggagtggtg ggcacagggt accctcaggc cccagctgaa    4620
ggtggagttg tgtgggaaac agacacggat gagattggtt gacagcaaca gtaggagatt    4680
ctcagccaga ttccagacag gaacacgagg aagagcttga atgccctggg gatacagctc    4740
agatggcaaa atgttagact agcctgagtt ccatccccag ccctcataa acggtggagc     4800 atcccagact tgggcagtgg aggcaggagg atgaaaggct caaggtcttt ttaaccccat    4860
agctatttaa agtccagccc aggatgtgtg ggacctatct caacaacaaa acaaacaaaa    4920
acaaagccag ggggctgaag aaatggctcg gtggctaaga gcacacactg ctcttgcaga    4980
ggacacaagt tcgactccca gcacctatag tgatgggcaa ctcacgactg ccacaggagg    5040
atctgagttc tctagcctcc ctgggcacat atacataatt aaaagaaag ctcgaaaaca     5100 aaaagtttag cagaaatgaa taaggacacg gagtcggtga ctggaatag atgggggtg      5160 gttctgggag gagagggta gaggagggat tgtgatcgaa atacatgtga agttcccaag     5220
gaattcatac aaataaaagc caaaaaaaca agagctgaag tggggacagg atcgggtga    5280 ggagctgagc cccaggggaa gctgagtagc ccctgactta gctgctgggg caacgggaaa    5340
gggccaatgt ctgcgagcct gtgaggatct gctggctctc tgtgaatctc tcctgcaggg    5400
aaagaagaac agacagggag gccagaagga aggagaaagg gaactaaccg aggcttcctc    5460
aaatgtgaac agctggagag caactggagc ttttagttcc tacctcactg gacaaagcag    5520
gctcctgaga actcccaaga gttgtgatat ggtcagtggt cagcgaacct gggcccagtg    5580
ctgcacaggg ggtaccagag gcttcctaag aacactggaa agcagagggg ccctcacagc    5640
ttgcctgaga cccctattaa ggagagcttg agacctgact tgtgtgctgc tggactccga    5700
ggctacagac tgccatctca ctaggaataa ataatatcca tccaccccca ggtctgccaa    5760
cccacagccc cctgtaaacc ttaggtctca gtaattccta ggtcagccac cacacagtct    5820
ccagcaatcc ccaggtctgc cacccaacag tccccagtag tccccagcag tcccagcaa     5880 tctccaggtt tgcccagtc tcaagtcccc tagatttgaa atgcaggctc tcttgcggtc    5940
agctggttcc cagcctggag cgttgagccc gttgagcttg cttgtcacag catctaaaga    6000
tagggtacca cacaggaaac cagatgctat tggctaactt cgaaaataaa gatgccctca    6060
tagagaggga agcacttgcc tctggtggag tctgcgtgag actgggtgag tgactggcac    6120
ttcctgcaga agttcccttc ccatctgctc aggtaagtac cacggactcc agactcctcc    6180
catacctggg cgtggggtca atcaggcaca gtcacagggt ttctgatgct gtttgccttc    6240
cgtgtctatt ttcctgagga tactgcagat aaatcaggag agtaaaggac cttttgcacg    6300
ctcgtaactt gaggagttag taattacatt ttagggatgt gaaaaaaaag gtttatatta    6360
gatgttacca aaaaggcct tgatataaaa tcacatctgg gtaattggaa atattgatat      6420
tcttaaagat cacaattcag attgccagtc agactttttt gatccatgcc tctaatccca    6480
gcacttggga aggtgaagca ggaggatcga tacaagtttg agaccagcct aggctagcta    6540
atgagctcta ggccagttta ggcttctgtg tgagaccgcc ttaaacaaac agcaccaacc    6600
ataaaaacta gtgattgtgg ttttcatttc ttttaaaag gagcttttat cttcagagac     6660
```

```
tcatacttga atgtctatag aaacagaata atctaattca gccatgaaat aggacataga      6720
tgaaatatta actgggagtt gataattcct ggagctgagt ggcgggtgcc aggtgtttcc      6780
tttgatttcc cccccccccc ccccggtttt ttgagacagg ttttttctgt gtaactgtga      6840
ctatcctgga actcattctg tagaccaggc ttgccttgaa cttatagaga tccacctgcc      6900 tctgcccccct cagtactggg attaaaggcg tgcgcctcca ttgcctggct ccctgattg      6960 tatataggct tgtgaatata aagagaataa tgttatataa atagagttgc ttgcctagca      7020
cacaaggagc cctgggccct gggcacaatc ttcagcatct aataaaattg gacttggtgg      7080
cacacactgt gatcacagca ccctggaggt aaaaggcggg aggtcggaag tgcaagactc      7140
ttctcagtga agcagaattt tgaggccagc ctggacttta tgggatcctg cctctaaaaa      7200
caacaataat gatgatggtg acggtggtgg tgatgacggt ggtggtggta gtggtggtgc      7260
tggtggtggt ggtggtggtg gtggtggtgg tggtgataaa tgttcaaaac gatgttagca      7320 ttttttactat aaatataaat ttatgtgtca aaaaagctaa gagtgctatg ctaaacctgc      7380
agagttggat agttttaagg attcctcttc ccctcccccct cttttaaatg ctttttttggt     7440 accatcttca atagtcataa tgaacattta ttacatttat aataaacttg tcacaaactc      7500
attcttcagt tttataaatg ctcagaacca tggctcagac acttgggcac agacatctga      7560
gctaggagtc gtggtcttag ggaggaaacg ataagaacag gccaggaggg ctggagaggt      7620
ggctcagtgg ttaagagcac cgactgctct tccgaaggtc ctgagttcaa atcccagcag      7680
ccacatgatg gctcacgacc atccgtaatg agatccgacg ccctcttctg gtgtgtctga      7740
agacagctac agtgtactta gatataataa ataaatcttt aaaaaaatat ttaaaaaaaa      7800
aaaacgaaca ggccaggagg agatacaccc ctgcttgaca cagacaagcc cctattcaga      7860
ggaccctgca gcctcgctca ctctgtgcct gatcatttat aaccatgtgc gagaaaagct      7920
gggaacttgg gattctcctg ccttctgtct ttccaattct gccattttt ttcttttaat       7980 ttttttcccaa ctgcttgaaa tacaatactt gaggtaggaa gaaattcagt caaatgtgaa     8040
gatacgcagg tcataagaag accctgttca ggcccaggtc ataagagggc cccagcctac      8100
tgagaggaga caagctcaga gtgagacctg gcctgctgag ccttgggaac ctatgagggt      8160
cagcagggta ggtgcagtgg ctgaactgga atggggtttt cctggacaac agaaatggcc      8220
ccaggaagct gttcggtggc ttttcccaga gaaatgtgaa ccaagttatc caccaacgct      8280
atgactcctg gggcaagcag gaacgacccc acacccaagt ttaggctgga gaatcagcaa      8340
gtcttttggg gttactcata gcaacatgcc ctagggttag tcacagctta tctcagtggg      8400
gtgcccactc atgagagctg tgttcctggg actccttagc ctcctgagag ggaaccttgt      8460
aagttagctg aatcctgtga gcctctatcc ccttttcctgg aggccatcgt ggcttcttta     8520
ccctctatcc tgttcacctt tgttttttatc aaaggatgct ggagcagaaa atagtcccag     8580
cccagttcag tctggctagc ctggcccttc acacacccct ttttttctgg gaagaagaac     8640
ccgaccaatg ctaatctctt tgaaatatat cctccgcccc ttgcttctgc cgaccccatt      8700
gcacagggag ggctggaggg tggtgggaga tgctgttcaa cttagggaca cagtacacac      8760
tgcccctgcc aacacttctg gcaaagtcag cttcctgctt ttcctatggc agtaggcttc      8820
ggagtgcacc gttagagtgt ggtatgcaaa gtcccaaaca cacattggac gtctttagtg      8880
cctaaaacaa tacgggccag caaagtggat tcaggcacct gttgctgatg tgttagaatg      8940
gcggtcgcat ctcagcagca ctctgggcca aggcagttcc acgtggaaga ggttttattg      9000
gggaaagaga gagaaggtgg ctgaataaac agaacaggca aggagagaga gtgcgagcag      9060
```

```
tgttctcctt atttatatgg agaatgacat aacgcaggta aaggtggaag gtgagccaag    9120
tggatgttgg gaatatggtg cctgttgcct tggcaacctg tctgcaggtc gcaagtcatg    9180
ctgttgccta tgtgatgtcc tgatgccaac agttgccaag cttgaccacc tgagtttgat    9240
ccctgggaca tgcgcagtag aaggacagaa ctgactccct caagatgtaa tctgaccacg    9300
tgttgtggca tgtgcgaaag tgtgtgtggg gaggagcgtg ggcccccccc cacacacaca    9360
cacacacaaa tgatcaaggt gtactctaac ctgcatcgtg gctagtccaa gtgtgtgcac    9420
acatacatat aaataaatgt aattttaaaa accatgcatg tctattactt cagggaaagt    9480
taagctctgt gaccttaggg ctttaaaatg acagcctgct ttcagaggtt actaaggatc    9540
ccaggtcgtg ggaacgggag cgaagaaggc atgctagggc tgatccagat caaaaccaac    9600
tctagttcct tcttctcccg agccagctgt gcagggGtgg ccatgtcagg catggcctgg    9660
ggactgcatg agctgcaggg ggggaactca ggctgttgcg gggggagga ggggtcggg     9720 gtggggagac cctcgctgac tttgatgagc cacagctcag gagctctcag aagctgggac    9780
cttgtgtgac tcaggtcatt gcctgccaag gaaaaccaaa ggaaggctaa ggcttgtgac    9840
caaatctgtg gtctgccttt cctcctggag gttcagggca aactgccctg agggtggaat    9900
ctccctgaac tctgaatgga gagcgcttta accaactcat ctggtcaaat tgttttgaat    9960
tatgagtatt aatagaaaaa agcaaatctg tattgctttt ccttaaatgc ctttccagaa   10020
cattgctaag ctaaacctac tgactatgta gcacagtacg ctgagagaca tgaaaggtca   10080
tcagcaatat aggccaggct attggagaga ggcaggagga agtcagtgag tttgaggcca   10140
tcttggagac ccaggacaac ataaagagac cctgtctcaa caacaacaac aaaaaacttc   10200
attatataaa accttgcaaa cagttttttt aaatctcaca tcagaattaa tcagctccaa   10260
tgtcaatgca ccataatgaa cgtatagttt gaattggcat ttgaatttcc tccaggctct   10320
ctggggtgga gtctgcagct ctcctgtccc cctcttctgc tacacagcca gcttggctct   10380
ctgtaaacca ggctgcccct gaaatctccc aaacaagtag gctcttcccc accccaccc    10440 ccacatcccc tcttgtctgc tgttttgggt actttctctc acatcctctc tacttgacca   10500
ggaaacccca gactcagccc ctctgagcct acctcacctc attccctgat acctccctct   10560
gtctgcaagt ttcctcccac cttaaaagt ttcttttaaa atatttattt attttagtt    10620 tacatgcatt gatgttttgt ctgcatgtat gtctgtgtga gggtgtcaga tccctggaa    10680 ctggagtcac agactgtcgt gagctgccat gtgggtgctg ggaattgaac ccaggtcttc   10740
tgggagtgct agtagccagt gctcttagtt gctgagccat ctctccagac ctaaaggtga   10800 cttttatga caccctttta tgccctcct tcagtcctaa aggagacaga aatagagacc   10860
caagcctgag tctattattt aaccttccct gtatttggtg ataaacattt atagagctgc   10920
ttctgtgttt ctttctcagc aggttcttgt acagcactca tccagtacag tacttgtctt   10980
agttagggtt ttactgctgt gaacagacac catgaccaag gcaagtctta taaaaaacaa   11040
catttaactg gggctgcctt acaggttcag aggttcagtc cattatcatc aaggtgggag   11100
catggcagta tccaggcagg catggtgcag gcagagctga gagttctaca tcttcatcca   11160
aaggctgcta gtgaagact gacttccagg caactagtgt gaggatctta tcccacacc    11220 cacagtgaca caccccattcc aactaggtca cacctattcc aacaaagcca caccttcaga   11280
tggtgccact ccctggtcca aggatataca aaccatcaca ctccactccc tggtccccac   11340
agacttgttc aaaaacatga gtctatgggg gccatactta aacatagcat aatgcaaaat   11400
```

```
gcatttagtc caactttcaa agtcctcata gtctatagca gtcgcaacaa tgttaaaagt    11460
ccaaagttca agggctcttc tgagattcat ccaactaatt aactgtaatc cccaaagcaa    11520
ggcaggaaac cagctgtgca aactccaaac tctgcatctc catggctgat gtcaaagcgg    11580
tcttcagatc tcctctcctt tttcatcttt gttgactgca acaaactgct ttctcctggg    11640
ctggttccac tccctgttag cagctttcct cagcatgtat cccatggctc tggtatcttt    11700
aacatctttg agtctccaag gcaatttcaa tgttacagct tcttgtttca gtgtctggga    11760
ttctacttga tcttttggac tcctccatca cttttccagc tctgccctct gtagcactct    11820
aagctcaggt tgttcactcc actacggctg ctgttctctt ggtgatcatc ttactgacat    11880
ctccaataca ctggggtgtt ccactccaac taagcttcac caatagcctc tcataggctc    11940
tcttcagggt gccaagcctc aaatccttttg catgacccct tcagtcctgg gccatcaact    12000
acagctgagg cttcaccttc tccagtggcc ttccctggcc tctcacagtg ctaagcctca    12060
gcttctctcc atgatccctt cattccttca caagcatact gcctgagtca cctgagtgac    12120
tcttacacat taccaagtcc agtcgcagca tgaggtacaa ccttgggtat ctctggaaca    12180
cagctacttt gtgctctcag aaaacaattt ccagaagatt ttacctcagt gatgctggta    12240
tcttcttaat cactactaat tccttagctc cagctaacca gcatcaattg ccccagtagt    12300
tccttccatt cttaactcta gagccagagc ctcatggctg aagctgccga gttctgctgc    12360
ttacaggaac tagaacatga tccccttgta ctattattac attatcacta gctttatgtt    12420
ttctaaatcc ttcactgcct aagcttggct atcctggttc ttgctctgta gattgacctt    12480
gaatgcagag atcagcatgc ctgtctcatg ggattaaagg tgtataccac catgcctggt    12540
tctaaattca gctgggtagg gtcttgcccc aaggtcccac tcccttaatc tgttatttcc    12600
tagaacacag gattttttctt catttcactt cctggtatgc ctttaatact cgaaccatat    12660
attttatatt ttgcctttct aagcttgcta tgcttgttca aacttctctt tgtgagactt    12720
aaccagagaa caaagtctct gctgggcttt tttgaaactt cctttgtcag tgcaattaat    12780
gcaattaatc caagtctctt caccttagcc tcaggcagac ttttcagaca agggtaaaaa    12840
gtaaccacat tcttcaccaa aataccacaa aaacagtctt tatgccacat tctgaaattc    12900
ttctcctttc ttgggccagg tcaatacagt tcaaattact cccagcaaca aagtcttcca    12960
taatcctact aggatgacca attaaacccc atttaaagca ttccactgct tcccaaatcc    13020
aaagtcccaa aatccacatt cttttcaaata aagcatggtc aggcctatca cagcaatacc    13080
ccactcctgg taccaacttt tgtcttagtt agggttttac tgctgtgaac agtaaaccca    13140
tgaccaaggc aagtcttcta aaaaaacaac atttaattgg ggctgcctta caggttcaga    13200
ggttcaatcc attatcatca aggtgggagc atggcagtat ccaggcaggc atggcgcagg    13260
aggagctgag agttctatat cttcatctaa aggctgctag tggaagactg acttccaggc    13320
aactagggtg aggatcttat acccacactc acagtgacac acccattcca accaggtcac    13380
acctattcca acaaggccat accttcagat ggtgccactc cctggtccaa agatataaaa    13440
accatcacag tactctagag cagaatgaaa atcaaaagct tcttgtagca cagaatcttc    13500
ccggacagag atcaaagaga aaggaagccc tccccttacc tgctcaataa accagagtgt    13560
gttatcctag acaatctact aggaatctga dacaggaatc cttcctccct tcccatttca    13620
catacaatca aatgcatcag tccttaaggt gatcaacaac tgtgcatgaa gcaagaggac    13680
ctgacagcgt atacatacat acatgcatgt gtgagagcat gtgtgcacgt gtgtatatgt    13740
gtgtgtgtat gcatgcatga gtgcatgcct gcatttgtga atgtatgtgt gtatgcatgc    13800
```

```
atgcttgtgt gtgtgcatgt gtgtatacat gagtgtgtgt gcatgtgtgt gtgtgtgtgt    13860
gtgtgtgttt acgtgtgtaa aaccaacatc cagtgccctt ctcagtcatt tccaccttgt    13920
cttttcagag agggtctctt cttttcttt agaactcacc catttggttg ggtcaactgg     13980
tgagagagct ccaaagatcc ctctgcattt tccaaatgct ggggttatat catgcctagc    14040
atcttatatt tttggttgtg agcctagtct ttaataactg agccatctct ccagccccat    14100
gtttagcttc cttttttttt tctttctttt tttttttttt ttttttttttg gttttttcgag   14160 acagggtttc tttatatagc cctggctgtc ctgaaactca ctctgtagac caggctggcc    14220
tcagactcag aaatccacct gcctctgcct cctaggtgct ggaattaaag gcatgcgcca    14280
ccactgccca gcccatgttt agcttcttaa tatgggttca gaggctagaa ctctcatctt    14340
ggagtttgca aaataagtaa tttgctgact gagccattcc acccacccaa gacccctgga    14400
tgttggtttt acacacaaaa acgagtgggc ttggtggctc atattttggg ttgtgagcct    14460
agcctttaac ggctgagcca tctctccagc ccggtggctc atattttaa tcacagtact    14520 gaggaggctc aagcagtgcg atttcagtga atttgaggct agcctaggct aacctagaga    14580
agtctgggtt agagatgggc aatagcatga gatctaatct caaaaacccc tacagtgact    14640
agaattctaa tattaaaaaa gtccttctgt ttctccatta cttaaaaaaa agtaataaaa    14700
catttgcttg ttcacagttt gtttgtatag aaataaacaa atgccacaaa gtgctttaaa    14760
gaggaagagg gagggagagg tatcaaacct cagataatgg tgtgctttag aaaggaggta    14820
actctgttac ccacagggag gttcctatag cttgggtttg ggtttctctt agcattcatt    14880 gttttttttgg cttggtggtg tgcctttggt ctgggctaaa ccctgctgcg caacactctc    14940
actctacttt acctgagctc atagctatag gaacagaggg tccgctaact tgcacaggaa    15000
actgggcgga aattgtaaaa ataaacagaa aaatagatag atagatagat agatagatag    15060
atagatagat agatagatag atagatagat agatagatag atagacagat aggactgtca    15120
gacactggag acatcgctcc gtcagtaaag tgtttataat acctggagac cagagctctg    15180
tcctcagaat gaactaaaag gctgtgctca gcaactcagg agaatgaaaa cctaaaggca    15240
gacaccaagt ttagaaatca ataagcagaa tctggagcca aaggagaggg ggaaacacca    15300
taatgaggat gccaacacga ggagaagcca tcttagaaga agggaagtaa agaaacagga    15360
agctggctgg aagctgtggg caacggtgcc ccatccctgg tacaaaagaa aggagtggac    15420
cccaaaaaag gaagtggcca gaggaagtgg accaggatgg gcagtgagag tgaggaggga    15480
attttataaa gtgggtcaca caggagtcat ttctgtttgg atttagaaca agtgtttctc    15540
aatcttccta atgctgcaac ccttaaatac agttcctcct gctgtggtga ctcccaacca    15600
tccaattact tcattactac ttcgtaactg tgatcttgct actgttgtga atagtaatgc    15660
acccgtctgt gttttctgat ggtcttagat gaccctgcc aaaaggctac tgggctccca     15720
aagggtcagg acccacaggt tgagaaccgc tgatgtagac cattccaatc tctgcttcta    15780
ggttcaactc agattcccca gctgaatatc agttagtgga accacaagct aatgctggag    15840
aatggagacc tgagagataa gggaggtttc cgtggacata gttgggtgga agtaggaagg    15900
gtatttgtgc ctacatgagt gtgcgtgcgt gtgtgtgtgt gtaggtgcag ctgtgcacac    15960
atgtatgtgt atgcgtgtgt gcttgtgcag gtgtacctgt gcacacatgt gcatgcatgt    16020
gtgtgtgcaa gtgcacacgt gtatgtgcat gtgtgtgtgt ataggtacag ctgtgcaaac    16080
atgtattgca tgcatgtgtg tgtgtgtgtg tgtgcgtgtg tgtgcaggtg caggtgcagc    16140
```

-continued

```
tgtgcacaca tgtatgtgta tgcatgtgga ggccagaggt caaccttatg tgtcatttct   16200
caggtacccc ccacattatg tttgtagact gtctctcaat gacatctgag cttatggtt    16260 cagatgcaag ccagtgagcc ttccgtgtgg ttccggatac cttcatgtct tcacagcagg   16320
catctcactg actgggtcca tcaggatttg tgttctcccc tgagctatgt aatgcacagc   16380
tgccactgtt ggctgatggt tcaatgccca cacaaaccag cccccagata tgcttcctgg   16440
aagcccccct aagagtgaaa gacagctgag ggagtcctgc agagagattc cttgtcagat   16500
ttttaccttt cctttccgag tgtcctctgc ttcggtagaa tgccagcact ggggcaggtc   16560
aatgatctca ggctgcctca ctatgtagcc caggctagcc ccaaactaaa gattaccctg   16620
gattcctggc tgctctccat ctgctgccag gaaggaagcc ctgcctttag gttcatttcc   16680
cagtctaaac atctcagagt acccagagat caaggcttgc tcaggtcaga ccagaaagtt   16740
catttgctgg gctatcgggt tggaggacg tcttgggagg gagcacgctt tgctgacctg    16800
aggtttctaa ctctagtgga atccccgtgc tctgggctc atcgatgatg ctgggtttga    16860
accaacacag cgtgctagca tcttccaagt agatataaac cttgtgtcat tctcactcac   16920
agcggaggca gtgtggtttc tcagcatcgg gctagaagac tcggcacaaa ttgctggcac   16980
aggtgtctgt ctgtccgcca gtagccatgg ccagtgtgat gggtgagaat gcatgctgag   17040
atgatgacga gtctttcccg cactggtttc tgattgtgga gccacggtga gctcctactg   17100
ggaccccacg tgtgagactt atcttcccct gccaggtctt acttttaccc agtcactcac   17160
tcatttagca cagcagatac ctgcagagct gtcaagtgta agggcccagg gcccacagcc   17220
ataaaagata tgtgcacacc ctgtgcagct ctccaggaag aggccgcgcg gaaggtgtca   17280
ccatcacttt ctcggaacct gtcattgcat tgctatttat tttagttttc catcaaaatt   17340
catatctttt tcttgatttt taaaattgaa aaatccaaca attaatagat tttccaaatg   17400
gagaatactt acgtggctaa gaaagaatcc aagcaaatat agtaaaacta aacctccttt   17460
tctgggtcct tcggtcctca gaatcgcccc ccggcactgt tgctcccagg gattcagata   17520
cacacacaca cacacacaca cacacacaca cacacatgca cacatacaca tacacacaca   17580
cacatatata cacacataca cacacacaca tacacacaca cacatacaca cacatacaca   17640
cacatacaca catcacacaca catacacaca tacacacaca tacacacaca cacacacaga   17700
aagagaggga gagggagagg gagacggagg gagagagaga acctttttcca accttctctc   17760 aaatggaagc ggtctatgtc catgggacct cacacgggcc ctgtggtttt gccttgaagc   17820
gtttagtgtt ctgtcattca gattcacagt agttagctct gtcaagactg atcagagctc   17880
aataacgggc atcatactct cctccacttt caaaataagc caagaaaggt acatttcttg   17940
cgtcagtgga aaaaaaaata ccatctttac tatgcaaatt ttccacagtg ctcagggtcc   18000
agtaaaacga gttccacggg ctgtctaaca gtcagacggt ctctgcaagg gcctgctgta   18060
acccacaggt taacagatgg tctctgcaag agcctgctgt aacccatggg ctgtctaaca   18120
gtcagacggt ctctgcaagg gcctgctgta atccatgggc tgtctaacag tcagacggtc   18180
tctgcaaggg cctgctgtaa cccatgggct gtctaacagt cagacggtct ctgcaaaggt   18240
ctgctgtaac ccacgggctg tctaacagtc agacagtctc tgcaagggcc tgctgtaacc   18300
ttggactagg ctctctcctt agactagctc gtggtcaatc aggagactga accccagact   18360
tgcagaggga cccagcaagc ccaaagtctc ctagctcatt ctctggctag agggctccat   18420
cctccacaga agtccacaga agctgttgga ctggaggaca gatccccagc caaagagctt   18480
ttcctagctt tgacctcctc ttgggggtca gcactgctaa ctcttcacac tgggagaagg   18540
```

```
aggaagactg tggctaccct ggggtctccc acttatgacc tccacaggtc atattgctgc    18600
atggcatgtc ttcccgcacc tgggaagata atccactctg catacaagtc tctcaggata    18660
agcaacaatt cctgtttgct cgtctgtcaa ctatagatat atgaaatatc acattttagg    18720
ggatacttat ttatttactt atttatttgt aagacaaagt ctgaaatatc ccaaattgga    18780
ctgaagcttg ctgaagcttg ctgtgtagcc aagaatgagg taaccttgaa ctctgccagt    18840
tctcctgtct ccacctcctg attgctggga ttacacatgc atactaatat gcctggtttg    18900
tgtgacgctg aggtccaagc ccaaggcttc atgctcccta ggcaagtact cacaccgcag    18960
ttacatcctc agccctgaat gacacccgtt gggtccagcg agtgctgtca gccagcagtc    19020
tggtactgac cagcttgaac gctcctgagt aagatcacca caaaggccct ctgcagagaa    19080
aggggccccg tggcctgaag cagagactgc ctatgcaatc cccgcagcct gaactccatc    19140
acagcccgag gtggtccaga gcagacagcc tcagcccagt ccactagggg agagattggc    19200
tggctggctg gctgacatgc aaattcacag acaggcaatg caggaagaag ccatggctgg    19260
gtgggtgggc tgcggtgaga ccattgtgag ctgggtgcgc tgggtgtgga aactccctgt    19320
taaaacccgt gagcttttgct ttccattgca atggggaagg aggcaaaggc agccaggaag    19380
tgcactctga gatgacttta gacttctgaa gggtctgtct gtggtttcaa gaggcagagg    19440
aggaagccca gagcagcttg acagagtggc caaccaacac atcctgcctg gagcgtgagg    19500
ggaaggggac aggtgttatt acccaacttg tggggaaaga atagggatag gctaggggtg    19560
agaatatccc aatagatgag ccactgaaag caagagcagc aggctggctg agcccatcct    19620
ctgcctggtg tcagctgatg cttctctggc tacagagccc atgctacaac aatgcttcct    19680
ttccacctag agctgccaga tggccaaccc agtgcgattg ggatggagga actttccaca    19740
cagaattaac cctgacaaaa tcctgggtac tatgagacaa gagtgtaggg actacactgg    19800 ttatttttcct cacaccagtg accaaattcc aggctagaag caactaagga tgaaagaagt    19860
tacagcttct tctatgatag cctgggctga ggctgaggct gaggctctgg accacctcgg    19920
gccatgatgg aggtcaggct gcaggacaag catagcagtc tttgcttcag gctgcaggac    19980
cttctttttt ttttaattag gtattttctt catttacatt tcaaatgcta tcccaaaagt    20040
ccccccgtac tgcccccccc cattccccta cccacccact cccacttctt ggccctggcg    20100
ttcccctgta ctgaggcata taagtttac aagaccaagg ggcctctctt cccaatgatg    20160
gcctactaag ccatcttctg atacatatgc agctagagac atgaactcgg ggggtactgg    20220
ttagttcata ctgttgttcc acctataggg ttgcagttcc cttcagctcc ttgggtactt    20280
tctctagctc ctccattggg gaccctgtgt tccatccaat agctgactgt gagcatccac    20340
ttctgtgttt gctaggcccc agcatagtct cacaagagac agctatatca gggtcctttc    20400
agcaaaatct tgcttgtgta tgcaatggtg tcagtgtttg gaggctgatt atgggatgga    20460
tccccgggtg tggcagtctc tagatggtcc atccttttgt ctcagctcca aactttgtct    20520
ctgtaactcc ttccatgggt gttttgttcc caattctaag aaggggcaag gtgtccacac    20580
tttggtcttc cttcttcttg agtttcatgt gttttgcaaa ttgtatcttg tatcttgggt    20640
attctaaagg accttcttct ctgagcacct ctgctgtgat cttagtaagc tggtcagtaa    20700
gctgcctcac agctggtgtg tccttcctcc ccgaaaggaa gtggcatact gactggtggg    20760
atcactctgg tgtgaagtgg tgtgaagtcc tggcaggcgt gggaggcagc aggttcctat    20820
gtgcctgtaa atgggaaagc tcactcactc cttttctagg aggtttggga ccctaaccta    20880
```

```
tgcaatggtt ccatccacgt ttagagtgtt ttggttttgt ttttgttttta ccaagacaga    20940 atttcactgt gtagccctgg atggcctgta actcactctt gtagaccagg ctggcctcag    21000
actcagaaat ctgccagcct ctgcctacca agtgctaaga ttaaaggcgt gtactaccag    21060
gcccctggct acagtgggtc tccctacctt attaactcaa tatttaaaat ccctcccatg    21120
gggctggaga gatggctcag gagtttagag cattagctgc tcttcagag gacttaggtt    21180 caattcccag aacctacatg gtggctccca accatctgtt ttcaaaggtt ccaacaccct    21240
cttctggtct gggcaccagg cacaaccatg gtgctggcca gtcatgcaca catgtaaata    21300
aataaatctt tgtaaaaatt ataaataaat taggcccctc acagatgtgc tgagatgtgc    21360
atttccatgg agattctaaa ttccatcaaa gagctgagag atgcaaatgc tattctcaaa    21420
gaggaatcag tccgggtggc tcccatgtca gggtggcccc catgtcaggg tggcctacaa    21480
acacctgtaa gtccaactct aggggatcca ttgccccctt caggactcaa caaacacctg    21540
cactccatgt gccttcccac acacaaaccc acatgcacat aattttaaat aaaatcatat    21600
ttaaaaaaaa aagaaccagc gtagtatggg ctcatatctt tgatcccagc attcaggaga    21660
cagagacaga cagatctctg tgagttgcag accaacaggg ttccaagcaa gtcagggttt    21720
cacaatgaga ccctgttgca aaaataaaaa taaaaacaga aatgttttaa aagataggat    21780
gagtgaagac aaaatctagt tccaattgtt caccctttca gtgttttctc ccgcttgctg    21840
catgcagcca gtgagaaccg cgatcctcta agactcacgt gatctggttt gctgcataca    21900
gccagtgaga actgcgatcc tctaagactc acgtggacct gcttactgca tgcagccagt    21960
gagaactaca atcctttaag gctcacgtga tctggtttct ccttccctc caggacctca    22020 ccatgtccac ctccttccct gaactggatc tagagaattt tgagtatgac gattctgctg    22080
aggcctgtta tttgggcgac attgtggcct ttggaaccat cttcctgtcc gtcttctacg    22140
ccctcgtctt cacgttcggt ctggtgggaa atctgttggt ggtcctcgct ctcaccaaca    22200
gccggaagcc caagagcatc actgacatct acctcctgaa cctggccttg agcgacctgc    22260
tctttgtggc caccttgccc ttctggactc actacctcat cagccatgag ggcctccaca    22320
atgccatgtg caagctcacg actgccttct tcttcattgg cttctttggg gcatattct    22380 tcatcaccgt catcagcatc gaccggtacc ttgccatcgt cctggccgcc aactccatga    22440
acaaccggac agtgcagcac ggtgtcacca ttagtctggg cgtctgggcg gcggccatct    22500
tagtggcgtc accccagttc atgttcacaa agagaaagga caacgagtgt ctgggtgact    22560
accccgaggt cctgcaggaa atgtggcccg tgctccgcaa ctcggaagtc aacatcctgg    22620
gcttcgccct gccccttgctt atcatgagct tttgctactt ccgcatcatc cagacgctgt    22680
tttcctgcaa gaatcgcaag aaggccgag ccgtcagact catcctcctg gtggtctttg    22740
ccttcttcct cttctggaca ccatacaaca tcatgatttt cctggagact ctcaagttct    22800
acaacttctt ccccagttgt gacatgaaga gggacctgag gttggccctc agtgtgacgg    22860
agacagtggc gttcagccac tgttgcctca accccttat ctacgccttt gccggggaaa    22920
agttcagaag atacctggga cacctgtata ggaagtgcct ggccgtcctg tgcggtcatc    22980
ctgtccacac cggcttctcg ccagagtccc agaggagcag gcaggacagc attctgagca    23040
gtttcactca ctacacaagc gagggagatg ggtctctcct gctctgaagg ggtctccccg    23100
accctagctc cactaggaac ccagagttct tgcatcagat ttccctgccg ctcccctgc    23160 atcttatgtg caagaaatat ggaccagatg cctgcaaacc aaccccgtgg tgttttttg    23220 aaaaatttat gttcaatgtg tgaaaaacac acgtatctct tactgcaaat gttgaacatt    23280
```

```
ggggcttact ggtgacaaaa attctaacca gattagtgca attacaaagg ggtttggtga    23340
gtcctggttg catgatcatg tgataaagga caactaagtc ctcagactga gtggaaacca    23400
aggcttggct ccaatgtccc ctctctgacc ttcagatcct tcatagtgac agatcatcca    23460
ggttctatca tcagagaagg accacatctc tctgatttca aaattggtat tcctagggaa    23520
cacctccgtt ggccgagtgt gtcgggtgtc cattccttga ctaggtggtg ttattgaaat    23580
agaagggata cctaagatgc tgttggaatc tcaaggttag cggttgagag agacacatct    23640
ctcagaagct gggggggtggg agctactctg acagcaagaa ctgctgactc gccttaccat    23700
ggagctcatt caggctcccc ttcagtaact agcagtatct gttgctagct tctttaatct    23760
tctgttgaga atgtcctgaa ctctccaagg gttagaattt gggttactgc tcacagcatc    23820
aaattcaatc ccaaggccct gtcctccaag accaggaaga taggatgcag ttctaacaag    23880
agactccacg ctgactcctc attccacagg actccgtcca cccagttggc catgtccctt    23940
tttcttgtct tgacccacat ccctccactc ttctcagccc aggggaagaa atagaaagag    24000
ccatgcccca gagtgaaggg atcgattcat atcccaactc tgttgcttgc acattgggga    24060
gactggagcc aacagagctt cagtcccttc aatatagaaa ggggactgtg gtgccttcat    24120
ccattctagc atagtacctc agcaaggact ttagcattcc ctggatcagg aactgttacc    24180
ctgcctctga gaaatggagc tggtggagtg ggaggaacct gcaggctttg ctgcaggaca    24240
cagccagaca agaggagacc tattcctaca gcatccccca acatgtgcct agatctacaa    24300
agccattccc atgtcccgc tgtcaggca agacccaggc cacgagagca gcttgctttc    24360 tccctgacc ctgcaagcat cacgtaggat gtagccacaa gaatgtcttc atgcattcac    24420
tgactccggt ctcatttgca ggcttacatt gaaagttcca gttctgcaac ttgcttttta    24480
aaaaacactg gatttcaggg gctggagaga tggctcagtg gttaagagca cagtctgctc    24540
ctacagaggt cccaagttca attcccatgt catgtctgaa gacaaggaca gtgtagtcaa    24600
aaaaaacact ggaattcaaa tagctccctg ttcctgtgtt ggttgtgata accatttcag    24660
aagtctctcc cagcctgttg ctcacggcgg catgtctgat atctccttgg cagtctgtat    24720
gtttgtgtcg aggatgacag acagactgag tcatatcccc cacaggcata tccaacccct    24780
tgttattgca acaccatgct gtcatattca aaggtcacaa atgagaacct caaaattgag    24840
ttaccaaagt gggagcctgg agagatggct cagtggttaa tagcactggc tgctcttcca    24900
gaggtctggg gttggattcc cagcaagcat agtagcttac aatggtctat aatataactc    24960
tagttccagg tgacccaaca ccctcttcta atttgtgagg gtagcagaca tgtgcattgt    25020
gaacattcag gcaaacaccc atacatacaa aataagtaaa aagaaaaag aaggaagga    25080 atggagagag agaagagggg ggagagagag agggagaggg agaggagag ggagagggag    25140 ggagggagag ggagggaggg agggagggag ggagggaggg agggagggaa aggaaagaaa    25200
gaaagaaaga aggaaggaa ggaaggaagg aaggaaggaa ggaagaaaga aagaaagagg    25260
gagagagaga aagagagaaa gagagaaaga gaaagagaga aagagagaaa gagaaagaga    25320
gaaagagaga aagaagaaag aaagacagaa aattggtttt tcaagatagg ttctctctat    25380
gtagcctcgg ctgtcctgaa actctctgtg tagaccaggc tggcctagag ctcaaagaaa    25440
tccacctgcc tctgcctcct gagtactggg atcgaaggtc tgtggcacca tggcaggctt    25500
agtcaataaa tgtttatttt tcaaaagtat cctataatgt tttaagtaag tttatgcttt    25560
ggtgttggtc tgtatttccc gctgtctcgg gtcacatggt taagcgtgcc tagagtgtgt    25620
```

-continued

```
ctatcccact tgtaattctg tcaataaaca ttggtttcct tccagctctt ggcaagtacg    25680
agtctcaggg aactttaatc tgtgcacgtt tcctctccct gctcacttat ttccatcaga    25740
ttaattcttt gccatggggg tagctgggtc aaagggcaca ggaatgtttc agctctgttc    25800
tccagtacat acaattttat caaaaagcaa agcctggcca ggcatgctaa cctacatcct    25860
taacgacagc attcacgagg cagagggagg tatctctgcc agcccaagac cagcctggta    25920
acattgtaag actgaaaaaa aaacctagga aacaaaaaa ccaaaaaaac cctaaagctc     25980
tctagggaag gccagccgct cctcagcacc taaagcatcg ttgtcttgac caacctggaa    26040
gtaatggggc tgacaaggct gtcacaggca gccatcttgg cagggctgct ttgactgcca    26100
agctcagtaa gatccagtgc agcttgcttg aaaattttta atattgattg atccgttgtt    26160
tgtacatgta tgtgtgtgta tgcacatgta tgtatgttta tgcatgtgtg tatgtgtgtg    26220
tgtgtttatg catgtgtgta catgtgtgta tatatgcatg tgtatatatg tgtgcatgtg    26280
tatgtgtgca catgagtgta tgcatgtgca tgcacatgaa cacacatgaa gaaactcaga    26340
ggacaaattg cagaagtcag ggctcccttt ccaccacata ggtcccagga tcaaactccg    26400 gttgagggc ttggtggcaa ttgtctttac ctgatgaacc atctctccag gcccgcttta    26460
gtttttgcat acacatgacc ttcatttgat aatgacaatt tgttacaagt ctttacgaag    26520
cacatatcct agcgggctcc agagatgttt ccacagcagt gagaccacac ctctgttctc    26580
agaggttttg atttatttt tgagatagag tctcactttg tagaccaggc tgccctggaa    26640
ctcggaaatc tgcctgcctc ttcccctgga gtgttgggat taaaggtgtg cgccaccacc    26700
ctgggcttga tatctgtgga cagaaaaggc ctggctgtgt ttaacttgct tgctgtaaga    26760
cagagcagag gtaataagat ctgacccaag acttcaggga tatgagcttc tccaggagaa    26820
gcaggggctg tttgctagga ggcagggatg tggaattcgt gtgagagagc acgaggttcc    26880
ttcagtgtca gtccctcatt ccaactgatg agcctgagag ttgtcatcaa aggttaatct    26940
gttcctggac tccatgtag agaagaaaga cttctggcct gagaagcaaa catagggaag    27000
c                                                                    27001
```

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
tagtgcggac ctacccacga                                                20

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
gcacctttcc ctcggatggg                                                20

<210> SEQ ID NO 7
<211> LENGTH: 64
<212> TYPE: DNA
<213> ORGANISM: Artificial sequence
<220> FEATURE:
<223> OTHER INFORMATION: Synthetic oligonucleotide

```
<220> FEATURE:
<221> NAME/KEY: misc_feature
<222> LOCATION: (64)..(64)
<223> OTHER INFORMATION: n is a, c, g, or t

<400> SEQUENCE: 7
gatcgtcgga ctgtagaact ctcaagcaga agacggcata cgattttttt tttttttttt     60 tttn                                                                  64

<210> SEQ ID NO 8
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 8
caagcagaag acggcata                                                   18

<210> SEQ ID NO 9
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 9
aatgatacgg cgaccaccga caggttcaga gttctacagt ccgacg                    46

<210> SEQ ID NO 10
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 10
cgacaggttc agagttctac agtccgacga tc                                   32

<210> SEQ ID NO 11
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 11
cagagucaga gagucagaga gagau                                           25

<210> SEQ ID NO 12
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 12
aucucucucu gacucucuga cucug                                           25

<210> SEQ ID NO 13
<211> LENGTH: 25
<212> TYPE: RNA
<213> ORGANISM: Artificial sequence
<220> FEATURE:
<223> OTHER INFORMATION: Synthetic oligonucleotide
```

-continued

<400> SEQUENCE: 13
gaguuuggac cugugaccuu ccuaa                                          25

<210> SEQ ID NO 14
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 14
uuaggaaggu cacaggucca aacuc                                          25

<210> SEQ ID NO 15
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 15
aaucuccugg gaggaugaag cguuu                                          25

<210> SEQ ID NO 16
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 16
aacagcuuca uccucccagg agauu                                          25

<210> SEQ ID NO 17
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 17
accacuguuu cugacugcuu ucuca                                          25

<210> SEQ ID NO 18
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 18
ugagaaagca gucagaaaca guggu                                          25

<210> SEQ ID NO 19
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 19
ggauugagag ugaccaggac auuua                                          25

<210> SEQ ID NO 20
<211> LENGTH: 25

```
<212> TYPE: RNA
<213> ORGANISM: Artificial sequence
<220> FEATURE:
<223> OTHER INFORMATION: Synthetic oligonucleotide

<400> SEQUENCE: 20
uaaauguccu ggucacucuc aaucc                                           25

<210> SEQ ID NO 21
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 21
cgcccagccu aauguaguag cuuua                                           25

<210> SEQ ID NO 22
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 22
uaaaguacua caauuaggcu gggcg                                           25

<210> SEQ ID NO 23
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 23
gcaaauucuu ucaugacaa                                                  19

<210> SEQ ID NO 24
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 24
uugucaugaa agaauuugc                                                  19

<210> SEQ ID NO 25
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 25
gcaaagaugg auagagaua                                                  19

<210> SEQ ID NO 26
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 26
```

-continued uaucucuauc caucuuugc                                                19

<210> SEQ ID NO 27
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 27
gcacauaccu cauuagaga                                                19

<210> SEQ ID NO 28
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 28
ucucuaauga gguaugugc                                                19

<210> SEQ ID NO 29
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 29
gguauuaaua gcucugaaa                                                19

<210> SEQ ID NO 30
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 30
uuucagagcu auuaauacc                                                19

<210> SEQ ID NO 31
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 31
gggagagggu cuacaauua                                                19

<210> SEQ ID NO 32
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 32
uaauugucga cccucuccc                                                19

<210> SEQ ID NO 33
<211> LENGTH: 19
<212> TYPE: RNA
<213> ORGANISM: Artificial sequence

```
<220> FEATURE:
<223> OTHER INFORMATION: Synthetic oligonucleotide

<400> SEQUENCE: 33
ggccagaucu ccugugaua                                                    19

<210> SEQ ID NO 34
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 34
uaucacagga gaucuggcc                                                    19

<210> SEQ ID NO 35
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 35
gcuccauucu gcugcucaa                                                    19

<210> SEQ ID NO 36
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 36
uugagcagca gaauggagc                                                    19

<210> SEQ ID NO 37
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 37
cuaacgugac agugacaua                                                    19

<210> SEQ ID NO 38
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 38
uaugucacug ucacguuag                                                    19

<210> SEQ ID NO 39
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 39
gcaaaaggua ggaggguuu                                                    19
```

```
<210> SEQ ID NO 40
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 40
aaacccuccu accuuuugc                                                   19

<210> SEQ ID NO 41
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 41
ggagaugaau ugauagaga                                                   19

<210> SEQ ID NO 42
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 42
ucucuaucaa uucaucucc                                                   19

<210> SEQ ID NO 43
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 43
cagaagagcu auuugguau                                                   19

<210> SEQ ID NO 44
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 44
auaccaaaua gcucuucug                                                   19

<210> SEQ ID NO 45
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 45
gaguggacuu cacaagaaa                                                   19

<210> SEQ ID NO 46
<211> LENGTH: 19
<212> TYPE: RNA
<213> ORGANISM: Artificial sequence
<220> FEATURE:
<223> OTHER INFORMATION: Synthetic oligonucleotide
```

```
<400> SEQUENCE: 46
uuucuuguga aguccacuc                                               19

<210> SEQ ID NO 47
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 47
agagaagaau gaaggugaa                                               19

<210> SEQ ID NO 48
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 48
uucaccuuca uucuucucu                                               19

<210> SEQ ID NO 49
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 49
ccacagguga gcagaaauu                                               19

<210> SEQ ID NO 50
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 50
aauuucugcu caccugugg                                               19

<210> SEQ ID NO 51
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 51
ccuaauuccc agaagcaga                                               19

<210> SEQ ID NO 52
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 52
ucugcuucug ggaauuagg                                               19

<210> SEQ ID NO 53
```

```
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 53
cgaaauggcc uaaagauga                                                  19

<210> SEQ ID NO 54
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 54
ucaucuuuag gccauuucg                                                  19

<210> SEQ ID NO 55
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 55
acacaaaggu ggaaggaaa                                                  19

<210> SEQ ID NO 56
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 56
uuuccuucca ccuugugu                                                   19

<210> SEQ ID NO 57
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 57
ggaagaaccu gcagagaug                                                  19

<210> SEQ ID NO 58
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 58
caucucugca gguucuucc                                                  19

<210> SEQ ID NO 59
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 59
```
cacgtctata caccac                                                          16

<210> SEQ ID NO 60
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 60
gaattaacgc ctgagg                                                          16

<210> SEQ ID NO 61
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 61
gaactgacaa aggtgg                                                          16

<210> SEQ ID NO 62
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 62
atctccccac tcaagg                                                          16

<210> SEQ ID NO 63
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 63
catttttctg ctgacc                                                          16

<210> SEQ ID NO 64
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 64
acaagacaga ggcaga                                                          16

<210> SEQ ID NO 65
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 65
tcagttggag gacagt                                                          16

<210> SEQ ID NO 66
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 66
gaaggagcag gtgaaa                                                         16

<210> SEQ ID NO 67
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 67
ggtatttccg cttcac                                                         16

<210> SEQ ID NO 68
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 68
aggataccag gacaca                                                         16

<210> SEQ ID NO 69
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 69
tgataaaagc agggtc                                                         16

<210> SEQ ID NO 70
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 70
tcagttccca gcattctcat c                                                   21

<210> SEQ ID NO 71
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 71
ttgagccttg gagacagaaa g                                                   21

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
tccaaagcat cccattcctg                                                     20
```

<210> SEQ ID NO 73
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 73
tgagcaaaac aagacaaacc g                                             21

<210> SEQ ID NO 74
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 74
ttatgttgct cttgatagac tccc                                          24

<210> SEQ ID NO 75
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 75
gctaggtgct gtctgagatt c                                             21

<210> SEQ ID NO 76
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 76
ttcaagcaaa gattatagcc atgtg                                         25

<210> SEQ ID NO 77
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 77
atccagtgca gagtaacatc ag                                            22

<210> SEQ ID NO 78
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 78
agatgcctct gcatactggt t                                             21

<210> SEQ ID NO 79
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 79
cagaccatat tgggccacag                                                    20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
ccacagcaga aaaccactga                                                    20

<210> SEQ ID NO 81
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 81
ttccctctgc actgactcct                                                    20

<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
cgtcttttcc cactgacaca                                                    20

<210> SEQ ID NO 83
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 83
cccctcccca gaagaaaata                                                    20

<210> SEQ ID NO 84
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 84
ctgaggaaca caagactagc c                                                  21

<210> SEQ ID NO 85
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 85
actggactca ttttgggaca tc                                                 22

```
<210> SEQ ID NO 86
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 86
attgtgcatg gctcttaccc                                               20

<210> SEQ ID NO 87
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 87
cttggtgcat gtgagcttgt                                               20

<210> SEQ ID NO 88
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 88
agcttctggt tccaaggtca                                               20

<210> SEQ ID NO 89
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 89
catgtgctgt tgttgctgtg                                               20

<210> SEQ ID NO 90
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 90
tgaaagggaa gacgcagatg                                               20

<210> SEQ ID NO 91
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 91
ttgtatcctt tgactgggca g                                             21

<210> SEQ ID NO 92
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 92
aaagaaggca ggggaacaat                                               20

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 93
cacttgggca atccagaaat                                               20

<210> SEQ ID NO 94
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 94
tcacctgtgg aaagagacaa c                                             21

<210> SEQ ID NO 95
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 95 agaaccttt gctccctagt g                                              21

<210> SEQ ID NO 96
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 96
ttaaacgagc ctggagttgg                                               20

<210> SEQ ID NO 97
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 97
aaattcctca gagcccagtg                                               20

<210> SEQ ID NO 98
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 98
ggctcagaga ggccaaaa                                                 18

<210> SEQ ID NO 99
<211> LENGTH: 24
```

```
<212> TYPE: DNA
<213> ORGANISM: Artificial sequence
<220> FEATURE:
<223> OTHER INFORMATION: Synthetic oligonucleotide

<400> SEQUENCE: 99
tggaccctat catctccttt aact                                        24

<210> SEQ ID NO 100
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 100
ggaaaggaat tgctggatca                                             20

<210> SEQ ID NO 101
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 101
gtgcaaccac ttgggaaact                                             20

<210> SEQ ID NO 102
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 102
cagagatgag gaaaggtttg c                                           21

<210> SEQ ID NO 103
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 103
atctgcttca cggtctcatg                                             20

<210> SEQ ID NO 104
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 104
agtagctgtc aaatggcctt c                                           21

<210> SEQ ID NO 105
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 105
```
ttagttcggc tttgagggtg                                              20

<210> SEQ ID NO 106
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 106
ggggacctgt ttttcctgtt                                              20

<210> SEQ ID NO 107
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 107
gacttggatc tggacctgga                                              20

<210> SEQ ID NO 108
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 108
tctgtctgcc aacaagcagt                                              20

<210> SEQ ID NO 109
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 109
gcactgtagc gagactggag                                              20

<210> SEQ ID NO 110
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 110
tcctgctgtg caaagtgttc                                              20

<210> SEQ ID NO 111
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 111
aaatccatcg ggtatctgga                                              20

<210> SEQ ID NO 112
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 112
tgccaagaga ctagggcagt                                               20

<210> SEQ ID NO 113
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 113
gaatacgaag ggtgggatca                                               20

<210> SEQ ID NO 114
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 114
catcacaggg aaccagacct                                               20

<210> SEQ ID NO 115
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 115
caccccgaag agaccataga                                               20

<210> SEQ ID NO 116
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 116
tcaggaacct ggctatggag                                               20

<210> SEQ ID NO 117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 117
ggcaggagta gggacggtat                                               20

<210> SEQ ID NO 118
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 118
gccagaagat gcacacttga                                               20
```

<210> SEQ ID NO 119
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 119
caagctctga gcctctgctt					20

<210> SEQ ID NO 120
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 120
caccatggag aacaaggtga					20

<210> SEQ ID NO 121
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 121
tgacaccagg aaaaccacaa					20

<210> SEQ ID NO 122
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 122
ggcaggacca gcttctga					18

<210> SEQ ID NO 123
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 123
ctgttcccac caccttgg					18

<210> SEQ ID NO 124
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 124
tccattgcca ccccca					16

<210> SEQ ID NO 125
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 125
tcctccattg ccaccc                                                    16

<210> SEQ ID NO 126
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 126
acttcctcca ttgcca                                                    16

<210> SEQ ID NO 127
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 127
ccaacttcct ccattg                                                    16

<210> SEQ ID NO 128
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 128
acacttctct ccctac                                                    16

<210> SEQ ID NO 129
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 129
ggcttggaat ccatca                                                    16

<210> SEQ ID NO 130
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 130
caactgcgga gggagg                                                    16

<210> SEQ ID NO 131
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 131
taccaactgc ggaggg                                                    16

<210> SEQ ID NO 132
```

-continued

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 132
tcttaccaac tgcgga                                                     16

<210> SEQ ID NO 133
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 133
ctttcttacc aactgc                                                     16

<210> SEQ ID NO 134
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 134
gttctttctt accaac                                                     16

<210> SEQ ID NO 135
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 135
gattgctgct ggttct                                                     16

<210> SEQ ID NO 136
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 136
caggattgct gctggt                                                     16

<210> SEQ ID NO 137
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 137
cttcaggatt gctgct                                                     16

<210> SEQ ID NO 138
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 138
```
cgccttcagg attgct                                                    16

<210> SEQ ID NO 139
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 139
cacttcactc gccttcagga tt                                             22

<210> SEQ ID NO 140
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 140
actcgccttc aggatt                                                    16

<210> SEQ ID NO 141
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 141
ttcactcgcc ttcagg                                                    16

<210> SEQ ID NO 142
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 142
cacttcactc gccttc                                                    16

<210> SEQ ID NO 143
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 143
taccacttca ctcgcc                                                    16

<210> SEQ ID NO 144
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 144
gggtaccact tcactc                                                    16

<210> SEQ ID NO 145
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 145
agtgggtacc acttca                                                       16

<210> SEQ ID NO 146
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 146
agcagtgggt accact                                                       16

<210> SEQ ID NO 147
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 147
gtaagcagtg ggtacc                                                       16

<210> SEQ ID NO 148
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 148
agtgggtaag cagtgg                                                       16

<210> SEQ ID NO 149
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 149
aacagtgggt aagcag                                                       16

<210> SEQ ID NO 150
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 150
ctggaacagt gggtaa                                                       16

<210> SEQ ID NO 151
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 151
tgcctggaac agtggg                                                       16
```

<210> SEQ ID NO 152
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 152
aggtgcctgg aacagt                                              16

<210> SEQ ID NO 153
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 153
ttacagaggt gcctgg                                              16

<210> SEQ ID NO 154
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 154
ctgttacaga ggtgcc                                              16

<210> SEQ ID NO 155
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 155
ggcctgttac agaggt                                              16

<210> SEQ ID NO 156
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 156
gtgggcctgt tacaga                                              16

<210> SEQ ID NO 157
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 157
catgtgggcc tgttac                                              16

<210> SEQ ID NO 158
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 158
tcccatgtgg gcctgt                                                                16

<210> SEQ ID NO 159
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 159
gtttcccatg tgggcc                                                                16

<210> SEQ ID NO 160
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 160
agtgtttccc atgtgg                                                                16

<210> SEQ ID NO 161
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 161
gctaataaca gtgttt                                                                16

<210> SEQ ID NO 162
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 162
agtgctaata acagtg                                                                16

<210> SEQ ID NO 163
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 163
acaagtgcta ataaca                                                                16

<210> SEQ ID NO 164
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 164
catttccccc atcttaaaaa caag                                                       24

```
<210> SEQ ID NO 165
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 165
tttcccccat cttaaa                                                         16

<210> SEQ ID NO 166
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 166
cctaccattt cccca                                                          16

<210> SEQ ID NO 167
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 167
caacctacca tttccc                                                         16

<210> SEQ ID NO 168
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 168
acacaaccta ccattt                                                         16

<210> SEQ ID NO 169
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 169
tcgacacaac ctacca                                                         16

<210> SEQ ID NO 170
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 170
ctatcgacac aaccta                                                         16

<210> SEQ ID NO 171
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 171
cagctatcga cacaac                                                         16

<210> SEQ ID NO 172
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 172
ccccagctat cgacac                                                         16

<210> SEQ ID NO 173
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 173
tgaccccagc tatcga                                                         16

<210> SEQ ID NO 174
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 174
gtgtgacccc agctat                                                         16

<210> SEQ ID NO 175
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 175
ctcattgtgt gacccc                                                         16

<210> SEQ ID NO 176
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 176
cagctcattg tgtgac                                                         16

<210> SEQ ID NO 177
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 177
gcttcagctc attgtg                                                         16

<210> SEQ ID NO 178
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 178
atccaagctt cagctc                                                       16

<210> SEQ ID NO 179
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 179
gccgaaatcc aagctt                                                       16

<210> SEQ ID NO 180
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 180
actgccgaaa tccaag                                                       16

<210> SEQ ID NO 181
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 181
tggactgccg aaatcc                                                       16

<210> SEQ ID NO 182
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 182
gattggactg ccgaaa                                                       16

<210> SEQ ID NO 183
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 183
tgggattgga ctgccg                                                       16

<210> SEQ ID NO 184
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 184
```
ctctgggatt ggactg                                              16

<210> SEQ ID NO 185
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 185
ccactctggg attgga                                              16

<210> SEQ ID NO 186
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 186
gctcccactc tgggat                                              16

<210> SEQ ID NO 187
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 187
tgagtaggcc aatggg                                              16

<210> SEQ ID NO 188
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 188
gagtgagtag gccaat                                              16

<210> SEQ ID NO 189
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 189
gcagagtgag taggcc                                              16

<210> SEQ ID NO 190
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 190
gaggccagga cttggc                                              16

<210> SEQ ID NO 191
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 191
aagttcagca gaggcc                                                        16

<210> SEQ ID NO 192
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 192
aacaagttca gcagag                                                        16

<210> SEQ ID NO 193
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 193
agatgtggaa acaagt                                                        16

<210> SEQ ID NO 194
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 194
attctaattt ccttcg                                                        16

<210> SEQ ID NO 195
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 195
catctattct aatttc                                                        16

<210> SEQ ID NO 196
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 196
ccccatctat tctaat                                                        16

<210> SEQ ID NO 197
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 197
tgtccccatc tattct                                                        16
```

```
<210> SEQ ID NO 198
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 198
aggtgtcccc atctat                                                     16

<210> SEQ ID NO 199
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 199
tggaggtgtc cccatc                                                     16

<210> SEQ ID NO 200
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 200
cacacatgga ggtgtc                                                     16

<210> SEQ ID NO 201
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 201
gagtcaacag aaatac                                                     16

<210> SEQ ID NO 202
<211> LENGTH: 457
<212> TYPE: DNA
<213> ORGANISM: Mus musculus

<400> SEQUENCE: 202
cagggtgtat gtgtgggggt ggcaatggag gaagttgggg gtagggagag aagtgttctt      60
gctttgatgg attccaagcc ctgggttctc cctccctccg cagttggtaa gaaagaacca     120
gcagcaatcc tgaaggcgag tgaagtggta cccactgctt acccactgtt ccaggcacct     180
ctgtaacagg cccacatggg aaacactgtt attagcactt gtttttaaga tgggggaaat     240
ggtaggttgt gtcgatagct ggggtcacac aatgagctga agcttggatt tcggcagtcc     300
aatcccagag tgggagcccc cattggccta ctcactctgc ctgccaagtc ctggcctctg     360
ctgaacttgt ttccacatct gcatgacgaa ggaaattaga atagatgggg acacctccat     420
gtgtggtgtt tgtatttctg ttgactcttt tttttct                              457

<210> SEQ ID NO 203
<211> LENGTH: 3185
<212> TYPE: DNA
<213> ORGANISM: Mus musculus

<400> SEQUENCE: 203
```

```
ctcaccatga gtccctggca gcccctgctc ctggctctcc tggctttcgg ctgcagctct      60
gctgccccct accagcgcca gccgactttt gtggtcttcc ccaaagacct gaaaacctcc     120
aacctcacgg acacccagct ggcagaggca tacttgtacc gctatggtta cacccgggcc     180
gcccagatga tgggagagaa gcagtctcta cggccggctt tgctgatgct tcagaagcag     240
ctctccctgc cccagactgg tgagctggac agccagacac taaaggccat tcgaacacca     300
cgctgtggtg tcccagacgt gggtcgattc caaaccttca aaggcctcaa gtgggaccat     360
cataacatca catactggat ccaaaactac tctgaagact gccgcgaga catgatcgat      420
gacgccttcg cgcgcgcctt cgcggtgtgg ggcgaggtgg caccctcac cttcacccgc      480
gtgtacggac ccgaagcgga cattgtcatc cagtttggtg tcgcggagca cggagacggg     540
tatcccttcg acggcaagga cggccttctg cacacgcct ttcccctgg cgccggcgtt       600
cagggagatg cccatttcga cgacgacgag ttgtggtcgc tgggcaaagg cgtcgtgatc     660
cccacttact atggaaactc aaatggtgcc ccatgtcact ttcccttcac cttcgaggga    720
cgctcctatt cggcctgcac cacagacggc cgcaacgacg gcacgccttg gtgtagcaca    780
acagctgact acgataagga cggcaaattt ggtttctgcc ctagtgagag actctacacg    840
gagcacggca acggagaagg caaaccctgt gtgttcccgt tcatctttga gggccgctcc    900
tactctgcct gcaccactaa aggccgctcg gatggttacc gctggtgcgc caccacagcc    960
aactatgacc aggataaact gtatggcttc tgccctaccc gagtggacgc gaccgtagtt   1020
gggggcaact cggcaggaga gctgtgcgtc ttccccttcg tcttcctggg caagcagtac   1080
tcttcctgta ccagcgacgg ccgcagggat gggcgcctct ggtgtgcgac cacatcgaac   1140
ttcgacactg acaagaagtg gggtttctgt ccagaccaag ggtacagcct gttcctggtg   1200
gcagcgcacg agttcggcca tgcactgggc ttagatcatt ccagcgtgcc ggaagcgctc   1260
atgtacccgc tgtatagcta cctcgagggc ttccctctga ataaagacga catagacggc   1320
atccagtatc tgtatggtcg tggctctaag cctgacccaa ggcctccagc caccaccaca   1380
actgaaccac agccgacagc acctcccact atgtgtccca ctatacctcc cacggcctat   1440
cccacagtgg gccccacggt tggccctaca ggcgccccct cacctggccc cacaagcagc   1500
ccgtcacctg gccctacagg cgcccccctca cctggcccta cagcgccccc tactgcgggc   1560
tcttctgagg cctctacaga gtctttgagt ccggcagaca tccttgcaa tgtggatgtt    1620
tttgatgcta ttgctgagat ccagggcgct ctgcatttct tcaaggacgg ttggtactgg   1680
aagttcctga atcatagagg aagcccatta cagggcccct tccttactgc ccgcacgtgg   1740
ccagccctgc ctgcaacgct ggactccgcc tttgaggatc cgcagaccaa gagggttttc   1800
ttcttctctg gacgtcaaat gtgggtgtac acaggcaaga ccgtgctggg ccccaggagt   1860
ctggataagt tgggtctagg cccagaggta acccacgtca gcgggcttct cccgcgtcgt   1920
ctcgggaagg ctctgctgtt cagcaagggg cgtgtctgga gattcgactt gaagtctcag   1980
aaggtggatc cccagagcgt cattcgcgtg gataaggagt tctctggtgt gccctggaac   2040
tcacacgaca tcttccagta ccaagacaaa gcctatttct gccatggcaa attcttctgg   2100
cgtgtgagtt ccaaaatga ggtgaacaag gtggaccatg aggtgaacca ggtggacgac   2160
gtgggctacg tgacctacga cctcctgcag tgcccttgaa ctagggctcc ttctttgctt   2220
caaccgtgca gtgcaagtct ctagagacca ccaccaccac caccacacac aaacccccatc  2280
cgagggaaag gtgctagctg gccaggtaca gactggtgat ctcttctaga gactgggaag   2340
```

```
gagtggaggc aggcagggct ctctctgccc accgtccttt cttgttggac tgtttctaat    2400
aaacacggat ccccaacctt ttccagctac tttagtcaat cagcttatct gtagttgcag    2460
atgcatccga gcaagaagac aactttgtag ggtggattct gaccttttat ttttgtgtgg    2520
cgtctgagaa ttgaatcagc tggcttttgt gacaggcact tcaccggcta aaccacctct    2580
cccgactcca gcccttttat ttattatgta tgaggttatg ttcacatgca tgtatttaac    2640
ccacagaatg cttactgtgt gtcgggcgcg gctccaaccg ctgcataaat attaaggtat    2700
tcagttgccc ctactggaag gtattatgta actatttctc tcttacattg gagaacacca    2760
ccgagctatc cactcatcaa acatttattg agagcatccc tagggagcca ggctctctac    2820
tgggcgttag ggacagaaat gttggttctt ccttcaagga ttgctcagag attctccgtg    2880
tcctgtaaat ctgctgaaac cagacccag actcctctct ctcccgagag tccaactcac    2940
tcactgtggt tgctggcagc tgcagcatgc gtatacagca tgtgtgctag agaggtagag    3000
ggggtctgtg cgttatggtt caggtcagac tgtgtcctcc aggtgagatg acccctcagc    3060
tggaactgat ccaggaagga taaccaagtg tcttcctggc agtcttttt aaataaatga     3120 ataaatgaat atttacttaa aaaaaaaaaa aaaaaaaaa aaaaaaaaa aaaaaaaaaa      3180 aaaaa                                                                3185
```

MODULATION OF ENHANCER RNA MEDIATED GENE EXPRESSION

CROSS REFERENCED TO RELATED APPLICATIONS

This application is a U.S. National Phase filing under 35 U.S.C. §371 claiming priority to International Serial No. PCT/US2013/042163 filed May 22, 2013, which claims priority to U.S. Provisional Application 61/650,426, filed May 22, 2012, each of which is incorporated herein by reference in its entirety.

SEQUENCE LISTING

The present application is being filed along with a Sequence Listing in electronic format. The Sequence Listing is provided as a file entitled BIOL0202USASEQ_ST25.txt created Nov. 20, 2014, which is approximately 80 KB in size. The information in the electronic format of the sequence listing is incorporated herein by reference in its entirety.

FIELD

Certain embodiments are directed to methods and compounds for inhibiting gene expression by inhibiting enhancer RNAs (eRNAs). Such methods and compounds are useful for reducing expression of certain genes, many of which are associated with a variety of diseases and disorders.

BACKGROUND

Recent high-throughput transcriptomic analyses have revealed that eukaryotic genomes transcribe up to 90% of the genomic DNA. (The ENCODE Project Consortium. The ENCODE (ENCyclopedia of DNA Elements) Project. Science 2004; 306:636-640). Only 1-2% of these transcripts encode for proteins, whereas the vast majority are transcribed as non-coding RNAs (ncRNAs).

The majority of the non-protein-coding transcripts belong to the group of lncRNAs, which are considered as >200 nucleotides in length. Most lncRNAs are characterized by nuclear localization, low expression, low level of sequence conservation and are composed of both poly A+ and poly A− transcripts, (Kapranov P, et al., "RNA maps reveal new RNA classes and a possible function for pervasive transcription." Science 2007316:1484-1488) (Wu Q, et al., "Poly A− transcripts expressed in HeLa cells," PLoS One 2008; 3:02803).

One subgroup of lncRNAs, termed large intergenic non-coding RNAs (lincRNAs), was described based on distinctive chromatin signature that marks actively transcribed genes. (Khalil A M et al., "Many human large intergenic noncoding RNAs associate with chromatin-modifying complexes and affect gene expression." Proc Natl Acad Sci USA 2009; 106:11667-11672) (Guttman M et al., "Chromatin signature reveals over a thousand highly conserved large non-coding RNAs in mammals." Nature 2009; 458:223-227). LincRNAs are marked by trimethylation of lysine 4 of histone H3 (H3K4me3) at their promoter and trimethylation of lysine 36 of histone H3 (H3K36me3) along the transcribed region.

Another subgroup of lncRNAs, termed enhancer RNAs (eRNAs), was recently reported to be transcribed from genomic enhancer regions. (Kim T K et al., "Widespread transcription at neuronal activity-regulated enhancers." Nature 2010; 465:182-187) (De Santa F et al., "A large fraction of extragenic RNA pot II transcription sites overlap enhancers," PLoS Biol 2010; 8:e1000384). Distinct from eRNAs, another subgroup of lncRNAs, termed ncRNA-activators (ncRNA-a) was classified as mono-directional, polyadenylated, and having a H3K4 trimethylation chromatin signature. (Orom U A, Derrien T, Beringer M, Gumireddy K, Giardini A, Bussotti G et al. Long noncoding RNAs with enhancer-like function in human cells. Cell 2010; 143:46-58.)

SUMMARY

Several embodiments provided herein relate to the discovery that eRNAs are functional molecules that stimulate gene expression and can be targeted for inhibition to modulate gene expression, Prior to the present discovery manifest in several embodiments described herein, it was unknown and uncertain in the field whether eRNAs are functional molecules or merely products of "transcriptional noise" arising from PolII mediated transcription of genomic sequences adjacent to coding genes. (Struhl K, "Transcriptional noise and the fidelity of initiation by RNA polymerase II." Nat Struct Mol Biol 2007 14: 103-105) (Ponting C P et al., "Evolution and functions of long noncoding RNAs." Cell 2009 136: 629-641). eRNAs are widely considered just a byproduct of a transcriptional "ripple effect," a type of transcriptional noise in which PolII causes a wave of transcription from genes into adjacent sequences including intergenic regions. Ebisuya M et al., "Ripples from neighbouring transcription." Nat Cell Biol 2008 10: 1106-1113.

The present embodiments demonstrate eRNAs are functional molecules and targeting them for inhibition modulates gene expression. Certain embodiments are directed to methods and compounds for inhibiting gene expression by inhibiting enhancer RNAs (eRNA). In certain several embodiments, a method of inhibiting gene expression in a cell includes contacting the cell with a specific inhibitor of an enhancer RNA (eRNA), thereby inhibiting expression of one or more genes in the cell. In certain aspects, the eRNA is transcribed from a genomic enhancer sequence or region; the genomic enhancer sequence or region comprises any one of the genomic coordinates identified in Mega-Tables 1-9 filed in U.S. Provisional Application No. 61/650,426 in electronic format on May 22, 2012; the eRNA transcription is initiated from a RNA polymerase II (PolII) binding site and is capable of elongating bidirectionally; the eRNA is capable of enhancing transcription of the one or more genes; the genomic enhancer sequence or region has a higher level of monomethylated lysine 4 of histone 3 (H3K4me1) than trimethylated lysine 4 of histone 3 (H3K4me3); the genomic enhancer sequence or region is enriched for bound RNA polymerase II (PolII); the genomic enhancer sequence or region is enriched for bound transcriptional co-activator p300/CBP; the genomic enhancer sequence or region is enriched for bound Rev-Erbα or Rev-Erbβ; the genomic enhancer sequence or region is enriched for bound estrogen receptor, such as estradiol-bound estrogen receptor; eRNA has a relatively short half-life compared to mRNA, such as less than about 10-30 minutes; the transcriptional start site of the one or more genes is located on a chromosome at least about 1 kilobase (kb) from the genomic enhancer sequence or region; the eRNA is not polyadenylated or has a shorter polyA tail than mRNA or ncRNA-a; the cell is a hematopoietic cell, such as a monocyte or macrophage; the cell is a neuron; the cell is a breast cell; the cell is a cancer cell; and/or the cell contacted with a specific inhibitor of an enhancer RNA (eRNA) is in a subject. In several embodiments, the eRNA enhances transcription of matrix metalloproteinase 9 (MMP9), chemokine receptor CX3 CR1, CA12, FOXC1, GREB1, P2RY2, SMAD7, PGR, SIAH2, NRIP1, TFF1, or KCNK5.

In several embodiments, compounds, which can be used in the aforementioned methods of inhibiting gene expression in a cell, comprise a specific inhibitor of an enhancer RNA (eRNA). In certain aspects, the specific inhibitor of an enhancer RNA (eRNA) is an antisense compound. In several aspects, the antisense compound is single-stranded; double-stranded; modified; 8 to 80 nucleosides in length; 12 to 30 nucleosides in length; 16 nucleosides in length; includes at least one modified sugar, such as a bicyclic sugar, a 2'-O-methoxyethyl group, and/or a 4'-CH(CH$_3$)—O-2' group; includes at least one modified internucleoside linkage, such as a phosphorothioate internucleoside linkage; and/or includes at least one modified nucleobase, such as a 5-methylcytosine.

In further aspects, the antisense compound includes a gap segment consisting of linked deoxynucleosides; a 5' wing segment consisting of linked nucleosides; and a 3' wing segment consisting of linked nucleosides, wherein the gap segment is positioned between the 5' wing segment and the 3' wing segment and wherein each nucleoside of each wing segment comprises a modified sugar.

In another aspect, the antisense compound includes a gap segment consisting of ten linked deoxynucleosides; a 5' wing segment consisting of 3 linked nucleosides; and a 3' wing segment consisting of 3 linked nucleosides; wherein the gap segment is positioned between the 5' wing segment and the 3' wing segment, wherein each nucleoside of each wing segment comprises a 2'-O-methoxyethyl sugar or a constrained ethyl sugar; and wherein each internucleoside linkage is a phosphorothioate linkage.

In certain aspects, the 3 linked nucleosides of the 5' wing segment comprise a 2'-O-methoxyethyl sugar, a constrained ethyl sugar, and a constrained ethyl sugar in the 5' to 3' direction, and the 3 linked nucleosides of the 3' wing segment comprise a constrained ethyl sugar, a constrained ethyl sugar, and a 2'-O-methoxyethyl sugar in the 5' to 3' direction.

In further aspects, the antisense oligonucleotide comprises a gap segment of ten 2'-deoxynucleotides positioned between wing segments of five 2'-MOE nucleotides.

In additional aspects, the antisense compound comprises the sequence of any one of SEQ ID NOs: 2, 3, or 124-201 targeted to an eRNA that enhances transcription of MMP9.

In certain aspects, the antisense compound is targeted to an eRNA that enhances transcription of CX3CR1, CA12, FOXC1, GREB1, P2RY2, SMAD7, PGR, SIAH2, NRIP1, TFF1, or KCNK5.

In several embodiments, antisense compounds comprise any one of the following pairs of sequences: SEQ ID NOs: 11-12; SEQ ID NOs: 13-14; or SEQ ID NOs: 15-16, or any one of SEQ ID NOs: 60-63 targeted to an eRNA that enhances transcription of TFF1.

In several embodiments, antisense compounds comprise any one of the following pairs of sequences: SEQ ID NOs: 17-18; SEQ ID NOs: 19-20; or SEQ ID NOs: 21-22 targeted to an eRNA that enhances transcription of GREB1.

In several embodiments, antisense compounds comprise any one of the following pairs of sequences: SEQ ID NOs: 23-24 or SEQ ID NOs: 25-26 targeted to an eRNA that enhances transcription of PGR.

In several embodiments, antisense compounds comprise any one of the following pairs of sequences: SEQ ID NOs: 27-28 or SEQ ID NOs: 29-30 targeted to an eRNA that enhances transcription of SIAH2.

In several embodiments, antisense compounds comprise any one of the following pairs of sequences: SEQ ID NOs: 31-32 or SEQ ID NOs: 33-34, or any one of SEQ ID NOs: 68 and 69 targeted to an eRNA that enhances transcription of NRIP1.

In several embodiments, antisense compounds comprise any one of the following pairs of sequences: SEQ ID NOs: 35-36 or SEQ ID NOs: 37-38, or any one of SEQ ID NOs: 66 and 77 targeted to an eRNA that enhances transcription of FOXC1.

In several embodiments, antisense compounds comprise any one of the Mowing pairs of sequences: SEQ ID NOs: 39-40 or SEQ ID NOs: 41-42 targeted to an eRNA that enhances transcription of P2RY2.

In several embodiments, antisense compounds comprise any one of the following pairs of sequences: SEQ NOs: 43-44 or SEQ NOs: 45-46, or any one of SEQ ID NOs: 64 and 65 targeted to an eRNA that enhances transcription of CA12.

In several embodiments, antisense compounds comprise any one of the following pairs of sequences: SEQ ID NOs 47-48, SEQ ID NOs: 49-50, or SEQ ID NOs: 51-52 targeted to an eRNA that enhances transcription of SMAD7.

In several embodiments, antisense compounds comprise any one of the following pairs of sequences: SEQ ID NOs: 53-54, SEQ ID NOs: 55-56, or SEQ ID NOs: 57-5 targeted to an eRNA that enhances transcription of KCNK5.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification at the 2' position of a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanosyl ring other than H or OH. In certain embodiments, 2' substituted nucleosides include nucleosides with bicyclic sugar modifications.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5 position. A 5-methylcytosine is a modified nucleobase.

"About" means within ±7% of a value. For example, if it is stated, "the compounds affected at least about 70% inhibition of eRNA", it is implied that the eRNA levels are inhibited within a range of 63% and 77%.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, F$_{ab}$ region, and F$_c$ region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, snoRNAs, miRNAs, and satellite repeats.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding region or segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar" means a furanose ring modified by the bridging of two non-geminal carbon atoms. A bicyclic sugar is a modified sugar.

"Bicyclic nucleic acid" or "BNA" or "BNA nucleosides" means nucleic acid monomers having a bridge connecting two carbon atoms between the 4' and 2' position of the nucleoside sugar unit, thereby forming a bicyclic sugar. Examples of such bicyclic sugar include, but are not limited to A) α-L-Methyleneoxy (4'-CH$_2$—O-2') LNA, (B) β-D-Methyleneoxy (4'-CH$_2$—O-2') LNA, (C) Ethyleneoxy (4'-(CH$_2$)$_2$—O-2') LNA, (D) Aminooxy (4'-CH$_2$—O—N(R)-2') LNA and (E) Oxyamino (4'-CH$_2$—N(R)—O-2') LNA, as depicted below.

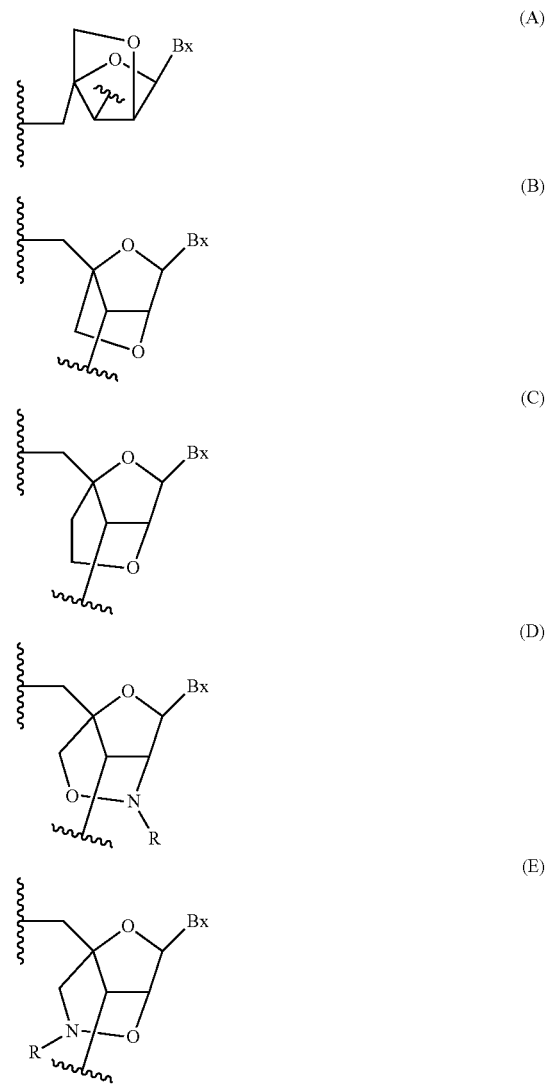

As used herein, LNA compounds include, but are not limited to, compounds having at least one bridge between the 4' and the 2' position of the sugar wherein each of the bridges independently comprises 1 or from 2 to 4 linked groups independently selected from —[C(R$_1$)(R$_2$)]$_n$—, —C(R$_1$)=C(R$_2$)—, —C(R$_1$)=N—, —C(=NR$_1$)—, —C(=O)—, —C(=S)—, —O—, —Si($R_1$)$_2$—, —S(=O)$_x$— and —N($R_1$)—; wherein: x is 0, 1, or 2; n is 1, 2, 3, or 4; each $R_1$ and $R_2$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

Examples of 4'-2' bridging groups encompassed within the definition of LNA include, but are not limited to one of formulae: —[C($R_1$)($R_2$)]$_n$—, —[C($R_1$)($R_2$)]$_n$—O—, —C($R_1R_2$)—N($R_1$)—O— or —C($R_1R_2$)—O—N($R_1$)—. Furthermore, other bridging groups encompassed with the definition of LNA are 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N($R_1$)-2' and 4'-CH$_2$—N($R_1$)—O-2'-bridges, wherein each $R_1$ and $R_2$ is, independently, H, a protecting group or $C_1$-$C_{12}$ alkyl.

Also included within the definition of LNA according to the invention are LNAs in which the 2'-hydroxyl group of the ribosyl sugar ring is connected to the 4' carbon atom of the sugar ring, thereby forming a methyleneoxy (4'-CH$_2$—O-2') bridge to form the bicyclic sugar moiety. The bridge can also be a methylene (—CH$_2$—) group connecting the 2' oxygen atom and the 4' carbon atom, for which the term methyleneoxy (4'-CH$_2$—O-2') LNA is used. Furthermore; in the case of the bicyclic sugar moiety having an ethylene bridging group in this position, the term ethyleneoxy (4'-CH$_2$CH$_2$—O-2') LNA is used. α-L-methyleneoxy (4'-CH$_2$—O-2'), an isomer of methyleneoxy (4'-CH$_2$—O-2') LNA is also encompassed within the definition of LNA, as used herein.

"Cap structure" or "terminal cap moiety" means chemical modifications, which have been incorporated at either terminus of an antisense compound.

"cEt" or "constrained ethyl" means a bicyclic sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Complementarity" means the capacity for pairing between nucleobases of a first nucleic acid and a second nucleic acid.

"Comply" means the adherence with a recommended therapy by an individual.

"Comprise," "comprises" and "comprising" will be understood to imply the inclusion of a stated step or element or group of steps or elements but not the exclusion of any other step or element or group of steps or elements.

"Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Designing" or "Designed to" refer to the process of designing an oligomeric compound that specifically hybridizes with a selected nucleic acid molecule.

"Efficacy" means the ability to produce a desired effect.

"Enhancer" refers to a DNA sequence or region located at some distance away from a gene and capable of stimulating transcription of the gene. In certain embodiments, an enhancer is capable of binding to transcription factors and stimulating promoters "Enhancer RNA (eRNA)" refers to a ribonucleotide transcribed from a genomic enhancer nucleic acid sequence or region or region.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Fully modified motif" refers to an antisense compound comprising a contiguous sequence of nucleosides wherein essentially each nucleoside is a sugar modified nucleoside having uniform modification.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Gap-widened" means an antisense compound having a gap segment of 12 or more contiguous 2'-deoxyribonucleotides positioned between 5' and 3' wing segments having from one to six nucleotides having modified sugar moieties.

"Hybridization" means the annealing of complementary nucleic acid molecules. In certain embodiments, complementary nucleic acid molecules include, but are not limited to, an antisense compound and a nucleic acid target. In certain embodiments, complementary nucleic acid molecules include, but are not limited to, an antisense oligonucleotide and a nucleic acid target.

"Immediately adjacent" means there are no intervening elements between the immediately adjacent elements.

"Individual" means a human or non-human animal selected for treatment or therapy.

"Induce", "inhibit", "potentiate", "elevate", "increase", "decrease" or the like, generally denote quantitative differences between two states.

"Inhibiting the expression or activity" refers to a reduction, blockade of the expression or activity and does not necessarily indicate a total elimination of expression or activity.

"Internucleoside linkage" refers to the chemical bond between nucleosides.

"Lengthened" antisense oligonucleotides are those that have one or more additional nucleosides relative to an antisense oligonucleotide disclosed herein.

"Linked deoxynucleoside" means a nucleic acid base (A, G, C, T, U) substituted by deoxyribose linked by a phosphate ester to form a nucleotide.

"Linked nucleosides" means adjacent nucleosides linked together by an internucleoside linkage.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, or modified nucleobase.

"Modified oligonucleotide" means an oligonucleotide comprising at least one modified internucleoside linkage, a modified sugar, and/or a modified nucleobase.

"Modified sugar" means substitution and/or any change from a natural sugar moiety.

"Monomer" refers to a single unit of an oligomer. Monomers include, but are not limited to, nucleosides and nucleotides, whether naturally occurring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" means a polymer of linked monomeric subunits which is capable of hybridizing to at least a region of a nucleic acid molecule.

"Oligonucleoside" means an oligonucleotide in which the internucleoside linkages do not contain a phosphorus atom.

"Oligonucleotide" means a polymer of linked nucleosides each of which can be modified or unmodified, independent one from another.

"Peptide" means a molecule formed by linking at least two amino acids by amide bonds. Without limitation, as used herein, "peptide" refers to polypeptides and proteins.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound "Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Segments" are defined as smaller or sub-portions of regions within a target nucleic acid.

"Sites," as used herein, are defined as unique nucleobase positions within a target nucleic acid.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments. "Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Target" refers to a protein, the modulation of which is desired.

"Target gene" refers to a gene encoding a target.

"Targeting" means the process of design and selection of an antisense compound that will specifically hybridize to a target nucleic acid and induce a desired effect.

"Target nucleic acid," "target RNA," "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Unmodified" nucleobases mean the purine bases adenine (A) and guanine (G), and the pyrimidine bases thymine (T), cytosine (C) and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Validated target segment" is defined as at least an 8-nucleobase portion (i.e. 8 consecutive nucleobases) of a target region to which an antisense compound is targeted.

"Wing segment" means a plurality of nucleosides modified to impart to an oligonucleotide properties such as enhanced inhibitory activity, increased binding affinity for a target nucleic acid, or resistance to degradation by in vivo nucleases.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound is 10-30 subunits in length. In certain embodiments, an antisense compound is 12 to 30 subunits in length. In certain embodiments, an antisense compound is 12 to 22 subunits in length. In certain embodiments, an antisense compound is 14 to 30 subunits in length. In certain embodiments, an antisense compound is 14 to 20 subunits in length. In certain embodiments, an antisense compound is 15 to 30 subunits in length. In certain embodiments, an antisense compound is 15 to 20 subunits in length. In certain embodiments, an antisense compound is 16 to 30 subunits in length. In certain embodiments, an antisense compound is 16 to 20 subunits in length. In certain embodiments, an antisense compound is 17 to 30 subunits in length. In certain embodiments, an antisense compound is 17 to 20 subunits in length. In certain embodiments, an antisense compound is 18 to 30 subunits in length. In certain embodiments, an antisense compound is 18 to 21 subunits in length. In certain embodiments, an antisense compound is 18 to 20 subunits in length. In certain embodiments, an antisense compound is 20 to 30 subunits in length. In other words, such antisense compounds are from 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, an antisense compound is 14 subunits in length. In certain embodiments, an antisense compound is 16 subunits in length. In certain embodiments, an antisense compound is 17 subunits in length. In certain embodiments, an antisense compound is 18 subunits in length. In certain embodiments, an antisense compound is 20 subunits in length. In other embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleotides.

In certain embodiments antisense oligonucleotides may be shortened or truncated. For example, a single subunit may be deleted from the 5' end (5' truncation), or alternatively from the 3' end (3' truncation). A shortened or truncated antisense compound targeted to an eRNA nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al. (*J. Natl. Cancer Inst.* 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (*Nuc. Acid. Res.* 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Certain Antisense Compound Motifs and Mechanisms

In certain embodiments, antisense compounds have chemically modified subunits arranged in patterns, or motifs, to confer to the antisense compounds properties such as enhanced inhibitory activity, increased binding affinity for a target nucleic acid, or resistance to degradation by in vivo nucleases. Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may confer another desired property e.g., serve as a substrate for the cellular endonuclease RNase H, which cleaves the RNA strand of an RNA:DNA duplex.

Antisense activity may result from any mechanism involving the hybridization of the antisense compound (e.g., oligonucleotide) with a target nucleic acid, wherein the hybridization ultimately results in a biological effect. In certain embodiments, the amount and/or activity of the target nucleic acid is modulated. In certain embodiments, the amount and/or activity of the target nucleic acid is reduced. In certain embodiments, hybridization of the antisense compound to the target nucleic acid ultimately results in target nucleic acid degradation. In certain embodiments, hybridization of the antisense compound to the target nucleic acid does not result in target nucleic acid degradation. In certain such embodiments, the presence of the antisense compound hybridized with the target nucleic acid (occupancy) results in a modulation of antisense activity. In certain embodiments, antisense compounds having a particular chemical motif or pattern of chemical modifications are particularly suited to exploit one or more mechanisms. In certain embodiments, antisense compounds function through more than one mechanism and/or through mechanisms that have not been elucidated. Accordingly, the antisense compounds described herein are not limited by particular mechanism.

Antisense mechanisms include, without limitation, RNase H mediated antisense; RNAi mechanisms, which utilize the RISC pathway and include, without limitation, siRNA, ssRNA and microRNA mechanisms; and occupancy based mechanisms. Certain antisense compounds may act through more than one such mechanism and/or through additional mechanisms.

RNase H-Mediated Antisense

In certain embodiments, antisense activity results at least in part from degradation of target RNA by RNase H. RNase H is a cellular endonuclease that cleaves the RNA strand of an RNA:DNA duplex. It is known in the art that single-stranded antisense compounds which are "DNA-like" elicit RNase H activity in mammalian cells. Accordingly, antisense compounds comprising at least a portion of DNA or DNA-like nucleosides may activate RNase H, resulting in cleavage of the target nucleic acid. In certain embodiments, antisense compounds that utilize RNase H comprise one or more modified nucleosides. In certain embodiments, such antisense compounds comprise at least one block of 1-8 modified nucleosides. In certain such embodiments, the modified nucleosides do not support RNase H activity. In certain embodiments, such antisense compounds are gapmers, as described herein. In certain such embodiments, the gap of the gapmer comprises DNA nucleosides. In certain such embodiments, the gap of the gapmer comprises DNA-like nucleosides. In certain such embodiments, the gap of the gapmer comprises DNA nucleosides and DNA-like nucleosides.

Certain antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—CH$_3$, among others), and bicyclic sugar modified nucleosides (such bicyclic sugar modified nucleosides may include those having a constrained ethyl). In certain embodiments, nucleosides in the wings may include several modified sugar moieties, including, for example 2'-MOE and bicyclic sugar moieties such as constrained ethyl or LNA. In certain embodiments, wings may include several modified and unmodified sugar moieties. In certain embodiments, wings may include various combinations of 2'-MOE nucleosides, bicyclic sugar moieties such as constrained ethyl nucleosides or LNA nucleosides, and 2'-deoxynucleosides.

Each distinct region may comprise uniform sugar moieties, variant, or alternating sugar moieties. The wing-gap-wing motif is frequently described as "X—Y—Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides."Y" may comprise 2'-deoxynucleosides. As used herein, a gapmer described as "X—Y—Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different.

In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, gapmers provided herein include, for example, 11-mers having a motif of 1-9-1.

In certain embodiments, gapmers provided herein include, for example, 12-mers having a motif of 1-9-2, 2-9-1, or 1-10-1.

In certain embodiments, gapmers provided herein include, for example, 13-mers having a motif of 1-9-3, 2-9-2, 3-9-1, 1-10-2, or 2-10-1.

In certain embodiments, gapmers provided herein include, for example, 14-mers having a motif of 1-9-4, 2-9-3, 3-9-2, 4-9-1, 1-10-3, 2-10-2, or 3-10-1.

In certain embodiments, gapmers provided herein include, for example, 15-mers having a motif of 1-9-5, 2-9-4, 3-9-3, 4-9-2, 5-9-1, 1-10-4, 2-10-3, 3-10-2, or 4-10-1.

In certain embodiments, gapmers provided herein include, for example, 16-mers having a motif of 4-8-4, 2-9-5, 3-9-4, 4-9-3, 5-9-2, 1-10-5, 2-10-4, 3-10-3, 4-10-2, 3-8-5, or 5-10-1.

In certain embodiments, gapmers provided herein include, for example, 17-mers having a motif of 3-9-5, 3-10-4, 4-9-4, 5-9-3, 2-10-5, 3-10-4, 4-10-3, 5-10-2, 2-9-6, 5-8-4, 5-7-5, 6-7-4, or 6-9-2.

In certain embodiments, gapmers provided herein include, for example, 18-mers having a motif of 4-9-5, 5-9-4, 3-10-5, 4-10-4, or 5-10-3.

In certain embodiments, gapmers provided herein include, for example, 19-mers having a motif of 5-9-5, 4-10-5, or 5-10-4.

In certain embodiments, gapmers provided herein include, for example, 20-mers having a motif of 5-10-5, 2-10-8, 8-10-2, 3-10-7, 7-10-3, 4-10-6, or 6-10-4.

In certain embodiments, the antisense compound has a "wingmer" motif, having a wing-gap or gap-wing configuration, i.e. an X—Y or Y—Z configuration as described above for the gapmer configuration. Thus, wingmer configurations provided herein include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, the antisense compound targeted to an eRNA nucleic acid has a 2-10-2 gapmer motif.

In certain embodiments, the antisense compound targeted to an eRNA nucleic acid has a 3-10-3 gapmer motif.

In certain embodiments, the antisense compound targeted to an eRNA nucleic acid has a 4-10-4 gapmer motif.

In certain embodiments, the antisense compound targeted to an eRNA nucleic acid has a 5-10-5 gapmer motif.

In certain embodiments, the antisense compound targeted to an eRNA nucleic acid has a 3-10-4 gapmer motif.

In certain embodiments, the antisense compound targeted to an eRNA nucleic acid has a 2-10-4 gapmer motif.

In certain embodiments, the antisense compound targeted to an eRNA nucleic acid has a 2-10-8 gapmer motif.

In certain embodiments, the antisense compound targeted to an eRNA nucleic acid has a 8-10-2 gapmer motif.

In certain embodiments, the antisense compound targeted to an eRNA nucleic acid has a 3-10-7 gapmer motif.

In certain embodiments, the antisense compound targeted to an eRNA nucleic acid has a 7-10-3 gapmer motif.

In certain embodiments, the antisense compound targeted to an eRNA nucleic acid has a 4-10-6 gapmer motif.

In certain embodiments, the antisense compound targeted to an eRNA nucleic acid has a 6-10-4 gapmer motif.

In certain embodiments, the antisense compound targeted to an eRNA nucleic acid has a 2-9-6 gapmer motif.

In certain embodiments, the antisense compound targeted to an eRNA nucleic acid has a 6-9-2 gapmer motif.

In certain embodiments, the antisense compound targeted to an eRNA nucleic acid has a 4-9-4 gapmer motif.

In certain embodiments, the antisense compound targeted to an eRNA nucleic acid has a 5-9-3 gapmer motif.

In certain embodiments, the antisense compound targeted to an eRNA nucleic acid has a 3-9-5 gapmer motif.

In certain embodiments, the antisense compound targeted to an eRNA nucleic acid has a 5-9-2 gapmer motif.

In certain embodiments, the antisense compound targeted to an eRNA nucleic acid has a 2-9-5 gapmer motif.

In certain embodiments, the antisense compound targeted to an eRNA nucleic acid has a 4-9-3 gapmer motif.

In certain embodiments, the antisense compound targeted to an eRNA nucleic acid has a 3-9-4 gapmer motif.

In certain embodiments, the antisense compound targeted to an eRNA nucleic acid has a gap-widened motif.

In certain embodiments, the antisense compound targeted to an eRNA nucleic acid has a gapmer motif in which the gap consists of 6, 7, 8, 9, 10, 11, 12, 13, 14, 15, or 16 linked nucleosides.

In certain embodiments, the antisense compounds targeted to an eRNA nucleic acid has any of the following sugar motifs:

k-d(10)-k
e-d(10)-k
k-d(10)-e
k-k-d(10)-k-k
k-k-d(10)-e-e
e-e-d(10)-k-k
k-k-k-d(10)-k-k-k
e-e-e-d(10)-k-k-k
k-k-k-d(10)-e-e-e
k-k-k-d(10)-k-k-k
e-k-k-d(10)-k-k-e
e-e-k-d(10)-k-k-e
e-d-k-d(10)-k-k-e
e-k-k-d(10)-k-e-k-e
k-d(10)-k-e-k-e-e
e-e-k-d(10)-k-e-k-e
e-d-d-k-d(9)-k-k-e
e-e-e-e-d(9)-k-k-e
e-e-e-e-e-d(10)-e-e-e-e-e
k-d-k-d-k-d(9)-e-e
e-e-k-k-d(9)-e-k-e-e
k-d-k-d-k-d(10)-e-e-e-e-e
k-e-k-d(10)-k-e-k
e-e-e-k-k-d(8)-e-e-e-e
e-e-e-k-k-d(7)-k-k-e-e-e
e-e-e-k-d(9)-k-e-e-e
e-e-e-k-k-d(7)-k-k-e-e-e
e-e-e-e-k-k-d(7)-e-e-e-e
e-k-e-k-d(9)-e-e-e-e
e-k-e-k-d-k-d(7)-e-e-e-e
e-e-e-k-k-d(7)-k-k-e-e-e
k-d-k-d-k-d(8)-e-e-e-e-e wherein, k is a constrained ethyl nucleoside, e is a 2'-MOE substituted nucleoside, and d is a 2'-deoxynucleoside.

In certain embodiments, the antisense oligonucleotide has a sugar motif described by Formula A as follows: $(J)_m\text{-}(B)_n\text{-}(J)_p\text{-}(B)_r\text{-}(A)_t\text{-}(D)_g\text{-}(A)_v\text{-}(B)_w\text{-}(J)_x\text{-}(B)_y\text{-}(J)_z$ wherein:
each A is independently a 2'-substituted nucleoside;
each B is independently a bicyclic nucleoside;

each J is independently either a 2'-substituted nucleoside or a 2'-deoxynucleoside;

each D is a 2'-deoxynucleoside;

m is 0-4; n is 0-2; p is 0-2; r is 0-2; t is 0-2; v is 0-2; w is 0-4; x is 0-2; y is 0-2; z is 0-4; g is 6-14; provided that:
at least one of m, n, and r is other than 0;
at least one of w and y is other than 0;
the sum of m, n, p, r, and t is from 2 to 5; and
the sum of v, w, x, y, and z is from 2 to 5.

RNAi Compounds

In certain embodiments, antisense compounds are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). In certain embodiments, antisense compounds comprise modifications that make them particularly suited for such mechanisms.

i. ssRNA Compounds

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO/2011/139702.

In certain embodiments, the 5'-nucleoside of an ssRNA compound has Formula IIc:

wherein:

$T_1$ is an optionally protected phosphorus moiety;

$T_2$ is an internucleoside linking group linking the compound of Formula IIc to the oligomeric compound;

A has one of the formulas:

$Q_1$ and $Q_2$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;

$Q_3$ is O, S, $N(R_5)$ or $C(R_6)(R_7)$;

each $R_3$, $R_4$, $R_5$, $R_6$ and $R_7$ is, independently, H, $C_1$-$C_6$ alkyl, substituted $C_1$-$C_6$ alkyl or $C_1$-$C_6$ alkoxy;

$M_3$ is O, S, $NR_{14}$, $C(R_{15})(R_{16})$, $C(R_{15})(R_{16})C(R_{17})(R_{18})$, $C(R_{15})=C(R_{17})$, $OC(R_{15})(R_{16})$ or $OC(R_{15})(Bx_2)$;

$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$Bx_1$ is a heterocyclic base moiety;

or if $Bx_2$ is present then $Bx_2$ is a heterocyclic base moiety and $Bx_1$ is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

or $J_4$ forms a bridge with one of $J_5$ or $J_7$ wherein said bridge comprises from 1 to 3 linked biradical groups selected from O, S, $NR_{19}$, $C(R_{20})(R_{21})$, $C(R_{20})=C(R_{21})$, $C[=C(R_{20})(R_{21})]$ and $C(=O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or O—$[C(R_8)(R_9)]_n$—$[(C=O)_m$—$X_1]_j$—Z;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=X_2)N(J_1)(J_2)$;

$X_2$ is O, S or $NJ_3$;

each $J_1$, $J_2$ and $J_3$ is, independently, H or $C_1$-$C_6$ alkyl;

when j is 1 then Z is other than halogen or $N(E_2)(E_3)$; and wherein said oligomeric compound comprises from 8 to 40 monomeric subunits and is hybridizable to at least a portion of a target nucleic acid.

In certain embodiments, $M_3$ is O, CH=CH, $OCH_2$ or $OC(H)(Bx_2)$. In certain embodiments, $M_3$ is O.

In certain embodiments, $J_4$, $J_5$, $J_6$ and $J_7$ are each H. In certain embodiments, $J_4$ forms a bridge with one of $J_5$ or $J_7$.

In certain embodiments, A has one of the formulas:

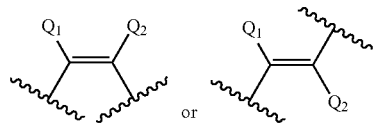

wherein:

$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each H. In certain embodiments, $Q_1$ and $Q_2$ are each, independently, H or halogen. In certain embodiments, $Q_1$ and $Q_2$ is H and the other of $Q_1$ and $Q_2$ is F, $CH_3$ or $OCH_3$.

In certain embodiments, $T_1$ has the formula:

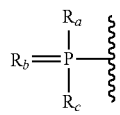

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S. In certain embodiments, $R_b$ is O and $R_a$ and $R_c$ are each, independently, $OCH_3$, $OCH_2CH_3$ or $CH(CH_3)_2$.

In certain embodiments, G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_{10})(R_{11})$, $O(CH_2)_2$—$ON(R_{10})(R_{11})$, $O(CH_2)_2$—$O(CH_2)_2$—$N(R_{10})(R_{11})$, $OCH_2C(=O)$—$N(R_{10})(R_{11})$, $OCH_2C(=O)$—N$(R_{12})$—$(CH_2)_2$—$N(R_{10})(R_{11})$ or $O(CH_2)_2$—$N(R_{12})$—C$(=NR_{13})[N(R_{10})(R_{11})]$ wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—N(H)—$(CH_2)_2$—$N(CH_3)_2$ or $OCH_2$—N(H)—C$(=NH)NH_2$.
In certain embodiments, G is F, $OCH_3$ or $O(CH_2)_2$—$OCH_3$.
In certain embodiments, G is $O(CH_2)_2$—$OCH_3$.

In certain embodiments, the 5'-terminal nucleoside has Formula IIe:

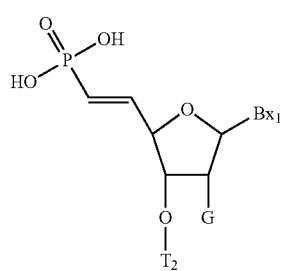

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modifications are 2'-F and 2'-OMe. Such regions may be contiguous or may be interrupted by differently modified nucleosides or conjugated nucleosides.

In certain embodiments, the alternating region of alternating modifications each consist of a single nucleoside (i.e., the pattern is $(AB)_xA_y$ wheren A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides may include one or more regions of any of the following nucleoside motifs:

AABBAA;

ABBABB;

AABAAB;

ABBABAABB;

ABABAA;

AABABAB;

ABABAA;

ABBAABBABABAA;

BABBAABBABABAA;
    or

ABABBAABBABABAA;

wherein A is a nucleoside of a first type and B is a nucleoside of a second type. In certain embodiments, A and B are each selected from 2'-F, 2'-OMe, BNA, and MOE.

In certain embodiments, oligonucleotides having such an alternating motif also comprise a modified 5' terminal nucleoside, such as those of formula IIc or IIe.

In certain embodiments, oligonucleotides comprise a region having a 2-2-3 motif. Such regions comprises the following motif:

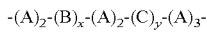

wherein: A is a first type of modified nucleoside;

B and C, are nucleosides that are differently modified than A, however, B and C may have the same or different modifications as one another;

x and y are from 1 to 15.

In certain embodiments, A is a 2'-OMe modified nucleoside. In certain embodiments, B and C are both 2'-F modified nucleosides. In certain embodiments, A is a 2'-OMe modified nucleoside and B and C are both 2'-F modified nucleosides.

In certain embodiments, oligonucleosides have the following sugar motif:

wherein:

Q is a nucleoside comprising a stabilized phosphate moiety. In certain embodiments, Q is a nucleoside having Formula IIc or IIe;

A is a first type of modified nucleoside;

B is a second type of modified nucleoside;

D is a modified nucleoside comprising a modification different from the nucleoside adjacent to it. Thus, if y is 0, then D must be differently modified than B and if y is 1, then D must be differently modified than A. In certain embodiments, D differs from both A and B.

X is 5-15;

Y is 0 or 1;

Z is 0-4.

In certain embodiments, oligonucleosides have the following sugar motif:

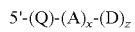

wherein:

Q is a nucleoside comprising a stabilized phosphate moiety. In certain embodiments, Q is a nucleoside having Formula IIc or IIe;

A is a first type of modified nucleoside;

D is a modified nucleoside comprising a modification different from A.

X is 11-30;

Z is 0-4.

In certain embodiments A, B, C, and D in the above motifs are selected from: 2'-OMe, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
|---|---|---|
| PS | Alternating PO/PS | 6 PS |
| PS | Alternating PO/PS | 7 PS |
| PS | Alternating PO/PS | 8 PS | ii. siRNA Compounds

In certain embodiments, antisense compounds are double-stranded RNAi compounds (siRNA). In such embodiments, one or both strands may comprise any modification motif described above for ssRNA. In certain embodiments, ssRNA compounds may be unmodified RNA. In certain embodiments, siRNA compounds may comprise unmodified RNA nucleosides, but modified internucleoside linkages.

Several embodiments relate to double-stranded compositions wherein each strand comprises a motif defined by the location of one or more modified or unmodified nucleosides. In certain embodiments, compositions are provided comprising a first and a second oligomeric compound that are fully or at least partially hybridized to form a duplex region and further comprising a region that is complementary to and hybridizes to a nucleic acid target. It is suitable that such a composition comprise a first oligomeric compound that is an antisense strand having full or partial complementarity to a nucleic acid target and a second oligomeric compound that is a sense strand having one or more regions of complementarity to and forming at least one duplex region with the first oligomeric compound.

The compositions of several embodiments modulate gene expression by hybridizing to a nucleic acid target resulting in loss of its normal function. In some embodiments, the target nucleic acid is an eRNA. In certain embodiment, the degradation of the targeted eRNA is facilitated by an activated RISC complex that is formed with compositions of the invention.

Several embodiments are directed to double-stranded compositions wherein one of the strands is useful in, for example, influencing the preferential loading of the opposite strand into the RISC (or cleavage) complex. The compositions are useful for targeting selected nucleic acid molecules and modulating the expression of one or more genes. In some embodiments, the compositions of the present invention hybridize to a portion of a target RNA resulting in loss of normal function of the target RNA.

Certain embodiments are drawn to double-stranded compositions wherein both the strands comprises a hemimer motif, a fully modified motif, a positionally modified motif or an alternating motif. Each strand of the compositions of the present invention can be modified to fulfil a particular role in for example the siRNA pathway. Using a different motif in each strand or the same motif with different chemical modifications in each strand permits targeting the antisense strand for the RISC complex while inhibiting the incorporation of the sense strand. Within this model, each strand can be independently modified such that it is enhanced for its particular role. The antisense strand can be modified at the 5'-end to enhance its role in one region of the RISC while the 3'-end can be modified differentially to enhance its role in a different region of the RISC.

The double-stranded oligonucleotide molecules can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The double-stranded oligonucleotide molecules can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the double-stranded oligonucleotide molecule are complementary to the target nucleic acid or a portion thereof). Alternatively, the double-stranded oligonucleotide is assembled from a single oligonucleotide, where the self-complementary sense and antisense regions of the siRNA are linked by means of a nucleic acid based or non-nucleic acid-based linker(s).

The double-stranded oligonucleotide can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The double-stranded oligonucleotide can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNAi.

In certain embodiments, the double-stranded oligonucleotide comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the double-stranded oligonucleotide comprises nucleotide sequence that is complementary to nucleotide sequence of a target gene. In another embodiment, the double-stranded oligonucleotide interacts with nucleotide sequence of a target gene in a manner that causes inhibition of expression of the target gene.

As used herein, double-stranded oligonucleotides need not be limited to those molecules containing only RNA, but further encompasses chemically modified nucleotides and non-nucleotides. In certain embodiments, the short interfering nucleic acid molecules lack 2'-hydroxy (2'-OH) containing nucleotides. In certain embodiments short interfering nucleic acids optionally do not include any ribonucleotides (e.g., nucleotides having a 2'-OH group). Such double-stranded oligonucleotides that do not require the presence of ribonucleotides within the molecule to support RNAi can however have an attached linker or linkers or other attached or associated groups, moieties, or chains containing one or more nucleotides with 2'-OH groups. Optionally, double-stranded oligonucleotides can comprise ribonucleotides at about 5, 10, 20, 30, 40, or 50% of the nucleotide positions. As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, double-stranded oligonucleotides can be used to epigenetically silence genes at both the post-transcriptional level and the pre-transcriptional level. In a non-limiting example, epigenetic regulation of gene expression by siRNA molecules of the invention can result from siRNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

It is contemplated that compounds and compositions of several embodiments provided herein can target eRNAs by a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other.

In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. In certain embodiments, the regions of complementarity are at least 70, 80, 90, 95, 98, or 100% complementary to each other and to a target nucleic acid sequence. In certain embodiments, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. In certain embodiments, RNA/DNA hybrids include a DNA strand or region that is an antisense strand or region (e.g, has at least 70, 80, 90, 95, 98, or 100% complementarity to a target nucleic acid) and an RNA strand or region that is a sense strand or region (e.g, has at least 70, 80, 90, 95, 98, or 100% identity to a target nucleic acid), and vice versa.

In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999.

In other embodiments, the dsRNA can be any of the at least partially dsRNA molecules disclosed in WO 00/63364, as well as any of the dsRNA molecules described in U.S. Provisional Application 60/399,998; and U.S. Provisional Application 60/419,532, and PCT/US2003/033466, the teaching of which is hereby incorporated by reference. Any of the dsRNAs may be expressed in vitro or in vivo using the methods described herein or standard methods, such as those described in WO 00/63364.

Occupancy

In certain embodiments, antisense compounds are not expected to result in cleavage or the target nucleic acid via RNase H or to result in cleavage or sequestration through the RISC pathway. In certain such embodiments, antisense activity may result from occupancy, wherein the presence of the hybridized antisense compound disrupts the activity of the target nucleic acid. In certain such embodiments, the antisense compound may be uniformly modified or may comprise a mix of modifications and/or modified and unmodified nucleosides.

Target eRNAs and Associated Gene Expression

Several embodiments are directed to methods of modulating gene expression by inhibiting eRNAs. In certain embodiments, transcriptional start site of such a gene is located on a chromosome at least about 1 kilobase (kb) from the genomic enhancer nucleic acid sequence. In certain embodiments, eRNAs suitable for inhibition include RNA transcripts characterized by any one or more of the following: (1) transcribed from genomic regions characterized by high levels of monomethylation on lysine 4 of histone 3 (H3K4me1) and low levels of trimethylation on lysine 4 of histone 3 (H3K4me3)(2) transcribed from genomic regions that are enriched for RNA polymerase II (PolII); (3) transcribed from genomic regions that are enriched for transcriptional co-regulators, such as the p300 co-activator; (4) their transcription is initiated from PolII-binding sites and elongated bidirectionally; (5) evolutionarily conserved DNA sequences encoding eRNAs; (6) short half-life; (7) dynamically regulated upon signaling, and/or (7) positively correlated to levels of nearby mRNA expression. In certain aspects, the half-life of the eRNA is less than about 10-30 minutes.

In certain embodiments, eRNAs suitable for inhibition with compounds described herein include eRNAs from hematopoietic cells, such as monocytes or macrophages. Examples of such eRNAs include, but are not limited to, those transcribed from enhancers identified by genomic coordinates in Mega-Tables 1 and 2 filed in U.S. Provisional Application No. 61/650,426 in electronic format on May 22, 2012. Additional information on the eRNAs transcribed from enhancers listed in Mega-Table 2 is reported in De Santa F, et al., "A large fraction of extragenic RNA pol II transcription sites overlap enhancers." *PLoS Biol* 2010; 8:e1000384, which is herein incorporated by reference in its entirety.

In certain embodiments, eRNAs suitable for inhibition with compounds described herein include eRNAs from neurons. Examples of such eRNAs include, but are not limited to, those transcribed from enhancers identified by genomic coordinates in Mega-Table 3 filed in U.S. Provisional Application No. 61/650,426 in electronic format on May 22, 2012. Additional information on the eRNAs transcribed from enhancers listed in Mega-Table 3 is reported in Kim T K, et al., "Widespread transcription at neuronal activity-regulated enhancers." Nature 2010; 465:182-187, which is herein incorporated by reference in its entirety.

In certain embodiments, eRNAs suitable for inhibition with compounds described herein include eRNAs transcribed from enhancers identified as highly conserved among human, mouse, and rat species. Examples of such eRNAs include, but are not limited to, those transcribed from enhancers identified by genomic coordinates in Mega-Table 4 and Mega-Table 5 filed in U.S. Provisional Application No. 61/650,426 in electronic format on May 22, 2012. Mega-Tables 4 and 5 are in 4-column format: chr start end log 10(1/pvalue).

Additional information on the enhancers listed in Mega-Table 4 is reported in Pennacchio et al, Nature 2006; 444:499-502, Prabhakar S, et al. Genome Res. 2006; 16:855-863, and (pga.jgi-psf.org/gumby/), each of which is incorporated herein by reference in its entirety. Chromosome coordinates provided in Mega-Table 4 correspond to the hg17 human genome assembly. Additional information on the enhancers listed in Mega-Table 5 is reported in Visel et al., "VISTA Enhancer Browser—a database of tissue-specific human enhancers," Nucleic Acids Research 2007 (35): D88-92 and (pga.jgi-psf.org/gumby/), each of which is incorporated herein by reference in its entirety. Chromosome coordinates provided in Mega-Table 5 correspond to the hg18 human genome assembly.

In certain embodiments, eRNAs suitable for inhibition with compounds described herein include eRNAs transcribed from human enhancers identified by genomic coordinates in Mega-Table 6 filed in U.S. Provisional Application No. 61/650,426 in electronic format on May 22, 2012. Chromosome coordinates provided in Mega-Table 6 correspond to the hg19 human genome assembly. Additional information on the enhancers listed in Mega-Table 6 is reported in Visel et al., "VISTA Enhancer Browser—a database of tissue-specific human enhancers," Nucleic Acids Research 2007 (35):D88-92 and the VISTA database website (enhancer.lbl.gov/), each of which is incorporated herein by reference in its entirety.

In certain embodiments, eRNAs suitable for inhibition with compounds described herein include eRNAs transcribed from mouse enhancers identified by genomic coordinates in Mega-Table 7 filed in U.S. Provisional Application No. 61/650,426 in electronic format on May 22, 2012. Chromosome coordinates provided in Mega Table7 correspond to the mouse mm9 genome assembly. Additional information on the enhancers listed in Mega-Table 7 is reported in Visel et al., "VISTA Enhancer Browser—a database of tissue-specific human enhancers," Nucleic Acids Research 2007 (35):D88-92 and the VISTA database website (enhancer.lbl.gov/), each of which is incorporated herein by reference in its entirety.

In certain embodiments, eRNAs suitable for inhibition with compounds described herein include eRNAs transcribed from enhancers in human prostate cells. Examples of such eRNAs include, but are not limited to, those identified in LNCaP cells as reported in Wang D et al., "Reprogramming transcription by distinct classes of enhancers functionally defined by eRNA," Nature. 2011 474(7351):390-4 and further described at www.nature.com/nature/journal/v474/n7351/full/nature10006.html, each of which is incorporated herein by reference in its entirety. Further description of the eRNAs identified in Wang et al. are available as high-throughput data deposited at Gene Expression Omnibus (www.ncbi.nlm.nih.gov/geo/) under accession number GSE27823, which is incorporated herein by reference in its entirety.

In certain embodiments, eRNAs suitable for inhibition with compounds described herein include eRNAs transcribed from enhancers in human breast cells, such as breast cancer cells. Examples of such eRNAs include, but are not limited to, those transcribed from enhancers identified in MCF-7 human breast cancer cells and listed in Mega-Table 8 and Mega-Table 9 filed in U.S. Provisional Application No. 61/650,426 in electronic format on May 22, 2012. Chromosome coordinates provided in Mega-Table 8 and Mega-Table 9 correspond to the hg18 human genome assembly. Additional examples of such eRNAs include, but are not limited to, those transcribed from enhancers identified in MCF-7 human breast cancer cells as reported in the UCSC Genome Browser located at (genome.ucsc.edu/cgi-bin/hgTracks?hgS_doOtherUser=submit&hgS_otherUserName=Bogdantanasa&hgS_otherUserSessionName=EReRNAs), which is incorporated herein by reference in its entirety.

In certain embodiments, eRNAs suitable for inhibition with compounds described herein exclude ncRNA-activators (ncRNA-a), such as those described in Orom U A et al., "Long noncoding RNAs with enhancer-like function in human cells." Cell 2010; 1.43:46-58. In certain embodiments, eRNAs suitable for inhibition with compounds described herein exclude transcripts that are characterized by one or more of the following features: (1) produced via unidirectional transcription; (2) polyadenylated; and/or (3), transcribed from a genomic sequence or region having a H3K4 trimethylation chromatin signature.

In certain embodiments, a method of inhibiting gene expression in a macrophage cell comprises administering to the macrophage cell an antisense compound targeted to an eRNA transcribed from a genomic enhancer nucleic acid sequence or region that is enriched for binding to Rev-Erbα or Rev-Erbβ.

In certain embodiments, a method of inhibiting MMP9 gene expression in a cell comprises administering to the cell an antisense compound targeted to an eRNA transcript of a MMP9 enhancer. In several embodiments, the MMP9 eRNA sequence is the product of transcription of SEQ ID NO: 1 (GENBANK Accession No. NT_039207.7 truncated from 105809972 to 105810309).

In certain aspects, the antisense compound is an antisense oligonucleotide that targets the MMP9 eRNA at nucleotides 247 to 262 of the transcribed product of SEQ ID NO:1 In certain aspects, the antisense compound is an antisense oligonucleotide having the nucleic acid sequence of SEQ ID NO:2 in some aspects, the antisense compound is ISIS 566237.

In certain aspects, the antisense compound is an antisense oligonucleotide that targets the MMP9 eRNA at nucleotides 260 to 275 of the transcribed product of SEQ ID NO:1 In certain aspects, the antisense compound is an antisense oligonucleotide having the nucleic acid sequence of SEQ ID NO:3. In some aspects, the antisense compound is ISIS 566241.

In certain aspects, the antisense compound is an antisense oligonucleotide that targets the MMP9 eRNA transcribed from SEQ ID NO: 202 (GENBANK Accession number NT_039207.7 truncated from 105809967 to 105810417). In certain aspects, the antisense compound is an antisense oligonucleotide having the nucleic acid sequence of any one of SEQ ID NOs: 2, 3, or 124-201. MMP9 is known to be associated with atherosclerosis, inflammation, apoptosis, and cancer metastasis; methods and compounds provided herein are useful for inhibiting MMP9 gene expression.

In certain embodiments, a method of inhibiting CX3CR1 gene expression in a cell comprises administering to the cell an antisense compound targeted to an eRNA transcript of a CX3CR1 enhancer. In several embodiments, the CX3CR1 eRNA sequence is the product of transcription of nucleotides 11132282 to 11132781 of SEQ ID NO: 4 (Genbank Accession No. NT_039482.7), which is incorporated herein by reference. In several embodiments, the CX3CR1 eRNA sequence is the product of transcription of nucleotides 11132134 to 11131599 of SEQ ID NO: 4 (Genbank Accession No. NT_039482.7), which is incorporated herein by reference. CX3CR1 is known to be associated with atherosclerosis; methods and compounds provided herein are useful for inhibiting CX3CR1 gene expression.

In certain embodiments, a method of inhibiting TFF1 gene expression in a cell comprises administering to the cell an antisense compound targeted to an eRNA transcript of a TFF1 enhancer, In several embodiments, the antisense compound is a double-stranded siRNA having any one of the following pairs of sequences: SEQ NOs: 11-12; SEQ ID NOs: 13-14; or SEQ ID NOs: 15-16. In several embodiments, the antisense compound is a single-stranded oligonucleotide having a nucleotide sequence of any one of SEQ NOs: 60-63.

In certain embodiments, a method of inhibiting GREB1 gene expression in a cell comprises administering to the cell an antisense compound targeted to an eRNA transcript of a GREB1 enhancer. In several embodiments, the antisense compound is a double-stranded siRNA having any one of the following pairs of sequences: SEQ ID NOs: 17-18; SEQ ID NOs: 19-20; or SEQ NOs: 21-22.

In certain embodiments, a method of inhibiting PGR gene expression in a cell comprises administering to the cell an antisense compound targeted to an eRNA transcript of a PGR enhancer. In several embodiments, the antisense compound is a double-stranded siRNA having any one of the following pairs of sequences: SEQ ID NOs: 23-24 or SEQ ID NOs: 25-26.

In certain embodiments, a method of inhibiting SIAH2 gene expression in a cell comprises administering to the cell an antisense compound targeted to an eRNA transcript of a SIAH2 enhancer. In several embodiments, the antisense compound is a double-stranded siRNA having any one of the following pairs of sequences: SEQ ID NOs: 27-28 or SEQ ID NOs: 29-30.

In certain embodiments, a method of inhibiting NRP1 gene expression in a cell comprises administering to the cell an antisense compound targeted to an eRNA transcript of a NRIP1 enhancer. In several embodiments, the antisense compound is a double-stranded siRNA having any one of the following pairs of sequences: SEQ NOs: 31-32 or SEQ ID NOs: 33-34. In several embodiments, the antisense compound is a single-stranded oligonucleotide having a nucleotide sequence of any one of SEQ ID NOs: 68 or 69.

In certain embodiments, a method of inhibiting FOXC1 gene expression in a cell comprises administering to the cell an antisense compound targeted to an eRNA transcript of a FOXC1 enhancer. In several embodiments, the antisense compound is a double-stranded siRNA having any one of the following pairs of sequences: SEQ NOs: 35-36 or SEQ NOs: 37-38. In several embodiments, the antisense compound is a single-stranded oligonucleotide having a nucleotide sequence of any one of SEQ ID NOs: 66 or 67.

In certain embodiments, a method of inhibiting P2RY2 gene expression in a cell comprises administering to the cell an antisense compound targeted to an eRNA transcript of a P2RY2 enhancer. In several embodiments, the antisense compound is a double-stranded siRNA having any one of the following pairs of sequences: SEQ ID NOs: 39-40 or SEQ ID NOs: 41-42.

In certain embodiments, a method of inhibiting CA12 gene expression in a cell comprises administering to the cell an antisense compound targeted to an eRNA transcript of a CA12 enhancer, in several embodiments, the antisense compound is a double-stranded siRNA having any one of the following pairs of sequences: SEQ NOs: 43-44 or SEQ ID NOs: 45-46. In several embodiments, the antisense compound is a single-stranded oligonucleotide having a nucleotide sequence of any one of SEQ NOs: 64 or 65.

In certain embodiments, a method of inhibiting SMAD7 gene expression in a cell comprises administering to the cell an antisense compound targeted to an eRNA transcript of a SMAD7 enhancer. In several embodiments, the antisense compound is a double-stranded siRNA having any one of the following pairs of sequences: SEQ ID NOs: 47-48, SEQ NOs: 49-50, or SEQ ID NOs: 51-52.

In certain embodiments, a method of inhibiting KCNK5 gene expression in a cell comprises administering to the cell an antisense compound targeted to an eRNA transcript of a KCNK5 enhancer. In several embodiments, the antisense compound is a double-stranded siRNA having any one of the following pairs of sequences: SEQ ID NOs: 53-54, SEQ NOs: 55-56, or SEQ ID NOs: 57-58.

Hybridization

In some embodiments, hybridization occurs between an antisense compound disclosed herein and an eRNA. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with an eRNA.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an eRNA nucleic acid).

Non-complementary nucleobases between an antisense compound and an eRNA nucleic acid may be tolerated provided that the antisense compound remains able to specifically hybridize to a target nucleic acid. Moreover, an antisense compound may hybridize over one or more segments of an eRNA nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to an eRNA nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having four non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.,* 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to an eRNA nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an eRNA nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an eRNA nucleic acid, or specified portion thereof.

The antisense compounds provided also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds are complementary to at least an 11 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an eRNA nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds.

In certain embodiments, nucleosides comprise chemically modified ribofuranose ring moieties. Examples of chemically modified ribofuranose rings include without limitation, addition of substituent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'-OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—$C_1$-$C_{10}$ alkyl, OCF$_3$, OCH$_2$F, O(CH$_2$)$_2$SCH$_3$, O(CH$_2$)$_2$—O—N(R$_m$)(R$_n$), O—CH$_2$—C(=O)—N(R$_m$)(R$_n$), and O—CH$_2$—C(=O)—N(R$_1$)—(CH$_2$)$_2$—N(R$_m$)(R$_n$), where each $R_1$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-(CH$_2$)—O-2' (LNA); 4'-(CH$_2$)—S-2; 4'-(CH$_2$)$_2$—O-2' (ENA); 4'-CH(CH$_3$)—O-2' (also referred to as constrained ethyl or cEt) and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, $C_1$-$C_{12}$ alkyl, or a protecting group (see U.S. Pat. No. 7,427,672, issued on Sep. 23, 2008); 4'-CH$_2$—C—(H)(CH$_3$)-2' (see Chattopadhyaya et al., *J. Org. Chem.,* 2009, 74, 118-134); and 4'-CH$_2$—C(=CH$_2$)-2' (and analogs thereof see published International Application WO 2008/154401, published on Dec. 8, 2008).

Further reports related to bicyclic nucleosides can also be found in published literature (see for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U.S.A.,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 2007, 129(26) 8362-8379; Elayadi et al., *Curr. Opinion Invest. Drugs,* 2001, 2, 558-561; Braasch et al., *Chem. Biol.,* 2001, 8, 1-7; and Orum et al., *Curr. Opinion*

Mol. Ther., 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$)=C(R$_b$)—, —C(R$_a$)=N—, —C(=O)—, —C(=NR$_a$)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2',4'-(CH$_2$)$_2$-2', 4'-(CH$_2$)$_3$-2',4'-CH$_2$—O-2',4'-(CH$_2$)$_2$—O-2',4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA and (K) vinyl BNA as depicted below:

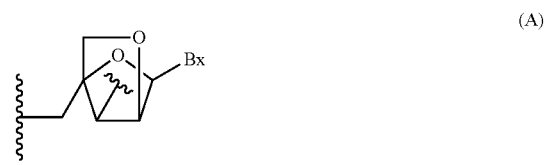

(A)

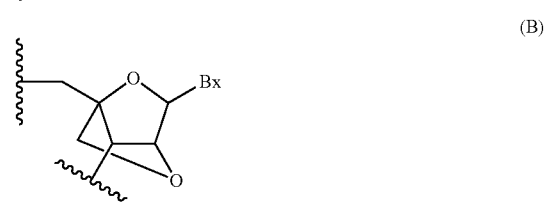

(B)

(C)

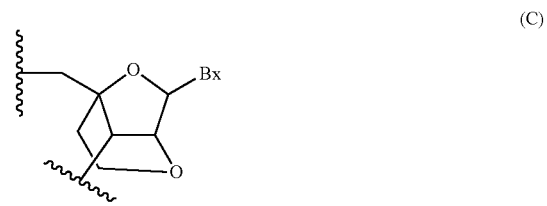

(D)

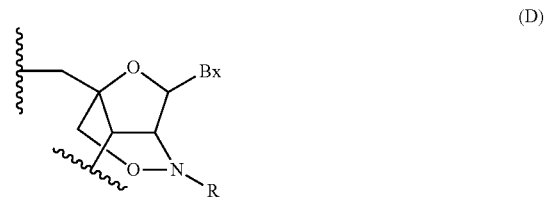

(E)

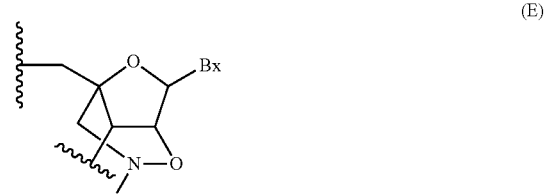

(F)

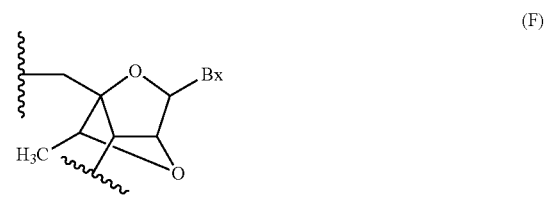

(G)

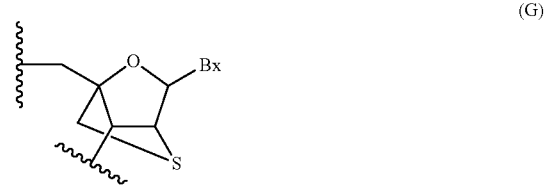

(H)

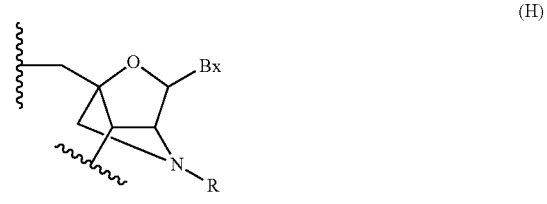

-continued

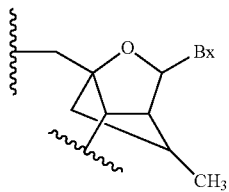
(I)

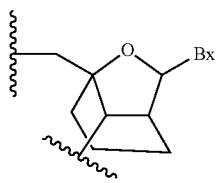
(J)

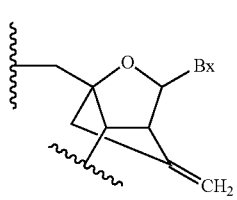
(K)

wherein Bx is the base moiety and R is independently H, a protecting group, $C_1$-$C_{12}$ alkyl or $C_1$-$C_{12}$ alkoxy.

In certain embodiments, bicyclic nucleosides are provided having Formula I:

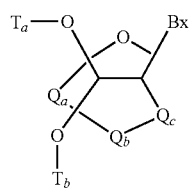
I wherein:
Bx is a heterocyclic base moiety;
-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O— or —N($R_c$)—O—$CH_2$;
$R_c$ is $C_1$-$C_{12}$ alkyl or an amino protecting group; and
$T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

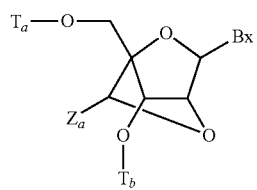
II wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

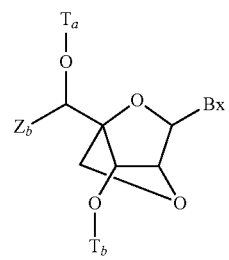
III wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

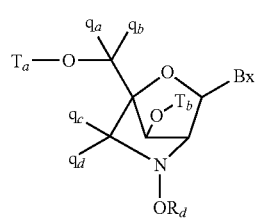
IV wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

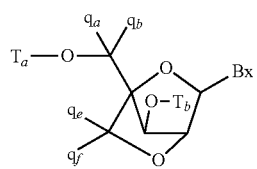

V wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)—$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

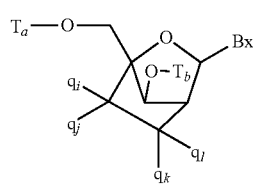

VI wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-($CH_2$)$_3$-2' bridge and the alkenyl analog bridge 4'-CH=CH—$CH_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[($CH_2$)$_n$O]$_m$$CH_3$, O($CH_2$)$_n$ $NH_2$, O($CH_2$)$_n$$CH_3$, O($CH_2$)$_n$F, O($CH_2$)$_n$$ONH_2$, $OCH_2$C(=O)N(H)$CH_3$, and O($CH_2$)$_n$ON[($CH_2$)$_n$$CH_3$]$_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., Chimia, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854) or fluoro HNA (F-HNA) having a tetrahydropyran ring system as illustrated below:

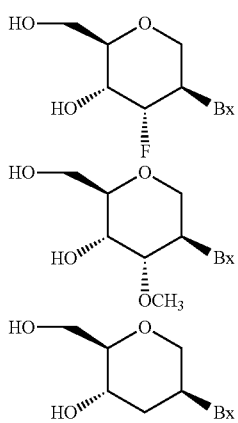

In certain embodiments, sugar surrogates are selected having Formula VII:

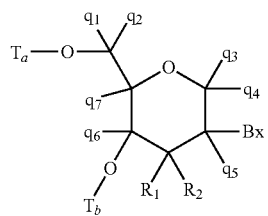

wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., *Biochemistry*, 2002, 41, 4503-4510; and U.S. Pat. Nos. 5,698,685; 5,166, 315; 5,185,444; and 5,034,506). As used here, the term "morpholino" means a sugar surrogate having the following formula:

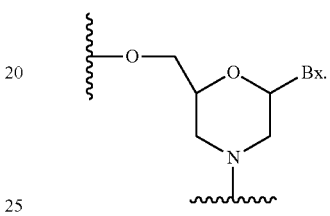

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horvath et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., *Acta Crystallographica, Section F: Structural Biology and Crystallization Communications*, 2005, F61(6), 585-586; Gu et al., *Tetrahedron*, 2004, 60(9), 2111-2123; Gu et al., *Oligonucleotides*, 2003, 13(6), 479-489; Wang et al., *J. Org. Chem.*, 2003, 68, 4499-4505; Verbeure et al., *Nucleic Acids Research*, 2001, 29(24), 4941-4947; Wang et al., *J. Org. Chem.*, 2001, 66, 8478-82; Wang et al., *Nucleosides, Nucleotides & Nucleic*

Acids, 2001, 20(4-7), 785-788; Wang et al., J. Am. Chem., 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

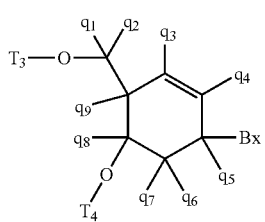

wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N$(R_m)(R_n)$, or O—$CH_2$—C($=$O)—N$(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, Bioorg. Med. Chem.,
2002, 10, 841-854). Such ring systems can undergo various additional substitutions to enhance activity.

Methods for the preparations of modified sugars are well known to those skilled in the art. Some representative U.S. patents that teach the preparation of such modified sugars include without limitation, U.S. Pat. Nos. 4,981,957; 5,118, 800; 5,319,080; 5,359,044; 5,393,878; 5,446,137; 5,466, 786; 5,514,785; 5,519,134; 5,567,811; 5,576,427; 5,591, 722; 5,597,909; 5,610,300; 5,627,053; 5,639,873; 5,646, 265; 5,670,633; 5,700,920; 5,792,847 and No.6,600,032 and International Application PCT/US2005/019219, filed Jun. 2, 2005 and published as WO 2005/121371 on Dec. 22, 2005, and each of which is herein incorporated by reference in its entirety.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH($CH_3$)—O-2') bridging group. In certain embodiments, the (4'-CH($CH_3$)—O-2') modified nucleosides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C$\equiv$C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties can also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds comprise one or more modified nucleobases. In certain embodiments, shortened or gap-widened antisense oligonucleotides comprise one or more modified nucleobases. In certain embodiments, the modified nucleobase is 5-methylcytosine. In certain embodiments, each cytosine is a 5-methylcytosine.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

In certain embodiments, antisense compounds, including, but not limited to those particularly suited for use as ssRNA, are modified by attachment of one or more conjugate groups. In general, conjugate groups modify one or more properties of the attached oligonucleotide, including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

For additional conjugates including those useful for ssRNA and their placement within antisense compounds, see e.g., U.S. Application No.; 61/583,963.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides may be mixed with LIPOFECTIN in OPTI-MEM 1 (Invitrogen, Carlsbad, Calif.) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that may range from 2 to 12 ug/mL per 100 nM antisense oligonucleotide.

Another technique used to introduce antisense oligonucleotides into cultured cells includes electroporation.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the Example 1

Determination of Genome-Wide Binding Profiles in Engineered RAW264.7 Macrophages To understand the mechanisms underlying Rev-Erb regulation of macrophage gene expression, genome-wide binding profiles in RAW264.7 macrophages engineered to contain biotin-tagged Rev-Erbα and Rev-Erbβ were determined. Rev-Erbα and Rev-Erbβ were tagged with biotin-ligase recognition peptide for in vivo biotinylation in RAW264.7 macrophages expressing biotin ligase from *E. coli* (Heinz, S. et al., Mol. Cell. 2010. 38: 576-589). Biotin-based or antibody-based Chromatin immunoprecipitation linked to deep sequencing (ChIP-Seq) was performed. ChIP-Seq indicated enrichment for both Rev-Erbα and Rev-Erbβ at the promoter of the circadian target gene BmalI. Previous studies (Preitner, N. et al., Cell. 2002. 110: 251-260; Yin, L. and Lazar, M. A. Mol. Endocrinol. 2005. 19: 1452-1459) have also demonstrated a high degree of overlap in the Rev-Erbα and Rev-Erbβ cistromes in several independent cell lines.

To focus on transcriptional programs common to Rev-Erbα and Rev-Erbβ, a core set of 2,079 of the highest confidence peaks occupied by both proteins was selected for detailed analysis. As seen in Table 1, the majority (~88%) of these peaks were in intra- and intergenic regions at least 1 kilobase away from annotated transcription start sites.

TABLE 1

Distribution of Rev-Erb localization relative to the nearest protein-coding genes.

|  | % |
|---|---|
| Promoter (1 kb-500 bp) | 10 |
| Intergenic | 49 |
| Exon | 2 |
| intron | 39 |

This was exemplified by intergenic Rev-Erb binding sites vicinal to the Mmp9 and Cxcr1 genes. In addition, 70% of Rev-Erb bound sites were in regions demarcated by high enrichment for H3K4me1 and low enrichment for H3K4me3, a histone signature for enhancer elements (Feng, D. et al., Science. 2011. 331: 1315-1319). De novo motif discovery of Rev-Erb-bound loci returned significant enrichment for binding sites for Rev-Erb, PU.1, AP1 and C/EBP, as presented in Table 2, with significant p-values and percentage of expected vs. observed instances of motifs.

TABLE 2

Top-enriched transcription factor motifs identified

| Transcription Factor | p-value | % observed | % expected |
|---|---|---|---|
| AP1 | 1e−449 | 31 | 4 |
| PU.1 | 1e−354 | 40 | 9 |
| Rev-Erb DR2 | 1e−174 | 7 | 1 |
| C/EBP | 1e−49 | 6 | 1 |

PU.1, AP-1 and C/EBP transcription factors are required for macrophage differentiation (Solt, L. A. et al., Nature. 2012. doi:10.1038/nature11030) and have recently been shown to establish the majority of the enhancer-like elements in macrophages (Fontaine, C. et al., Mol. Endocrinol. 2008. 22: 1797-1811). Co-localization of Rev-Erbs with PU.1 and C/EBP in macrophages was confirmed by comparison with direct binding data for these factors. Consistent with these findings, the Rev-Erb bound sites defined above localized to enhancer-like elements specific for macrophages, as defined by H3K4me1. The data is presented in Table 3, which shows the results of distribution of averaged ChIP-Seq signal of H3K4me1 at Rev-Erb bound H3K4me1$^{hi}$ H3K4me3$^{lo}$ (n=1,388) region in macrophages (Heinz, S. et al., Mol. Cell. 2010. 38: 576-589), B-cell (Lin, Y. C. et al., Nat. Immunol 2010. 11: 635), liver (Creyghton, M. P. et al., Proc. Natl. Acad. Sci. USA 2010. 107: 21931-21936), mouse embryonic stell cells (mES), and neural progenitor (NP)(Meissner, A. et al., Nature. 2008. 454: 766-770).

TABLE 3

Normalized Tag density in different cell types vs. distance from center of Rev-Erb bound enhancers

| Distance from Center (bp) | Macrophages | Liver | mES | NP | B Cell |
|---|---|---|---|---|---|
| −1800 | 0.17 | 0.06 | 0.07 | 0.05 | 0.10 |
| −1600 | 0.19 | 0.06 | 0.07 | 0.06 | 0.11 |
| −1400 | 0.21 | 0.06 | 0.07 | 0.06 | 0.12 |
| −1200 | 0.24 | 0.06 | 0.07 | 0.07 | 0.14 |
| −1000 | 0.28 | 0.07 | 0.07 | 0.07 | 0.15 |
| −800 | 0.35 | 0.08 | 0.07 | 0.08 | 0.17 |
| −600 | 0.41 | 0.09 | 0.08 | 0.09 | 0.20 |
| −400 | 0.48 | 0.09 | 0.08 | 0.10 | 0.22 |
| −200 | 0.40 | 0.11 | 0.08 | 0.11 | 0.22 |
| 0 | 0.18 | 0.11 | 0.08 | 0.10 | 0.18 |
| 200 | 0.40 | 0.10 | 0.08 | 0.10 | 0.22 |
| 400 | 0.48 | 0.10 | 0.08 | 0.10 | 0.23 |
| 600 | 0.42 | 0.08 | 0.08 | 0.08 | 0.20 |
| 800 | 0.34 | 0.08 | 0.07 | 0.08 | 0.18 |
| 1000 | 0.29 | 0.07 | 0.07 | 0.06 | 0.16 |
| 1200 | 0.24 | 0.07 | 0.07 | 0.06 | 0.14 |
| 1400 | 0.21 | 0.06 | 0.06 | 0.06 | 0.13 |
| 1600 | 0.19 | 0.06 | 0.06 | 0.06 | 0.12 |
| 1800 | 0.18 | 0.06 | 0.06 | 0.06 | 0.12 |

Example 2

Gene Expression Analysis in Wild-Type Macrophages and in Macrophages Deficient for Both Rev-Erbα and Rev-Erbβ

Gene expression analysis was performed in wild-type (WT) macrophages and macrophages deficient for both Rev-Erbα and Rev-Erbβ.

Bone marrow derived macrophages (BMDMs) and thio-glycollate-elicited (ThioMac) macrophages were generated from 4-6 week old Rev-Erbα$^{flox/flox}$; Rev-Erbβ$^{flox/flox}$ with or without Tie2-Cre as previously described (Huang, W. et al., Nature. 2011. 470: 414-418), Rev-Erb double knockout (DKO) macrophages were generated from bone marrow differentiation of Tie2-Cre; Rev-Erbα$^{flox/flox}$; Rev-Erbβ$^{flox/flox}$ animals (RevErb DKO) and were compared to control macrophages derived from Cre-negative littermates (WT). Tie2-Cre expression in hematopoietic stem cells (Schlaeger, T. M. et al., Blood. 2005. 105: 3871-3874) resulted in excision efficiencies in DKO macrophages of 85% of Rev-Erbα and 92% for Rev-Erbβ, as determined by Q-PCR.

Knockout of Rev-Erbβ dramatically increased Rev-Erbα expression. Excision of Rev-Erbα was estimated by comparing the depression between the floxed region versus a non-excised region.

Global Run-On sequencing (GRO-Seq) was performed to investigate the relationship between Rev-Erb binding sites and target genes. Preparation for GRO was performed as described previously (Wang, D. et al., Nature. 2011. doi: 10.1038/nature10006). GRO-Seq analysis indicated that 142 genes were significantly up-regulated in DKO macrophages (p-value<0.005), while 71 genes were down-regulated (p-value<0.005). The distance between transcription start sites of annotated genes to the nearest Rev-Erb peaks in all, up-, or down-regulated genes is presented in Table 4. The results indicate that genes that were up-regulated in DKO macrophages were significantly closer to Rev-Erb binding sites than down-regulated genes, consistent with the primary roles of Rev-Erbs as dedicated transcriptional repressors. However, only 3 of the 142 up-regulated genes had Rev-Erb peaks within 2 kb of annotated transcription start sites, suggesting that Rev-Erbs primarily act to repress gene expression at enhancer-like elements.

TABLE 4

Distance of nearest Rev-Erb peaks to TSS (bp in log2 scale) compared to gene expression in Rev-Erb DKO macrophages

| | Gene expression in Rev-Erb DKO | | |
|---|---|---|---|
| | All | Up-regulated genes | Down-regulated genes |
| average distance (bp) | 3181221 | 755558 | 3457211 |
| 1st quartile | 112798 | 45767 | 122946 |
| 3rd quartile | 998603 | 627405 | 1603662 |
| gene # | 24741 | 142 | 71 |

For expression analysis, RNA was harvested from macrophages using RNEasy kit (Qiagen), treated with Turbo-DNases (Ambion) and reverse-transcribed, using SuperScript III Reverse-Trasncriptase (Invitrogen) with random hexamers. Values determined for mRNA, using Quantitative reverse transcriptase-dependent PCR (Q-PCR), were normalized to 36B4 mRNA content from at least three independent experiments in triplicates. Quantitative reverse transcriptase-dependent PCR was used to validate GRO-Seq data in WT and DKO macrophages for the Mmp9 and Cx3cr1 genes at the level of mature mRNA. The results are presented in Table 5 and present the analysis in Rev-Erb DKO (WT=8 and DKO=7 in number) and Rev-Erbα (control=17 and alpha phenotype=18 independent lines), or Rev-Erbβ (control=13 and beta phenotype=18 independent lines) over-expressing macrophages. Statistical significance was determined by two tail Student's t-test. P-value is represented as ** for P<0.01 and by § for P<0.05 versus the control. Mature mRNA for both genes was significantly increased in the Rev-Erb DKO macrophages. Conversely, constitutive expression of either Rev-Erbα or Rev-Erbβ in RAW264.7 macrophages resulted in repression of Mmp9 and Cx3cr1 expression.

TABLE 5

Q-PCR analysis of relative normalized expression of Mmp9 and Cx3cr1 mRNA in Rev-Erb DKO and Rev-Erbα or Rev-Erbβ overexpressing macrophages

| | Mmp9 | Cx3cr1 |
|---|---|---|
| WT | 0.43 | 0.19 |
| DKO | 1.65§ | 1.93§ |
| Control | 1.72 | 1.18 |
| Rev-Erbα | 0.32** | 0.83§ |
| Control | 1.69 | 1.26 |
| Rev-Erbβ | 0.50** | 0.81** |

By evaluating multiple independent clones, the extent of Mmp9 and Cx3cr1 repression was observed to be inversely correlated with Rev-Erb expression levels. The data was generated by Q-PCR analysis of Mmp9 and Cx3cr1 mRNA expression in independent RAW264.7 macrophage cell lines expressing Rev-Erbα (n=17), Rev-Erbβ (n=18), or empty expression vector. The data was found to be statistically significant, as determined by Spearman rank correlation test.

Example 3

Testing of Genomic Regions Containing Rev-Erb Binding Sites for Enhancer Activity A 983 bp region surrounding the Rev-Erb-bound site at −5 kb from the Mmp9 transcription start site (TSS) was cloned downstream of a luciferase reporter driven by a TATA-like promoter. The region was cloned into a pGL4-based reporter and tested in RAW264.7, as described previously (Heinz, S. et al., Mol. Cell. 2010. 38: 576-589). The presence of this Rev-Erb-containing region increased reporter gene activity in RAW264.7 macrophages, while a control genomic region devoid of Rev-Erb binding sites or other enhancer-like features did not. This enhancer activity was also sensitive to Rev-Erb repression, as determined by luciferase reporter activity.

Sequencing libraries were prepared by ligating separate modified single-stranded adapters to 3' and 5'-RNA ends using mutant (K227Q) truncated RNA ligase 2 (NEB) and RNA ligase 1, respectively, reverse-transcribed with SuperScript III reverse transcriptase (Invitrogen), and PCR-amplified with primers bearing primer landing sites compatible with Illumina sequencing. RAR-related orphan nuclear receptors (RORs) also bind to Rev-Erb response elements and constitutively activate gene expression (Giguere, V et al., Genes Dev. 1994. 8: 538-553). Consistent with this, constitutive expression of RORα increased activity of the Mmp9 enhancer element. Co-expression of wild type Rev-Erbβ, but not Rev-Erbβ with a mutation disrupting sequence-specific DNA binding, antagonized RORα activation. For this assay, luciferase activity of reporters containing Rev-Erb bound enhancer from the genomic regions was measured after co-transfection of RORα and Rev-Erbα or Rev-Erbβ with mutation in the DNA binding domain. BmaII promoter was used as the positive control. A 1 kb genomic region without enhancer-like element was used as a negative control. Data generated was the mean of at least 3 independent experiments and was found to be statistically significant, as determined by one-way ANOVA followed by Tukey HSD test.

Similar experiments were performed for six other Rev-Erb-bound distal regions, all of which were sensitive to RORα activation. Four of the six could be antagonized by Rev-Erb co-transfection. Collectively, these findings suggest that Rev-Erbs confer a macrophage-specific program of repression by regulating the activities of enhancers that are established by collaborative interactions between macrophage lineage-determining transcription factors, such as PU.1 and C/EBPs, and signal-dependent factors, such as RORs.

Among the 2,079 common Rev-Erb binding sites, 1,388 loci were located at least ±1 kb from annotated transcription start sites and were associated with the enhancer histone signature H3K4me1$^{hi}$/H3K4me3$^{lo}$. ChIP-sequencing experiments indicated that many of these sites were co-enriched for the engaged, serine-5 phosphorylated RNA Polymerase II (RNAPII). The data was derived from a cluster plot of ChIP-Seq signal for H3K4me1, H3K4me3, and serine-5 phosphorylated RNA polymeriase II (RNAPII) at 1,388 Rev-Erb bound, H3K4me1$^{hi}$H3K4me3l$^{o}$ regions.

In addition, examination of GRO-Seq data at these sites indicated the presence of bidirectional RNA transcription, consistent with recent studies indicating that RNAs are transcribed from distal enhancer elements on a genome-wide scale (Kim, T.-K. et al., Nature. 2010. 465: 182; Wang, D. et al., Nature. 2011. doi:10.1038/nature10006; Hah, N. et al., Cell. 2011. 145: 622-634). The data is presented in Table 6 as the distribution of averaged macrophage GRO-Seq eRNA signal flanking Rev-Erb intergenic sites defined in macrophages (n=722) and liver (n=521). No significant RNA signal was detected from the locations of intergenic Rev-Erbα peaks defined in liver (Feng, D. et al., Science. 2011. 331: 1315-1319), indicating that RNA expression at distal regulatory elements is cell-type specific.

Using GRO-Seq, analysis of averaged RNA signal distribution from the 100 highest enriched Rev-Erb bound intergenic enhancers indicated an overall increase of RNA signal in Rev-Erb DKO macrophages compared to WT control. Conversely, overexpression of Rev-Erbα resulted in decreased eRNA expression at the most confident Rev-Erb binding sites. To precisely define the eRNA start sites, the GRO-Seq protocol was modified to detect nascent RNA with a 5' 7-methylguanylated cap (5'GROseq), thus focusing on detecting transcriptional events at initiation sites. 5'GRO-Seq was performed with the following modifications from the GRO-Seq protocol (Wang, D. et al., Nature. 2011. doi:10.1038/nature10006). Briefly, GRO-RNA was 3' and 5'-dephosphorylated with polynucleotide kinase (Enzymatics) and calf intestinal phosphatase (NEB), respectively, and then capped fragments were de-capped with tobacco acid pyrophosphatase (Epicentre) to leave 5' phosphates. Analysis of averaged RNA signal distribution at the top 100 Rev-Erb intergenic enhancers showed a striking decrease of eRNA initiation in macrophages overexpressing Rev-Erbα compared to control macrophages. The data is presented in Tables 7 and 8. Table 7 presents the distribution of averaged GRO-Seq eRNA signal from Rev-Erb DKO and control BMDM at the top 100 Rev-Erb bound intergenic sites. Table 8 shows the distribution of average 5' capped RNA (5' GRO-Seq) signal from Rev-Erbα overexpressing and control RAW264.7 macrophages flanking the top 100 Rev-Erb-bound intergenic sites.

TABLE 6

Distribution of macrophage GRO-Seq eRNA signal flanking Rev-Erb intergenic sites in macrophages and liver

| distance from Rev-Erb intergenic sites (bp) | macrophages | | Liver | |
|---|---|---|---|---|
| | Rev-Erbα Plus | Rev-Erbα Minus | Rev-Erbα Plus | Rev-Erbα Minus |
| −1820 | 0.0028 | 0.0025 | 0.0010 | 0.0007 |
| −1700 | 0.0031 | 0.0028 | 0.0011 | 0.0007 |
| −1500 | 0.0032 | 0.0030 | 0.0010 | 0.0008 |
| −1300 | 0.0032 | 0.0033 | 0.0009 | 0.0007 |
| −1100 | 0.0031 | 0.0041 | 0.0010 | 0.0008 |
| −900 | 0.0030 | 0.0052 | 0.0010 | 0.0009 |
| −700 | 0.0030 | 0.0066 | 0.0009 | 0.0010 |
| −500 | 0.0031 | 0.0076 | 0.0009 | 0.0013 |
| −300 | 0.0036 | 0.0087 | 0.0009 | 0.0014 |
| −100 | 0.0042 | 0.0071 | 0.0011 | 0.0014 |
| −20 | 0.0054 | 0.0059 | 0.0012 | 0.0013 |
| 20 | 0.0060 | 0.0053 | 0.0012 | 0.0013 |
| 100 | 0.0070 | 0.0039 | 0.0013 | 0.0012 |
| 300 | 0.0087 | 0.0033 | 0.0012 | 0.0009 |
| 500 | 0.0079 | 0.0032 | 0.0010 | 0.0009 |
| 700 | 0.0071 | 0.0030 | 0.0011 | 0.0009 |
| 900 | 0.0055 | 0.0030 | 0.0010 | 0.0009 |
| 1100 | 0.0046 | 0.0030 | 0.0008 | 0.0009 |
| 1300 | 0.0039 | 0.0027 | 0.0010 | 0.0009 |
| 1500 | 0.0032 | 0.0026 | 0.0011 | 0.0009 |
| 1700 | 0.0028 | 0.0026 | 0.0009 | 0.0009 |
| 1820 | 0.0026 | 0.0026 | 0.0007 | 0.0008 |

Example 4

Determination of the Role of Rev-Erbs in Regulating Enhancer-RNA (eRNA) Expression To determine whether Rev-Erbs regulate eRNA expression, transcription of nascent RNA at Rev-Erb bound enhancers was examined in both loss of function and gain of function models.

TABLE 7

Distribution of averaged GRO-Seq eRNA signal from Rev-Erb DKO and control BMDM

| distance from center of Rev-Erb sites (bp) | Wild type | | DKO | |
|---|---|---|---|---|
| | plus | minus | plus | minus |
| −1820 | 0.002 | 0.003 | 0.003 | 0.003 |
| −1700 | 0.003 | 0.003 | 0.003 | 0.003 |
| −1500 | 0.003 | 0.003 | 0.003 | 0.003 |
| −1300 | 0.003 | 0.004 | 0.003 | 0.004 |
| −1100 | 0.002 | 0.005 | 0.003 | 0.006 |
| −900 | 0.002 | 0.006 | 0.003 | 0.008 |
| −700 | 0.003 | 0.008 | 0.004 | 0.009 |
| −500 | 0.004 | 0.008 | 0.004 | 0.009 |
| −300 | 0.004 | 0.009 | 0.004 | 0.011 |
| −100 | 0.004 | 0.009 | 0.005 | 0.010 |
| −20 | 0.005 | 0.008 | 0.007 | 0.008 |
| 20 | 0.006 | 0.007 | 0.007 | 0.008 |
| 100 | 0.007 | 0.005 | 0.008 | 0.006 |
| 300 | 0.009 | 0.004 | 0.010 | 0.005 |
| 500 | 0.008 | 0.004 | 0.009 | 0.005 |
| 700 | 0.008 | 0.004 | 0.009 | 0.004 |
| 900 | 0.006 | 0.003 | 0.008 | 0.003 |
| 1100 | 0.005 | 0.003 | 0.007 | 0.003 |
| 1300 | 0.004 | 0.002 | 0.005 | 0.003 |
| 1500 | 0.004 | 0.003 | 0.004 | 0.004 |
| 1700 | 0.003 | 0.004 | 0.004 | 0.004 |
| 1820 | 0.003 | 0.003 | 0.003 | 0.004 |

TABLE 8

Distribution of 5'GRO-Seq eRNA signal from Rev-Erbα macrophages and control macrophages flanking Rev-Erb-bound intergenic sites

| distance from center of Rev-Erb sites (bp) | Control | | Rev-Erb | |
|---|---|---|---|---|
| | plus | minus | plus | minus |
| −480 | 0.034 | 0.027 | 0.013 | 0.016 |
| −400 | 0.032 | 0.044 | 0.021 | 0.018 |

TABLE 8-continued

Distribution of 5'GRO-Seq eRNA signal from Rev-Erbα macrophages and control macrophages flanking Rev-Erb-bound intergenic sites

| distance from center of Rev-Erb sites (bp) | Control plus | Control minus | Rev-Erb plus | Rev-Erb minus |
|---|---|---|---|---|
| −300 | 0.032 | 0.050 | 0.026 | 0.031 |
| −200 | 0.015 | 0.078 | 0.008 | 0.044 |
| −100 | 0.020 | 0.309 | 0.012 | 0.172 |
| −10 | 0.175 | 0.169 | 0.108 | 0.120 |
| 0 | 0.198 | 0.148 | 0.117 | 0.109 |
| 10 | 0.245 | 0.161 | 0.153 | 0.107 |
| 100 | 0.242 | 0.032 | 0.162 | 0.027 |
| 200 | 0.114 | 0.017 | 0.055 | 0.013 |
| 300 | 0.058 | 0.047 | 0.030 | 0.025 |
| 400 | 0.045 | 0.015 | 0.026 | 0.006 |
| 480 | 0.055 | 0.011 | 0.033 | 0.005 |

In either loss or gain of function experiment, the eRNA signal at the global set of PU.1-bound enhancers showed no significant changes, as presented in Table 9, indicating that the changes in eRNA are specific to Rev-Erb-bound enhancer elements. Table 9 presents the distribution of average 5' capped RNA (5'GRO-Seq) signal from Rev-Erbα overexpressing and control RAW264.7 macrophages flanking the top 100 PU.1-bound intergenic sites.

TABLE 9

Distribution of 5'GRO-Seq eRNA signal from Rev-Erbα macrophages and control macrophages flanking PU.1-bound intergenic sites

| distance from center of PU.1 sites (bp) | Control plus | Control minus | RevErbα plus | RevErbα minus |
|---|---|---|---|---|
| −480 | 0.027 | 0.023 | 0.020 | 0.018 |
| −400 | 0.015 | 0.029 | 0.010 | 0.026 |
| −300 | 0.034 | 0.035 | 0.036 | 0.033 |
| −200 | 0.012 | 0.049 | 0.009 | 0.074 |
| −100 | 0.013 | 0.199 | 0.014 | 0.188 |
| −10 | 0.105 | 0.163 | 0.097 | 0.161 |
| 0 | 0.152 | 0.127 | 0.161 | 0.129 |
| 10 | 0.180 | 0.085 | 0.189 | 0.079 |
| 100 | 0.225 | 0.013 | 0.233 | 0.019 |
| 200 | 0.059 | 0.013 | 0.050 | 0.020 |
| 300 | 0.046 | 0.018 | 0.039 | 0.017 |
| 400 | 0.022 | 0.015 | 0.022 | 0.014 |
| 480 | 0.013 | 0.010 | 0.012 | 0.013 |

Moreover, the de-repression level of eRNA in Rev-Erb DKO is inversely correlated to eRNA repression level upon constitutive expression of Rev-Erbα (p=−0.39, p-value=0.008), indicating a strong agreement between the experimental sets. For this assay, 53 Rev-Erb bound enhancers with de-repressed eRNA expression in Rev-Erb DKO macrophages was plotted against changes of eRNA level upon overexpression of Rev-Erbα in RAW264.7 macrophages. Changes in eRNA was determined by the $\log_2$ difference of expression between DKO and WT macrophages, or between Rev-Erbα over-expressing and control macrophages. The data was considered statistically significant, as determined by Spearman rank correlation test.

GRO-Seq results indicating Rev-Erb mediated negative regulation of eRNA expression were confirmed using RT-PCR for eRNA of Mmp9 −5 kb and Cx3cr1 28 kb enhancers. Q-PCR analysis of the −5 kb Mmp9 and 28 kb Cx3cr1 enhancer RNA in Rev-Erb DKO (wild type=6) and DKO-5 in number) and Rev-Erbα overexpressing RAW264.7 macrophages (control=13 and alpha=14 independent cell lines) are presented in Table 10. The statistical significance was determined by two tail Student's t-test where * represents $P<0.01$ and § represents $P<0.05$, versus the control.

TABLE 10

Relative expression of Mmp9 and Cx3cr1 enhancer RNA

|  | Mmp9 eRNA | Cx3cr1 eRNA |
|---|---|---|
| WT | 0.67 | 0.33 |
| DKO | 1.38* | 1.75§ |
| Control | 1.37 | 1.37 |
| Rev-Erb | 0.65 | 0.66§ |

To investigate mechanisms by which Rev-Erbs regulate eRNA expression, the effects of gain and loss of Rev-Erb function on enhancer assembly and histone modification were evaluated. ChIP-Seq experiments demonstrated increased H3K9 acetylation (H3K9ac) at Rev-Erb-occupied enhancers in DKO macrophages and reduced H3K9ac enrichment in macrophages with constitutively expressed Rev-Erbα. H3K9ac enrichment was not changed at the global set of PU.1-enhancers, consistent with Rev-Erb-mediated recruitment of NCoR/HDAC3 complexes mediating local deacetylation of H3K9 (Yin, L. and Lazar, M. A. Mol. Endocrinol. 2005. 19: 1452-1459). The assay measured the average distribution of H3K9ac ChIP-Seq signal flanking 53 Rev-Erb bound enhancers or the top 500 enriched PU.1 bound enhancers for WT and Rev-Erb DKO macrophages. The assay also measured the same parameters for 266 Rev-Erb bound enhancer which have repressed eRNA expression or the top 500 enriched PU.1 bound enhancer for control and Rev-Erbα overexpressing RAW264.7 macrophages.

In contrast, constitutive expression of Rev-Erbα had no significant effect on H3K4me1 or PU.1 enrichment at Rev-Erb bound enhancer elements, despite the profound changes in eRNA initiation. The assay measured the average distribution of PI.1 and H3K4me1 and ChIP-Seq signal flanking the 266 Rev-Erb bound enhancers with repressed eRNA level upon overexpression of Rev-Erbα.

Collectively, these results raise the possibility that Rev-Erbs repressed gene expression at a distance by regulating enhancer-directed transcription. Consistent with this possibility, changes in eRNA expression at Rev-Erb-bound sites due to gain or loss of Rev-Erb function were correlated with changes in expression of the nearest mRNA.

Example 5

Determination of the Role of eRNA Activity In Vitro

Even though levels of eRNA are low at steady state (Kim, T.-K. et al., Nature. 2010. 465: 182), transcriptional initiation from enhancers, as measured by 5' GRO-Seq, was often comparable to that at promoters of protein-coding genes, as exemplified by Cx3cr1 and Mmp9, suggesting robust production of short-lived transcripts. Three experimental approaches were used to investigate whether the synthesis of enhancer-directed RNA transcripts contributed to enhancer activity.

First, RNA interference (RNAi) was utilized to target eRNA transcripts of Mmp9 and Cx3cr1. Non-targeting siRNA oligos or siRNA directed against Mmp9 and Cxcr1 eRNA (Dharmacon) were transfected using DeliverX (Affymetrix) or LipofectAMINE2000® (Invitrogen) into Thio- Mac or BMDM, respectively. siRNAs were identified that specifically reduced expression of eRNAs associated with the Mmp9 or Cx3cr1 enhancers in primary WT macrophages. Q-PCR analysis of Mmp9 eRNA, Mmp9 mRNA and NCoA5 (negative control) for WT and Rev-Erb DKO ThioMac transfected with control or Mmp9 eRNA siRNA (WT=4 and DKO=4 in number) was conducted. The results are presented in Table 11. Q-PCR analysis was also conducted of Cx3cr1 eRNA, Cxc3cr1 mRNA and Csrnp1 (negative control) for WT and Rev-Erb DKO BMDM transfected with siRNA targeting Cx3cr1 eRNA (WT=6 and DKO=5 in number). The results are presented in Table 12. The results demonstrate the reduction in eRNA expression was associated with a corresponding reduction of Mmp9 and Cx3cr1 mRNAs, but not mRNAs from the nearest expressing genes such as NCoA5 and Csrnp1, respectively. Furthermore, these siRNAs reversed the de-repression phenotype associated with increased eRNA expression in Rev-Erb DKO macrophages.

TABLE 11

Relative expression of Mmp9 eRNA and mRNA after treatment with siRNA

| | | Mmp9 eRNA | Mmp9 mRNA | NCoA5 |
|---|---|---|---|---|
| Control siRNA | WT | 0.4 | 1.1 | 0.8 |
| siRNA to Mmp9 eRNA | WT | 0.3 | 0.4 | 0.8 |
| Control siRNA | DKO | 1.3 | 2.0 | 0.8 |
| siRNA to Mmp9 eRNA | DKO | 0.5 | 0.4 | 1.0 |

TABLE 12

Relative expression of Cx3cr1 eRNA and mRNA after treatment with siRNA

| | | Cx3cr1 eRNA | Cx3cr1 mRNA | CsrnpI |
|---|---|---|---|---|
| Control siRNA | WT | 0.8 | 0.3 | 0.9 |
| siRNA to Cx3cr1 eRNA | WT | 0.2 | 0.1 | 0.9 |
| Control siRNA | DKO | 2.1 | 2.5 | 1.0 |
| siRNA to Cx3cr1 eRNA | DKO | 0.9 | 1.4 | 1.2 |

As a second approach, chemically modified antisense oligonucleotides (ASO) were utilized to knock down the plus strand Mmp9 −5 kb eRNA. Seventy seven overlapping ASOs targeting the proximal 450 bp of the plus-strand Mmp9 −5 kb eRNA were systematically screened and the most effective ASOs were selected for detailed analysis.

ISIS 566237 is an oligonucleotide with deoxy, MOE and (S)-cEthyl units with a sequence 5'-ATTGTGTGAC-CCCAGC-3' (SEQ ID NO:3) and a chemistry notation 5'-Aes Tes Tks Gds Tds Gds Tds Gds Ads mCds mCds mCds mCds Aks Gks mCe-3' (e=2'-O-methoxyethyl ribose; s=thioate ester; k=(S)-cEt; d=2'-deoxyribose). ISIS 566237 is targeted to an Mmp9 eRNA sequence, SEQ ID NO: 1 (GENBANK Accession No. NT_039207.7 truncated from 105809972 to 105810309). ISIS 566237 targets SEQ ID NO: 1 at nucleotides 247 to 262.

ISIS 566241 is an oligonucleotide with deoxy, MOE and (S)-cEthyl units with a sequence 5'-CAAGCTTCAGCT-CATT-3' (SEQ ID NO:4) and a chemistry notation 5'-mCes Aes Aks Gds mCds Tds Tds mCds Ads Gds mCds Tds mCds Aks Tks Te-3' (e=2'-O-methoxyethyl ribose; s=thioate ester; k=(S)-cEt; d=2'-deoxyribose). ISIS 566241 is targeted to an Mmp9 eRNA sequence, SEQ ID NO: 1 at nucleotides 260 to 275.

ISIS 129700 is a 5-10-5 MOE gapmer and is 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout the gapmer are phosphorothioate (P=S) linkages. All cytosine residues throughout the gapmer are 5-methylcytosines. ISIS 129700 has the sequence 5'-TAGTGCGGACCTAC-CCACGA-3' (SEQ ID NO: 5) and does not target any known murine target. Hence, it was used as a negative control.

ISIS 535522 is a 5-10-5 MOE gapmer with a sequence 5'-GCACCTTTCCCTCGGATGGG-3' (SEQ ID NO: 6) and is targeted to the murine Mmp9 mRNA sequence (GEN-BANK Accession No. NM_013599.2) (SEQ ID NO:203) at nucleotides 2275 to 2294. ISIS 535522 also served as a control in the assay.

The ASOs were transfected into ThioMac using Cytofectin (Gene Therapy System). The results of the Q-PCR analysis of Mmp9 eRNA expression in thioglycollate-elicited primary macrophages transfected with ASOs are presented in Table 13. Both ISIS 566237 and ISIS 566241 reduced eRNA expression. Statistical significance was determined by one-way ANOVA with Tukey HSD test. In case of the P value, * represents P<0.05 and § represents P<0.005, versus the control.

TABLE 13

Relative expression of Mmp9 eRNA and mRNA after treatment with ASOs

| | % inhibition |
|---|---|
| ISIS 129700 | 0 |
| ISIS 566237 | 15* |
| ISIS 566241 | 42§ |

Furthermore, titrating the concentration of ASO resulted in dose dependent reduction of the corresponding Mmp9 mRNA. Table 14 presents the Q-PCR analysis of Mmp9 mRNA expression in ThioMac transfected with titrated concentration of ASO (n=3 per condition).

TABLE 14

Dose-dependent inhibition of Mmp9 mRNA after treatment with ASOs

| | ISIS No | Dose (nM) | % inhibition |
|---|---|---|---|
| ASO targeting Mmp9 eRNA | 566237 | 12.5 | 0 |
| | 566237 | 25 | 0 |
| | 566237 | 50 | 10 |
| | 566237 | 100 | 45 |
| | 566237 | 200 | 54 |
| ASO targeting Mmp9 eRNA | 566241 | 12.5 | 0 |
| | 566241 | 25 | 0 |
| | 566241 | 50 | 9 |
| | 566241 | 100 | 55 |
| | 566241 | 200 | 49 |
| ASO targeting Mmp9 mRNA | 535522 | 100 | 88 |

As a third approach, the functional significance of the Mmp9 −5 kb eRNAs was examined using the enhancer reporter assay guided by the definition of eRNA start sites provided by 5'GRO-Seq. The 983 bp sequence upstream of Mmp9 that conferred Rev-Erb-regulated enhancer activity in RAW264.7 cells encompassed a 388 bp central region of open chromatin containing the binding sites for PU.1, C/EBPs, AP-1 and Rev-Erbs, as well as start sites of the plus and minus-strand eRNAs. The 983 bp of the Mmp9 enhancer was cloned downstream of the luciferase reporter gene driven by the Mmp9 promoter. The luciferase activity of the enhancer reporter driven by Mmp9 promoter containing the indicated DNA fragments and transfected in RAW264.7 macrophages (n=8) was measured and is presented in Table 15. The 388 bp core was significantly less active than the 983 bp sequence, which encoded the eRNAs. Statistical significance was determined by one-way ANOVA followed by Tukey HSD test. In case of the value, § represents P<0.005 versus all other indicated conditions.

TABLE 15

Relative promoter activity of the Mmp9 enhancer

|  | activity |
| --- | --- |
| Random 1kb | 0.14 |
| Mmp9 enhancer 983 bp | 1.96§ |
| Mmp9 enhancer 388 bp | 0.90 |

Expression of the plus-strand eRNA from the 983 bp enhancer was confirmed by RT-PCR of Mmp9 plus eRNA normalized to the copy number of the transfected plasmid DNA using reporter-specific primer for first strand cDNA synthesis. Enhancer reporter assays were performed as described above with different DNA fragments cloned in the luciferase reporter and the data is presented in Table 16. Addition of DNA encoding the plus-strand eRNA to the core enhancer, but not the DNA encoding the minus strand eRNA, restored transcriptional activity. Statistical significance was determined by one-way ANOVA followed by Tukey HSD test. In case of the P value, § represents P<0.005 versus all other indicated conditions.

In another experiment, 983 bp of the Mmp9 enhancer was cloned downstream of the luciferase reporter gene driven by the Mmp9 promoter in the opposite orientation from that used in the study above. Enhancer reporter constructs driven by Mmp9 promoter containing the DNA fragments were transfected into RAW264.7 macrophages. A similar activity of the plus strand eRNA was observed when the 1 kb or core enhancer elements were inserted in the reverse orientation.

TABLE 16

Relative promoter activity of the Mmp9 enhancer

|  |  | Activity |
| --- | --- | --- |
| Mmp9 enhancer 388 bp |  | 0.77 |
| Plus eRNA | WT | 1.91§ |
|  | Flipped | 0.70 |
| Minus eRNA | WT | 0.84 |
|  | Flipped | 0.79 |

These observations were consistent with the finding that siRNAs and ASOs directed against the plus-strand eRNA resulted in reduction of Mmp9 mRNA expression. These findings also suggested that either the eRNA sequence is an important determinant of enhancer function, or the sequences encoding the plus strand eRNA contain binding sites for additional transcription factors that contribute to enhancer activity.

To address this question, the orientation of the sequences encoding the plus strand eRNA enhancer was inverted relative to the 388 bp-core. This strategy would retain any putative transcription factor binding sites but completely change the sequence of any potential eRNA product. In the "flipped" construct, enhancer activity was reduced to a level comparable to the 388 bp-enhancer construct despite production of eRNA from an alternative start site. Collectively, these data suggest that the DNA element encoding the plus eRNA contributes to Mmp9 enhancer activity.

Example 6

Determination of the Role of eRNA Activity In Vivo

The findings of the studies described above raised the question of whether enhancers might be considered as targets for cell-specific manipulation of gene expression in vivo. To explore this possibility, sterile peritonitis was induced in mice and the ability of siRNAs directed against the Mmp9 −5 kb plus strand eRNA to alter Mmp9 mRNA expression was investigated. Thioglycollate-elicited sterile peritonitis and in vivo RNAi assays were performed as described in previous studies (Huang, W. et al., Nature. 2011. 470: 414-418). Briefly, 2 ml thioglycollate medium was delivered to each animal by intraperitoneal injection on day 1. On day 2, 100 µg scrambled control siRNAs or Mmp9 eRNA-specific siRNA was complexed in LipofectAMINE2000 ® and serum-depleted medium (in 1 ml final volume) and delivered to animals by intraperitoneal injection. Elicited macrophages in the peritoneal cavities were collected with 10 ml of PBS on day 4 for RNA analysis (n=8 per condition). Values were normalized to the average of 36B4 and Cyclophilin A mRNA. Statistical significance was determined by two tail Student's t-test. In case of the P value, * represents P<0.05 versus the control siRNA. The results are presented in Table 17 and indicate that the eRNA-specific siRNA, but not a control siRNA, reduced expression of the −5 kb plus strand eRNA and the Mmp9 primary transcript, but not the NCoA5 mRNA, as was observed in primary macrophages in vitro. Cx3cr1 mRNA was also measured as a negative control.

TABLE 17

Relative RNA expression in mice

|  | control siRNA | siRNA to Mmp9 eRNA |
| --- | --- | --- |
| Mmp9 eRNA | 1.17 | 0.83 |
| Mmp9 pre-mRNA | 1.21 | 0.79 |
| NcoA5 | 1.07 | 0.93 |
| Cx3cr1 | 1.05 | 0.95 |

Example 7

Role of eRNAs in Enhancer-Dependent Activation of Coding Genes Regulated by Sex Steroid Receptors The role of eRNAs in the enhancer-dependent activation of coding genes regulated by sex steroid receptors was studied by performing experiments designed to determine whether liganded estrogen receptors induce eRNA transcription on ERα-bound enhancers.

MCF-7 cells were initially obtained from ATCC and were incubated in α-MEM media supplemented with 10% FBS in a 7% $CO_2$ humidified incubator. Once the cells reached 60% confluency, they were hormone-stripped for 3 days by culturing in phenol-free media plus charcoal-depleted FBS. The cells were treated or not with 100 nM Estradiol ($E_2$) for 1 hr to induce estrogen signaling (Prasanth, K. V. and Spector, D. L. Genes Dev. 2007. 21: 11-42).

A ChIP-seq analysis (>100×10$^6$ uniquely mapped reads) of ERα binding sites was performed, as previously described (Wang, D. et al., Nature. 2011. 474: 390-394). Briefly, approximately 10$^7$ treated cells were cross-linked with 1% formaldehyde at room temperature for 10 min. After sonication, the soluble chromatin was incubated with 1-5 µg of antibody (HC-20 and H-184, Santa Cruz Biotechnology) at 40° C. overnight. Immunoprecipitated complexes were collected using Dynabeads A/G (Invitrogen). Subsequently, immunocomplexes were washed, DNA extracted and purified by QIAquick Spin columns (Qiagen). The extracted DNA was ligated to specific adaptors, followed by deep sequencing with the Illumina HiSeq 2000 system, according to the manufacturer's instructions. The first 48 bp for each sequence tag returned by the Illumina pipeline was aligned to the hg18 assembly (National Center for Biotechnology Information, build 36.1), using BFast, allowing up to two mismatches. Only uniquely mapped tags were selected for further analysis.

The data was visualized by preparing custom tracks on the University of California, Santa Cruz genome browser, using HOMER (biowhat.ucsd.edu/homer) (Heinz, S. et al., Mol. Cell. 2010. 38: 576-589). Given that the peak distribution of transcription factors and histone marks were markedly different, parameters were optimized for the narrow tag distribution characteristic of transcription factors by searching for high read density regions with a 200 bp sliding window. Regions of maximal density exceeding a given threshold were called 'peaks', and it was required for adjacent peaks to be at least 500 bp away to avoid redundant detection. The common artifacts derived from clonal amplification were circumvented by considering only one tag from each unique genomic position, as determined from the mapping data. The threshold for the number of tags that determined a valid peak was selected at a false discovery rate of 0.001, determined by peak finding using randomized tag positions in a genome with an effective size of 2×10$^9$ bp. It was also required for peaks to have at least four-fold more tags (normalized to total count) than input control samples. In addition, it was required to obtain four-fold more tags relative to the local background region (10 kb) to avoid identifying regions with genomic duplications or non-localized binding.

In the case of histone marks, the parameters were modified to search for enrichment in wide genomic segments as, unlike transcription factors, they can occupy large segments in the magnitude of several kb. Seed regions were initially found using a peak size of 500 bp at a false discovery rate of 0.001 to identify enriched loci. Enriched regions separated by 1 kb were merged and considered as blocks of variable lengths. All called peaks meeting the criteria established for transcription factors and histone marks were then associated with genes by cross-referencing the RefSeq TSS database as available in the UCSC genome browser. Peaks from individual experiments were considered equivalent if their peak centers were located within 200 bp.

The analysis (>100×10$^6$ uniquely mapped reads) of ERα binding sites using vehicle or $E_2$-treated MCF-7 breast cancer cells increased the number of known genomic ERα binding sites three-fold, to 23,255, genome-wide. In this robust analysis, ERα was found to preferentially bind distal intergenic (53%) and intronic sites (39%), with only 3% being bound to promoters, suggesting that ERα is able to exert transcriptional effects based on binding to genomic elements other than the regulated coding gene promoters. A corresponding 'deep' ChIP-seq analysis was done for H3K4me (Newman J.J. and Young, R. A. Cold Spring Harb. Symp. Quant. Biol. 2011. 75: 227-235), a histone modification considered to mark enhancers (Heintzman, et al., Nat. Genet. 2007. 39: 311-318). Analysis was also done for H3K27ac, a modification considered to mark potentially active enhancers (Creyghton, M. P. et al., Proc. Natl. Acad. Sci. USA. 2010. 107: 21931-6). Analysis of these two markers was used to identify 7,797 potential estrogen-responsive enhancers.

Example 8

GRO-Seq Analysis of Genome-Wide Transcription Units Regulated by ERα

The transcriptional consequences of a one hour $E_2$ treatment at 100 nM, compared to the vehicle, was determined by GRO-Seq (Core, L. J. et al., Science. 2008. 322: 1845-8) to provide a genome-wide catalogue of transcription units regulated by ERα.

GRO-sequencing of nascent RNAQ was achieved using MCF-7 cells hormone-stripped for 3 days and treated or not with 100 nM Estradiol ($E_2$) for 1 hr to induce estrogen signaling. The cells were then washed three times with cold PBS buffer and then swelled in swelling buffer (10 mM Tris-HCl, pH 7.5, 2 mM $MgCl_2$, 3 mM $CaCl_2$) for 5 min on ice, and harvested. Cells were re-suspended and lysed in lysis buffer (swelling buffer with 0.5% IGEPAL and 10% glycerol). Nuclei were washed once with 10 mM lysis buffer and re-suspended in 100 µL freezing buffer (50 mM Tris-HCl, pH 8.3, 40% glycerol, 5 mM $MgCl_2$, 0.1 mM EDTA). For the run-on assay, resuspended nuclei were mixed with an equal volume of reaction buffer (10 mM Tris-HCl, pH 8.0, 5 mM $MgCl_2$, 1 mM DTT, 300 mM KCl, 20 units SUPERase-In™, 1% sarkosyl, 500 µM ATP, GTP, Br-UTP, 2 µM CTP), and incubated for 5 min at 30° C. The nuclear run-on RNA (NRO-RNA) was then extracted with TRIzol LS reagent (Invitrogen), following the manufacturer's instructions. NRO-RNA was then subjected to base hydrolysis on ice for 40 min, followed by treatment with DNase I and Antarctic phosphatase. To purify the Br-UTP labeled RNA, the NRO-RNA was immunoprecipitated with anti-BrdU agarose beads (Santa Cruz Biotech) in binding buffer (0.5× SSPE, 1 mM EDTA, 0.05% Tween-20) for 1 hour at 40° C. with rotation. To repair the end, the immunoprecipitated BrU-RNA was re-suspended in 50 µL reaction (45 µL DEPC water, 5.2 µL T4 PNK buffer, 1 µL SUPERase-In and 1 µL T4 PNK [NEB]) and incubated at 37° C. for 1 hr. The RNA was extracted and precipitated using acidic phenol-chloroform.

cDNA synthesis was performed, as described previously (Tsai, M. C. et al., Science. 2010. 329: 689-93), with some modifications. The RNA fragments were subjected to poly-A tailing reaction by poly-A polymerase (NEB) for 30 min at 37° C. Subsequently, reverse transcription was performed using oNTI223 primer, the sequence of which is presented in Table 18. Tailed RNA (8.0 µL) was subjected to reverse transcription using Superscript III (Invitrogen). The cDNA products were separated on a 10% polyacrylamide TBE-urea gel. The extended first-strand product (100-500 bp) was excised and recovered by gel extraction. The first-strand cDNA was then circularized by CircLigase™ (Epicentre) and re-linearized by Ape1 (NEB). Re-linearized single strand cDNA (sscDNA) was separated in a 10% polyacrylamide TBE gel and the product of needed size was excised (~120-320 bp) for gel extraction. Finally, sscDNA template was amplified by PCR using the Phusion High-Fidelity enzyme (NEB), according to the manufacturer's instructions. The oligonucleotide primers oNTI200 and oNTI201 were used to generate DNA for deep sequencing (Table 18). ';' indicated an abasic dSpacer furan; 'N' indicates degenerate nucleotides.

TABLE 18

Oligos used in the Gro-Seq protocol

| Name | Sequence 5' to 3' | SEQ ID NO |
|---|---|---|
| oNTI223 | GATCGTCGGACTGTAGAACTCT; CAAGCAGAAGACGGCATACGATT TTTTTTTTTTTTTTTTTTN | 7 |
| oNTI200 | CAAGCAGAAGACGGCATA | 8 |
| oNTI201 | AATGATACGGCGACCACCGACAG GTTCAGAGTTCTACAGTCCGACG | 9 |
| Illumina small RNA-seq | CGACAGGTTCAGAGTTCTACAGT CCGACGATC | 10 |

Transcript identification and assignment to genomic regions, including annotated genes was accomplished using HOMER. GRO-Seq read densities were analyzed in a similar manner to ChIP-Seq, except that in this case, all the GRO-Seq libraries corresponding to the same experiment were merged in order to maximize read density for transcript identification. Provided GRO-Seq generated strand-specific data, separate tracks were uploaded onto the UCSC genome browser, once tag-enriched sites were identified using a sliding window of 250 bp. The portion of GRO-Seq tags that mapped to repeat regions was excluded and instead, the read density for these regions was approximated with values from flanking regions to avoid having to end transcripts prematurely. Transcript initiation sites were identified as regions where the GRO-Seq read density increased three-fold relative to the preceding 1 kb region. Transcript termination sites were defined by either a reduction in reads below 10% of the start of the transcript or when another transcript's start site was identified on the same strand. Individual high-density peaks spanning a region less than 250 bp were considered as artifacts, and thus removed from the analysis. Transcripts were defined as putative eRNAs if their TSS was located distal to RefSeq TSS (≥3 kb) and were associated with ERα and H3K4me1 regions. To identify differentially regulated transcripts, strand-specific read counts from each GRO-Seq experiment were determined for each transcript using HOMER. EdgeR (www.bioconductor.org/) was then used to calculate differential genomic and non-genic expression (≥1.5-fold, ≤0.01 false discovery rate).

The sequencing resulted in the finding of 1,033 up-regulated genes that exhibited $E_2$/ERα-binding in one or in multiple adjacent enhancers, while only 112 of these ERα up-regulated coding genes exhibited ERα binding to their promoters, consistent with initial suggestions (Jin, V. X. et al., Nucleic Acids Res. 2004. 32: 6627-35; Carroll, J. S. et al., Nat. Genet. 2006. 38: 1289-97; Kwon, Y. S. et al., Proc. Natl. Acad. Sci. USA 2007. 104: 4852-7; Lin, C. Y. et al., PLoS Genet. 2007. 3: e87; Welboren, W. J. et al., EMBO J. 2009. 28: 1418-28) that ERα occupancy on enhancers is likely to be the key strategy underlying estrogen-induced gene expression.

The $E_2$-regulated enhancers generally displayed a basal expression of bidirectional eRNAs and those in proximity to up-regulated coding genes displayed a characteristic bidirectional activation of eRNAs, exemplified by the FOXC1 locus, in general agreement with recent findings (Hah, N. et al., Cell. 2011. 145: 622-34). In contrast to the more 1:1 enhancer:promoter ratio for AR-regulated genes (Prasanth, K. V. and Spector, D. L. Genes Dev. 2007. 21: 11-42), there was often more than one ERα-bound enhancer adjacent to up-regulated coding genes. This raised the possibility that for many estrogen-regulated coding genes, more than one enhancer might be involved in up-regulation events and might even cross-regulate. The eRNA transcripts varied in apparent length but were generally ~1.5 kb, although ~10% exhibited an apparent predominance of unidirectional eRNA transcripts. Analysis of the GRO-Seq data confirmed the overall up-regulation of eRNAs in response to ligand, generally with bidirectional transcription, robust at 1 h after $E_2$, and subsequently diminishing, and being highly diminished by 24 hr. Overall, >83% of ERα-bound enhancers adjacent to up-regulated coding genes exhibited $E_2$-induced eRNA transcription by GRO-Seq. The median distance between enhancers exhibiting $E_2$-dependent up-regulation of their eRNAs and their closest up-regulated coding gene was ~52 kb, with most <215 kb from the coding gene cap site, compared with a median distance of >270 kb for enhancers exhibiting ligand-insensitive enhancer eRNAs with corresponding non-responsive coding genes. Examining the strength of ERα binding, based on normalized ChIP-seq data on these cohorts of enhancers with upregulation of the eRNAs, exhibited significantly stronger binding than on enhancers not exhibiting eRNA upregulation.

Based on these GRO-seq data analyses, ten robustly up-regulated transcription units were selected for further experimentation, each associated with enhancers exhibiting clearly increased eRNAs-CA12, FOXC1, GREB1, P2RY2, SMAD7, PGR, SIAH2, NRIP1, TFF1 and KCNK5. For these transcription units, there was a ~2-5-fold increase in coding gene expression, with a corresponding ~2.5-5-fold increase in eRNA expression on associated enhancers, assessed 1 hr following addition of $E_2$ to MCF-7 cell cultures.

Example 9

Investigation of the Potential Role of Ligand-Induced eRNAs on Gene Activation Events Using Transcription Inhibition Assays To investigate the potential roles, if any, of ligand-induced eRNAs on gene activation events, two different technologies were employed to down-regulate eRNAs: siRNAs and locked nucleic acid antisense oligonucleotides (LNAs).

Specific siRNAs directed at several regions of each transcript were used to assess possible effects on gene expression (Table 19). Similarly, LNAs were utilized by placing the LNA-modified bases at key positions to ensure target specificity as well as stability of the oligonucleotides (Table 20). The LNAs were designed for this purpose with complete phosphorothioate backbones to trigger RNAse H cleavage of the targeted sequences (Vester, B. et al., Bioorg. Med. Chem. Lett. 2008. 18: 2296-300) (Table 20). In both cases, the siRNAs or LNAs were designed based on the location of the eRNA CAP sites ~200 bp 5' of ERα binding sites, determined using the modified GRO-seq protocol described above. For both LNAs and siRNAs, scrambled sequences were used as controls. For all transcription units examined, experiments were performed with two different LNAs or siRNAs, with similar knock-down efficacy, to exclude any off-target effects.

TABLE 19 siRNA sequences

| Name (Sense) | Sequence (Sense) 5' to 3' | SEQ ID NO: | Name (Antisense) | Sequence (Sense) 5' to 3' | SEQ ID NO: | Over-hangs |
|---|---|---|---|---|---|---|
| TFF1e_1 | CAGAGUCAGAGAGUCAGAGAGAU | 11 | TFF1e_1 | AUCUCUCUCUGACUCUCUGACUCUG | 12 | None |
| TFF1e_2 | GAGUUUGGACCUGUGACCUUCCUAA | 13 | TFF1e_2 | UUAGGAAGGUCACAGGUCCAAACUC | 14 | None |
| TFF1e_3 | AAUCUCCUGGGAGGAUGAAGCUGUU | 15 | TFF1e_3 | AACAGCUUCAUCCUCCCAGGAGAUU | 16 | None |
| GREB1e1_1 | ACCACUGUUUCUGACUGCUUUCUCA | 17 | GREB1e1_1 | UGAGAAAGCAGUCAGAAACAGUGGU | 18 | None |
| GREB1e1_2 | GGAUUGAGAGUGACCAGGCAUUUA | 19 | GREB1e1_2 | UAAAUGUCCUGGUCACUCUCAAUCC | 20 | None |
| GREB1e1_3 | CGCCCAGCCUAAUUGUAGUACUUUA | 21 | GREB1e1_3 | UAAAGUACUACAAUUAGGCUGGGCG | 22 | None |
| PGRe_1 | GCAAAUUCUUUCAUGACAA | 23 | PGRe_1 | UUGUCAUGAAAGAAUUUGC | 24 | UU |
| PGRe_2 | GCAAAGAUGGAUAGAGAUA | 25 | PGRe_2 | UAUCUCUAUCCAUCUUUGC | 26 | UU |
| SIAH2e1_1 | GCACAUACCUCAUUAGAGA | 27 | SIAH2e1_1 | UCUCUAAUGAGGUAUGUGC | 28 | UU |
| SIAH2e2_2 | GGUAUUAAUAGCUCUGAAA | 29 | SIAH2e2_2 | UUUCAGAGCUAUUAAUACC | 30 | UU |
| NRIP1e1_1 | GGGAGAGGGUCUACAAUUA | 31 | NRIP1e1_1 | UAAUUGUCGACCCUCUCCC | 32 | UU |
| NRIP1e3_2 | GGCCAGAUCUCCUGUGAUA | 33 | NRIP1e3_2 | UAUCACAGGAGAUCUGGCC | 34 | UU |
| FOXC1e_1 | GCUCCAUUCUGCUGCUCAA | 35 | FOXC1e_1 | UUGAGCAGCAGAAUGGAGC | 36 | UU |
| FOXC1e_2 | CUAACGUGACAGUGACAUA | 37 | FOXC1e_2 | UAUGUCACUGUCACGUUAG | 38 | UU |
| P2RY2e_1 | GCAAAAGGUAGGAGGGUUU | 39 | P2RY2e_1 | AAACCCUCCUACCUUUUGC | 40 | UU |
| P2RY2e_2 | GGAGAUGAAUUGAUAGAGA | 41 | P2RY2e_2 | UCUCUAUCAAUUCAUCUCC | 42 | UU |
| CA12e_1 | CAGAAGAGCUAUUUGGUAU | 43 | CA12e_1 | AUACCAAAUAGCUCUUCUG | 44 | UU |
| CA12e_2 | GAGUGGACUUCACAAGAAA | 45 | CA12e_2 | UUUCUUGUGAAGUCCACUC | 46 | UU |
| SMAD7e1_1 | AGAGAAGAAUGAAGGUGAA | 47 | SMAD7e1_1 | UUCACCUUCAUUCUUCUCU | 48 | UU |
| SMAD7e2_2 | CCACAGGUGAGCAGAAAUU | 49 | SMAD7e2_2 | AAUUUCUGCUCACCUGUGG | 50 | UU |
| SMAD7e3_3 | CCUAAUUCCCAGAAGCAGA | 51 | SMAD7e3_3 | UCUGCUUCUGGGAAUUAGG | 52 | UU |
| KCNK5e1_1 | CGAAAUGGCCUAAAGAUGA | 53 | KCNK5e1_1 | UCAUCUUUAGGCCAUUUCG | 54 | UU |
| KCNK5e2_2 | ACACAAAGGUGGAAGGAAA | 55 | KCNK5e2_2 | UUUCCUUCCACCUUUGUGU | 56 | UU |
| KCNK5e3_3 | GGAAGAACCUGCAGAGAUG | 57 | KCNK5e3_3 | CAUCUCUGCAGGUUCUUCC | 58 | UU |

TABLE 20

LNA sequences

| LNA name | Sequence | SEQ ID NO: |
|---|---|---|
| LNA_Ctrl | CACGTCTATACACCAC | 59 |
| TFF1E_1 | GAATTAACGCCTGAGG | 60 |
| TFF1E_2 | GAACTGACAAAGGTGG | 61 |
| TFF1E_3 | ATCTCCCCACTCAAGG | 62 |
| TFF1E_4 | CATTTTTCTGCTGACC | 63 |
| CA12E_1 | ACAAGACAGAGGCAGA | 64 |
| CA12E_2 | TCAGTTGGAGGACAGT | 65 |
| FOXC1E_1 | GAAGGAGCAGGTGAAA | 66 |
| FOXC1E_2 | GGTATTTCCGCTTCAC | 67 |
| NRIP1E3_1 | AGGATACCAGGACACA | 68 |
| NRIP1E3_2 | TGATAAAGCAGGGTC | 69 |

Twenty four hours after cell seeding, MCF-7 cells were hormone-stripped for one day, followed by siRNA transfection (40 nM) using LipofectAMINE2000®. Cells were washed twice with PBS and maintained in hormone-deprived phenol-free supplemented stripped media for 2 days, and then treated with EtOH or E2 for 1 hr. LNA transfections (40 nM) were performed 2 days after starvation in stripped media and the LNA treatment lasted 6 or 24 hrs, after which cells were treated as described above.

For RT-QPCR, RNA was isolated using TRIzol reagent (Invitrogen), and total RNA was reverse-transcribed using SuperScript® III Reverse Transcriptase (Invitrogen), as per the manufacturer's instructions. Quantitative PCRs were performed in MX3000P (Stratagene), using Q-PCR master mix (Agilent Inc.). For normalization, ΔCt values were calculated using the formula: ΔCt=(Ct Target−Ct input) where input corresponds to the level of ACTB transcript. Fold differences in normalized gene expression were calculated by dividing the level of expression of the treated sample with the untreated sample or between siRNA/LNA and Control siRNA/control-LNA transfected cells. A list of primers used for Q-PCR is provided in Tables 21 and 22. 'F' and 'R' indicate the forward and reverse primers, respectively.

TABLE 21

List of primers used to measure eRNA

| Name | Sequence 5' to 3' | SEQ ID NO: |
|---|---|---|
| TFF1e_F | TCAGTTCCCAGCATTCTCATC | 70 |
| TFF1e_R | TTGAGCCTTGGAGACAGAAAG | 71 |
| GREB1e1_F | TCCAAAGCATCCCATTCCTG | 72 |
| GREB1e1_R | TGAGCAAAACAAGACAAACCG | 73 |
| PGRe_F | TTATGTTGCTCTTGATAGACTCCC | 74 |
| PGRe_R | GCTAGGTGCTGTCTGAGATTC | 75 |
| SIAH2e1_F | TTCAAGCAAAGATTATAGCCATGTG | 76 |
| SIAH2e1_R | ATCCAGTGCAGAGTAACATCAG | 77 |
| SIAH2e2_F | AGATGCCTCTGCATACTGGTT | 78 |
| SIAH2e2_R | CAGACCATATTGGGCCACAG | 79 |
| NRIP1e1_F | CCACAGCAGAAAACCACTGA | 80 |
| NRIP1e1_R | TTCCCTCTGCACTGACTCCT | 81 |
| NRIP1e3_F | CGTCTTTTCCCACTGACACA | 82 |
| NRIP1e3_R | CCCCTCCCCAGAAGAAAATA | 83 |
| FOXC1e_F | CTGAGGAACACAAGACTAGCC | 84 |
| FOXC1e_R | ACTGGACTCATTTTGGGACATC | 85 |
| P2RY2e_F | ATTGTGCATGGCTCTTACCC | 86 |
| P2RY2e_R | CTTGGTGCATGTGAGCTTGT | 87 |
| P2RY2e_F | AGCTTCTGGTTCCAAGGTCA | 88 |
| P2RY2e_R | CATGTGCTGTTGTTGCTGTG | 89 |
| CA12e_F | TGAAAGGGAAGACGCAGATG | 90 |
| CA12e_R | TTGTATCCTTTGACTGGGCAG | 91 |
| SMAD7e1_F | AAAGAAGGCAGGGGAACAAT | 92 |
| SMAD7e1_R | CACTTGGGCAATCCAGAAAT | 93 |
| SMAD7e2_F | TCACCTGTGGAAAGAGACAAC | 94 |
| SMAD7e2_R | AGAACCTTTTGCTCCCTAGTG | 95 |
| SMAD7e3_F | TTAAACGAGCCTGGAGTTGG | 96 |
| SMAD7e3_R | AAATTCCTCAGAGCCCAGTG | 97 |
| KCNK5e1_F | GGCTCAGAGAGGCCAAAA | 98 |
| KCNK5e1_R | TGGACCCTATCATCTCCTTTAACT | 99 |
| KCNK5e2_F | GGAAAGGAATTGCTGGATCA | 100 |
| KCNK5e2_S_R | GTGCAACCACTTGGGAAACT | 101 |
| KCNK5e3_S_F | CAGAGATGAGGAAAGGTTTGC | 102 |
| KCNK5e3_S_R | ATCTGCTTCACGGTCTCATG | 103 |

TABLE 22

List of primers used to measure mRNA

| Name | Sequence 5' to 3' | SEQ ID NO: |
|---|---|---|
| FOXC1_F | AGTAGCTGTCAAATGGCCTTC | 104 |
| FOXC1_R | TTAGTTCGGCTTTGAGGGTG | 105 |
| P2RY2_F | GGGGACCTGTTTTTCCTGTT | 106 |
| P2RY2_R | GACTTGGATCTGGACCTGGA | 107 |
| CA12_F | TCTGTCTGCCAACAAGCAGT | 108 |
| CA12_R | GCACTGTAGCGAGACTGGAG | 109 |
| SMAD7_F | TCCTGCTGTGCAAAGTGTTC | 110 |
| SMAD7_R | AAATCCATCGGGTATCTGGA | 111 |
| KCNK5_F | TGCCAAGAGACTAGGGCAGT | 112 |
| KCNK5_R | GAATACGAAGGGTGGGATCA | 113 |
| PGR_F | CATCACAGGGAACCAGACCT | 114 |
| PGR_R | CACCCCGAAGAGACCATAGA | 115 |
| SIAH2_F | TCAGGAACCTGGCTATGGAG | 116 |
| SIAH2_R | GGCAGGAGTAGGGACGGTAT | 117 |
| NRIP1_F | GCCAGAAGATGCACACTTGA | 118 |
| NRIP1_R | CAAGCTCTGAGCCTCTGCTT | 119 |
| TFF1_F | CACCATGGAGAACAAGGTGA | 120 |
| TFF1_R | TGACACCAGGAAAACCACAA | 121 |
| GREB1_F | GGCAGGACCAGCTTCTGA | 122 |
| GREB1_R | CTGTTCCCACCACCTTGG | 123 |

Both siRNA knockdown and LNA treatment of the TFF1, FOXC1, CA12 and NRIP1 enhancers revealed that, for each transcription unit, the induction of both the eRNA and of the adjacent coding gene transcript, as assessed by Q-PCR and GRO-seq, respectively, was significantly inhibited or fully abolished. In contrast, these LNAs or siRNAs caused no inhibitory effects on housekeeping genes tested or on $E_2$-regulated or non-E2-regulated adjacent transcription units located distal to the regulated coding genes, as exemplified by measuring levels of RSPH1 (TFF1e), APH1b (CA12e), and USP25 (NRIP1e). Ligand-induced increase of ERα binding occurred even after eRNA knockdown. Similar eRNA requirements for coding genes were observed based on knockdown of the eRNAs for PGR, SIAH2, KCNK5, P2RY2 and SMAD7, using either of two LNAs or siRNAs designed for each targeted enhancer. GRO-Seq analysis of effects of siRNAs or LNAs on $E_2$-regulated coding transcription units gave similar results as those quantitated by QPCR.

Example 10

Investigation of the Potential Role eRNA in Enhancer: Promoter Looping Events

To investigate whether eRNAs might be required for enhancer: promoter looping events, generally considered to be part of the $E_2$-activation process, an open-ended (3D-DSL) approach was employed for studying the spatial organization of genomes (Harismendy, O. et al., Nature. 2011. 470: 264-8), conceptually analogous to 5C methodology (Fullwood, M. J. et al., Nature. 2009. 462: 58-64).

In the 3D-DSL method, oligonucleotides corresponding to genomic sites that are to be analyzed for participation in a network contain a 5'-phosphate (referred to as acceptors), while oligonucleotides corresponding to genomic sites of potential interaction have a 5'-OH (referred to as donors). This method permits interrogation of both short (<10 kb), as well as long-distance, genomic interactions with specific genomic regions including promoters and enhancers. Therefore, "donor" pools of oligonucleotides spanning ~200 kb flanking the promoter of four up-regulated ERα target genes were designed based on the HindIII restriction site. The "acceptor" pool constituted all ERα binding sites and promoters in the interval. The housekeeping gene GAPDH was used as a control (data not shown).

3D-DSL was performed as described previously (Fullwood, M. J. et al., Nature 2009. 462: 58-64). Briefly, equal amount of 3C chromatin was biotinylated using the Photoprobe Kit (Vector Lab). Donor and acceptor probe pools (2.5 fmol per probe) were annealed to the biotinylated 3C samples at 45° C. for 2 hrs, followed by 10 min at 95° C. The biotinylated DNA was immunoprecipitated with magnetic beads conjugated to streptavidin. During this process, unbound oligonucleotides were removed by stringent washes. The 5'-phosphate of acceptor probes and 3'-OH of donor probes were ligated using Taq DNA ligase at 45° C. for 1 hr. These ligated products were washed and eluted from beads and then amplified by PCR using primers A and B-AD (or Primer B-BC1 and -BC2 if bar coding was used) for deep sequencing on the Illumina HiSeq 2000, using Primer A as sequencing primer.

For data analysis, a virtual library was first built of all possible donor-acceptor sequences by in silico concatenating all acceptor sequences with all donor sequences. These reads were then aligned to the virtual library of DSL donors-acceptors sequences, using NOVOALIGN (-t 248 -r None), and the number of reads that are mapped to every interaction with no mismatches were counted, by using custom Perl scripts. Next, from each sample the counts given by the ligations of donors to acceptors on the identical restriction sites (the "spot" ligations) was subtracted, and the counts of the interactions were normalized to the remaining number of total reads, after subtraction. Finally, from each interaction, the counts that are present in unligated controls were subtracted, after normalization.

3D-DSL plots were generated using Matlabs where a 10 kb window was set to bundle the interaction intensities, except for a 20 kb window for NRIP1. The interactions were plotted using a Bezier curve between the two positions with the third point in the middle of the positions with the y-axis corresponding to the log 10 intensity. The peak locations were then added on the bottom of the plot.

Two $E_2$-regulated transcription units, P2RY2 and KCNK5, were first examined. In the case of the P2RY2 transcription unit, $E_2$ caused an increase in the specific promoter: enhancer interaction approximately 1,000-fold compared to that observed in the control cultures. In addition to promoter: enhancer loops, a new interaction between enhancer and gene terminator was also observed, as compared to the -$E_2$ condition. The P2RY2 promoter locus exhibited three additional loops, one of which did not change upon $E_2$ treatment, but two other low intensity loops disappeared upon gene activation, consistent with the dynamic nature of gene topology. Based on results of ERα knock-down, it was noted that even after 3 days in stripped-serum medium, MCF-7 cells still exhibited some ERα-dependent basal activation of a significant cohort of coding gene targets, and hence both siRNAs and LNAs against enhancer eRNAs caused a decrease in basal transcription for some $E_2$-regulated genes, in addition to their more robust effects on $E_2$-stimulated gene expression. Similarly, for the KCNK5 gene locus, $E_2$ treatment caused a >300-fold increase in promoter: enhancer interactions. Two more loops arising from enhancer in response to $E_2$ were detected, one of them around the terminator region of gene and the other around that might represent enhancer-specific loops. These observations indicate that a major effect of the ligand was to enhance specific promoter: enhancer interactions and, in some cases, enhancer: gene terminator interactions, in parallel to induction of eRNA. For some loci, new enhancer: promoter interactions were actually established and additional interactions were also observed. This raised the question whether the induced eRNAs exert any roles in the dynamic regulation of short-range and long-range induced interactions.

Example 11

Investigation of the Regulation of $E_2$-Induced Enhancer: Promoter Interactions by Specific eRNAs The effect of loss of specific eRNAs on E2-induced enhancer: promoter interactions was investigated.

LNAs that were highly effective against two estrogen-regulated enhancers, NRIP1 and GREB1, were characterized. Chromatin conformation capture (3C) was performed. Briefly, $25 \times 10^6$ MCF-7 cells were fixed by adding 1% formaldehyde at room temperature for 10 min, and the reaction stopped by adding glycine. Lysis buffer (500 μl 10 mM Tris-HCl pH 8.0, 10 mM NaCl, 0.2% IGEPAL CA-630, protease inhibitors [Sigma]) was added and cells were incubated on ice. Next, cells were lysed with a Dounce homogenizer, and the suspension spun down at 5,000 rpm at 4° C. The supernatant was discarded and the pellet was washed twice with 500 μl ice-cold 1× NEBuffer 2 (NEB, Ipswich, Mass.). The pellet was then resuspended in 1× NEBuffer 2 and split into five separate 50 μl aliquots. The extracted chromatin was then digested overnight by adding 400 units HindIII (NEB). Each digested chromatin mixture was ligated by adding T4 DNA Ligase (800 units) in 20 times of initial volume for 4 hrs at 16° C. The ligase step was omitted in one chromatin aliquot from the five mentioned above to use the sample as the unligated control. After incubation at 16° C., the chromatin was de-cross-linked overnight at 65° C. and purified twice with phenol and then with phenol: chloroform:IAA (25:24:1). DNA was precipitated and pellets were air-dried before re-suspending in 250

µl 1×TE buffer. To degrade any carryover RNA, 1 µl RNAse A (1 mg/ml) was added to each tube and incubated at 37° C. for 15 min. DNA was further purified using Phenol: Chloroform: IAA and precipitated. This enriched fraction was used for the DSL part of the protocol or subjected to PCR using unique primers, and was electrophoresed on Agarose gel.

In the case of the NRIP1 locus, which was shown to exhibit a ligand-induced enhancer: promoter loop by conventional 3C assay, treatment with LNA against eRNA caused a ~200-fold inhibition of the coding gene expression and also inhibited both enhancer: promoter and enhancer: terminator interactions in $E_2$-treated MCF-7 cells, assessed using conventional 3C assays and 3D-DSL. An interaction between a different upstream ERα-binding site and the promoter was not affected. In the case of the GREB1 locus, siRNA-mediated eRNA knockdown inhibited GREB1 coding gene induction and also inhibited the specific enhancer: promoter interaction induced by $E_2$. The enhancer: terminator loop was also reduced upon siRNA-mediated knockdown of eRNA, suggesting that eRNAs are required for interactions between enhancer and adjacent regulatory elements. Additional interactions of the GREB1 promoter with a non-enhancer region were also diminished by eRNA knockdown, indicating that these loops were altered by interruption of enhancer: promoter interaction, licensing other interactions.

Together these experiments indicate that estrogen causes quantitative, as well as some qualitative, alterations in the interactions between enhancers and coding gene promoters and even between enhancers, terminators and other ERα-bound regions, which are highly diminished or abolished with downregulation of the targeted eRNAs. For these gene targets, the eRNA was, therefore, of functional importance for robust enhancer: promoter interactions, with knockdown by either siRNA or LNA treatment invariantly diminishing, or even abolishing, these putatively activating enhancer: promoter interactions, consistent with eRNA function, even under unstimulated conditions.

Example 12

Investigation of Enhancer and Promoter Interactions

The interaction between an enhancer and promoter that spans a distance of >250 kb permitting FISH analysis, was investigated.

Cells were processed for DNA ImmunoFISH. BAC probes were commercially obtained from Empire Genomics and are listed in Table 23.

TABLE 23

BAS probes

| Gene | Coordinates (including eRNA/s) | FISH BAC |
| --- | --- | --- |
| FOXC1 | chr6: 1,548,833-1,590,281 | RP11-13F18 |
| P2RY2 | chr11: 72,568,712-72,653,158 | RP11-352115 |
| STARD10 | chr11: 71,986,844-72,178,371 | RP11-610C10 |
| NRIP1 | chr21: 15,228,005-15,513,603 | RP11-22D1 |
| GREB1 | chr2: 11,530,334-11,710,942 | RP11-50E1 |

MCF-7 cells were grown onto acid-washed polylysine-coated coverslips. Cells were treated with vehicle (EtOH) or E2 for 1 hour, washed with PBS and immediately fixed with freshly made 4% paraformaldehyde/PBS for 10 min. Permeabilization was achieved by incubating in ice-cold cytoskeletal buffer (10 mM PIPES, pH 6.8; 300 mM sucrose; 100 mM NaCl; 3 mM $MgCl_2$; 1 mM EGTA; 20 mM vanadyl ribonucleoside complex and 1 mM 4-(2-aminoethyl) benzenesulfonyl fluoride) containing 0.5% Triton X-100 for 10 min. FISH pre-hybridization treatments included incubating the coverslips in 0.1N HCl for 5 min at room temperature, followed by digestion with 0.01N HO/0.002% pepsin for 5 min at 37° C., stopped by 50 mM $MgCl_2$/PBS and equilibrated in 50% formamide/2×SSC 2 hrs prior to hybridization. Five microliters of probe/hybridization buffer mix (Empire Genomics) was used per coverslip, with a hybridization program of 76° C. for 3 min followed by overnight hybridization at 37° C. in a humidified dark chamber. The coverslips were then washed with pre-warmed WS1 (0.4× SSC/0.3% NP-40) buffer to 72° C. for 2 min, and then transferred to WS2 (2×SSC/0.1% NP-40) buffer at room temperature for 1 min. A final wash with 1×PBS was performed, excess liquid was aspirated and the coverslips were then mounted with prolong gold-DAPI antifade mounting reagent (Invitrogen).

One known interaction suitable for study was chosen: the interaction between two $E_2$-regulated P2RY2 and STARD10-transcription units at a distance of ~428 kb (Fullwood, M. J. et al., Nature. 2009. 462: 58-64). Knockdown of the P2RY2 enhancer by specific siRNAs caused downregulation of the two $E_2$-regulated target-coding genes, P2RY2 and STAR10, both of which are upregulated following $E_2$ treatment. These two genomic loci exhibited $E_2$-dependent enhanced colocalization when treated with $E_2$, for 1 hr prior to fixation and examination using FISH. When cells were transfected with siRNAs against P2RY2e, the P2RY2e knockdown blocked the previously observed P2RY2: STARD10 co-localization. Therefore, together, these data suggest that ligand-dependent induction of eRNAs initiates processes, including enhancer: promoter looping, in concert with the requirement for the resultant coding gene activation observed after hormone treatment.

Additional data supporting the suggestion that eRNAs are required for tight control of ERα-regulated genes was provided by evidence of its role in the "switch" from association with corepressors to coactivators. The methylation status of Pc2 present on growth control gene regulatory regions regulates its association with two abundant ncRNAs, TUG1 and NEAT2, located primarily with markers of distinct subnuclear individual structures-polycomb bodies (PcGs) and interchromatin granules (ICGs), respectively (Yang, L. et al., Cell. 2011. 147: 773-88). Studies were conducted to test if similar interactions might be regulated by eRNAs induced by liganded ERα ImmunoFISH was performed using antibodies against RING1a (H-110, Santa Cruz Biotechnology), and the interchromatin granule marker, SC35 (ab88720, Abcam), and with specific BAC probes for three genomic loci interrogated (NRIP1, FOXC1, and SIAH2). This revealed that there was a reproducible $E_2$-dependent switch in the predominant colocalization of each transcription unit from RING1a- to SC35-stained structures. When LNA transfections were used to deplete eRNA transcripts for two genes, FOXC1 and NRIP1, immunoFISH data from each locus showed a clear inhibition of their ligand-dependent-enhanced association with SC35, directly implicating the eRNA transcripts in these altered target gene co-localization events. Similar effects were observed for siRNA-mediated knock-down of the GREB-1 eRNA.

While it is quite likely that a series of complexes combinatorially contribute to these interactions, several studies have established a role for Cohesin in enhancer: promoter looping events (Hadjur, S. et al., Nature. 2009. 460: 410-3; Mishiro, T. et al., EMBO J. 2009. 28: 1234-45; Nativio, R. et al., PLoS Genet. 2009. 5: e1000739; Hou, C. et al., Proc. Natl. Acad. Sci. USA 2010. 107: 3651-6), and protein: protein interactions between Cohesin and the mediator complex protein, Med12, have been reported (Kagey, M. H. et al., Nature. 2010. 467: 430-5). Therefore, the levels of Cohesin recruitment to regulated ERα-regulated enhancers were assessed after ligand addition. An increased occupancy was observed of the Cohesin subunit Rad21 on ERα target genes enhancers adjacent to up-regulated coding genes after $E_2$ treatment, as studied by conventional ChIP and meta-analysis of ChIP-seq data. Based on fractionation studies, Rad21 association with chromatin was diminished following RNaseA treatment. Depletion of specific NRIP1 e eRNA by siRNA or LNA or FOXC1e eRNA by LNA, resulted in a decrease of Cohesin recruitment to enhancers in response to $E_2$, with essentially no significant alteration of the H3K4me enhancer mark, or in ligand-dependent increase of ERα recruitment. Therefore, eRNAs may help to stabilize the ERα-dependent recruitment of Cohesin to the regulatory enhancers, perhaps by recruiting some common or related complexes that contribute to this event.

Possible interactions between the Cohesin complex and regulated eRNAs were explored using RNA immunoprecipitation (RIP) with an anti-Rad21-specific antibody (ab922, Abcam). RNA immunoprecipitations were performed as described previously (Chen, J. et al., Mol. Endocrinol. 2006. 20: 1-13). Briefly, cells were washed in PBS, cross-linked by 1% paraformaldehyde for 10 min at room temperature, and 125 mM glycine was added to quench the cross-linking. The cell pellet was then lysed in Buffer A and then Buffer B. IP was performed overnight using 1-5 mg antibody. Thirty microliters of Dynabeads were used per IP or in a beads-alone reaction. IP complexes were washed and de-cross-linked at 65° C. DNase I treatment was given to get rid of genomic DNA. RNA was isolated and cDNA synthesis was performed.

This assay revealed that the eRNAs of FOXC1, PGR and TFF1, while highly divergent in primary sequence, exhibited interactions with Rad21 that were further enhanced after ligand treatment. siRNA-mediated depletion of Rad21 caused loss of enhancer: promoter interactions, both basal and $E_2$-induced, when assessed by 3C assay for the NRIP1 and GREB1 gene loci. In addition, these data suggest that eRNAs might be required for effective additional recruitment of the Cohesin complex to the enhancer in response to $E_2$, and their subsequent role in stabilizing enhancer: promoter interactions. This implies that the specific eRNA sequences participate in coding gene activation events.

The effects of $E_2$-dependent coding gene stimulation in MCF-7 cells treated with SMC3 (Cohesin subunit) siRNA (chosen for its more effective knock-down compared to Rad21 siRNA) vs. control siRNA was also assessed. Inhibition of most of the $E_2$-induced coding gene transcriptional program, with loss of ~50% of coding gene activation program by $E_2$, was observed with significant inactivation for the remaining $E_2$-activated transcription units. Using SMC3-specific siRNAs, inhibition of ERα target genes was confirmed by Q-PCR. Indeed, analysis of GRO-Seq data and MA analyses further confirmed the broad inhibition of $E_2$-dependent activating transcriptional effects following SMC3 knockdown in MCF-7 cells.

Example 13

Design of Antisense Oligonucleotides Targeting Murine Mmp9 eRNA

Antisense oligonucleotides were designed targeting a Mmp9 eRNA. The newly designed oligonucleotides in Table 24 were designed as uniform deoxy oligonucleotides with phosphate backbones, or as oligonucleotides containing deoxy, MOE and (S)-cEt units and a phosphorothioate backbone. "Start site" indicates the 5'-most nucleoside to which the oligonucleotide is targeted in the murine eRNA sequence. "Stop site" indicates the 3'-most nucleoside to which the oligonucleotide is targeted murine eRNA sequence. Each gapmer listed in Table 24 is targeted to SEQ ID NO: 202 (GENBANK Accession number NT_039207.7 truncated from 105809967 to 105810417). The Chemistry column describes the chemistry of each oligonucleotide, where'd' indicates 2' deoxyribose; 'o' indicates phosphate ester; 'e' indicates 2'-O-methyoxyethyl ribose (MOE); 's' indicates thioate ester; 'm' indicates 5' methyl group; 'k' indicates (S)-cEt. The SEQ ID NO for each antisense oligonucleotide is associated with its sequence and is not intended to require the chemistry indicated in Table 24.

TABLE 24

Antisense oligonucleotides targeted targeted to SEQ ID NO: 202
(GENBANK Accession number NT_039207.7 truncated from 105809967 to 105810417).

| ISIS No | Start Site | Stop Site | Sequence | Chemistry Notation | SEQ ID NO |
|---------|------------|-----------|----------|--------------------|-----------|
| 566188 | 14 | 29 | TCCATTGCCACCCCA | Tes mCes mCks Ads Tds Tds Gds mCds mCds Ads mCds mCds mCds mCks mCks Ae | 124 |
| 566189 | 17 | 32 | TCCTCCATTGCCACCC | Tes mCes mCks Tds mCds mCds Ads Tds Tds Gds mCds mCds Ads mCks mCks mCe | 125 |
| 566190 | 20 | 35 | ACTTCCTCCATTGCCA | Aes mCes Tks Tds mCds mCds Tds mCds mCds Ads Tds Tds Gds mCks mCks Ae | 126 |
| 566191 | 23 | 38 | CCAACTTCCTCCATTG | mCes mCes Aks Ads mCds Tds Tds mCds mCds Tds mCds mCds Ads Tks Tks Ge | 127 |

TABLE 24-continued

Antisense oligonucleotides targeted targeted to SEQ ID NO: 202
(GENBANK Accession number NT_039207.7 truncated from 105809967 to 105810417).

| ISIS No | Start Site | Stop Site | Sequence | Chemistry Notation | SEQ ID NO |
|---|---|---|---|---|---|
| 566192 | 41 | 56 | ACACTTCTCTCCCTAC | Aes mCes Aks mCds Tds Tds mCds Tds mCds Tds mCds mCds mCds Tks Aks mCe | 128 |
| 566193 | 65 | 80 | GGCTTGGAATCCATCA | Ges Ges mCks Tds Tds Gds Gds Ads Ads Tds mCds mCds Ads Tks mCks Ae | 129 |
| 566194 | 91 | 106 | CAACTGCGGAGGGAGG | mCes Aes Aks mCds Tds Gds mCds Gds Gds Ads Gds Gds Gds Aks Gks Ge | 130 |
| 566195 | 94 | 109 | TACCAACTGCGGAGGG | Tes Aes mCks mCds Ads Ads mCds Tds Gds mCds Gds Gds Ads Gks Gks Ge | 131 |
| 566196 | 97 | 112 | TCTTACCAACTGCGGA | Tes mCes Tks Tds Ads mCds mCds Ads Ads mCds Tds Gds mCds Gks Gks Ae | 132 |
| 566197 | 100 | 115 | CTTTCTTACCAACTGC | mCes Tes Tks Tds mCds Tds Tds Ads mCds mCds Ads Ads mCds Tks Gks mCe | 133 |
| 566198 | 103 | 118 | GTTCTTTCTTACCAAC | Ges Tes Tks mCds Tds Tds Tds mCds Tds Tds Ads mCds mCds Aks Aks mCe | 134 |
| 566199 | 114 | 129 | GATTGCTGCTGGTTCT | Ges Aes Tks Tds Gds mCds Tds Gds mCds Tds Gds Gds Tds Tks mCks Te | 135 |
| 566200 | 117 | 132 | CAGGATTGCTGCTGGT | mCes Aes Gks Gds Ads Tds Tds Gds mCds Tds Gds mCds Tds Gks Gks Te | 136 |
| 566201 | 120 | 135 | CTTCAGGATTGCTGCT | mCes Tes Tks mCds Ads Gds Gds Ads Tds Tds Gds mCds Tds Gks mCks Te | 137 |
| 566202 | 123 | 138 | CGCCTTCAGGATTGCT | mCes Ges mCks mCds Tds Tds mCds Ads Gds Gds Ads Tds Tds Gks mCks Te | 138 |
| 562914 | 126 | 147 | CACTTCACTCGCCTTCAGGATT | Cdo Ado Cdo Tdo Tdo Cdo Ado Cdo Tdo Cdo Gdo Cdo Cdo Tdo Tdo Cdo Ado Gdo Gdo Ado Tdo Td | 139 |
| 566203 | 126 | 141 | ACTCGCCTTCAGGATT | Aes mCes Tks mCds Gds mCds mCds Tds Tds mCds Ads Gds Gds Aks Tks Te | 140 |
| 566204 | 129 | 144 | TTCACTCGCCTTCAGG | Tes Tes mCks Ads mCds Tds mCds Gds mCds mCds Tds Tds mCds Aks Gks Ge | 141 |
| 566205 | 132 | 147 | CACTTCACTCGCCTTC | mCes Aes mCks Tds Tds mCds Ads mCds Tds mCds Gds mCds mCds Tks Tks mCe | 142 |
| 566206 | 135 | 150 | TACCACTTCACTCGCC | Tes Aes mCks mCds Ads mCds Tds Tds mCds Ads mCds Tds mCds Gks mCks mCe | 143 |
| 566207 | 138 | 153 | GGGTACCACTTCACTC | Ges Ges Gks Tds Ads mCds mCds Ads mCds Tds Tds mCds Ads mCks Tks mCe | 144 |
| 566208 | 141 | 156 | AGTGGGTACCACTTCA | Aes Ges Tks Gds Gds Gds Tds Ads mCds mCds Ads mCds Tds Tks mCks Ae | 145 |
| 566209 | 144 | 159 | AGCAGTGGGTACCACT | Aes Ges mCks Ads Gds Tds Gds Gds Gds Tds Ads mCds mCds Aks mCks Te | 146 |
| 566210 | 147 | 162 | GTAAGCAGTGGGTACC | Ges Tes Aks Ads Gds mCds Ads Gds Tds Gds Gds Gds Tds Aks mCks mCe | 147 |
| 566211 | 152 | 167 | AGTGGGTAAGCAGTGG | Aes Ges Tks Gds Gds Gds Tds Ads Ads Gds mCds Ads Gds Tks Gks Ge | 148 |
| 566212 | 155 | 170 | AACAGTGGGTAAGCAG | Aes Aes mCks Ads Gds Tds Gds Gds Gds Tds Ads Ads Gds mCks Aks Ge | 149 |

TABLE 24-continued

Antisense oligonucleotides targeted targeted to SEQ ID NO: 202
(GENBANK Accession number NT_039207.7 truncated from 105809967 to 105810417).

| ISIS No | Start Site | Stop Site | Sequence | Chemistry Notation | SEQ ID NO |
|---|---|---|---|---|---|
| 566213 | 159 | 174 | CTGGAACAGTGGGTAA | mCes Tes Gks Gds Ads Ads mCds Ads Gds Tds Gds Gds Gds Tks Aks Ae | 150 |
| 566214 | 162 | 177 | TGCCTGGAACAGTGGG | Tes Ges mCks mCds Tds Gds Gds Ads Ads mCds Ads Gds Tds Gks Gks Ge | 151 |
| 566215 | 165 | 180 | AGGTGCCTGGAACAGT | Aes Ges Gks Tds Gds mCds mCds Tds Gds Gds Ads Ads mCds Aks Gks Te | 152 |
| 566216 | 171 | 186 | TTACAGAGGTGCCTGG | Tes Tes Aks mCds Ads Gds Ads Gds Gds Tds Gds mCds mCds Tks Gks Ge | 153 |
| 566217 | 174 | 189 | CTGTTACAGAGGTGCC | mCes Tes Gks Tds Tds Ads mCds Ads Gds Ads Gds Gds Tds Gks mCks mCe | 154 |
| 566218 | 177 | 192 | GGCCTGTTACAGAGGT | Ges Ges mCks mCds Tds Gds Tds Tds Ads mCds Ads Gds Ads Gks Gks Te | 155 |
| 566219 | 180 | 195 | GTGGGCCTGTTACAGA | Ges Tes Gks Gds Gds mCds mCds Tds Gds Tds Tds Ads mCds Aks Gks Ae | 156 |
| 566220 | 183 | 198 | CATGTGGGCCTGTTAC | mCes Aes Tks Gds Tds Gds Gds Gds mCds mCds Tds Gds Tds Tks Aks mCe | 157 |
| 566221 | 186 | 201 | TCCCATGTGGGCCTGT | Tes mCes mCks mCds Ads Tds Gds Tds Gds Gds Gds mCds mCds Tks Gks Te | 158 |
| 566222 | 189 | 204 | GTTTCCCATGTGGGCC | Ges Tes Tks Tds mCds mCds mCds Ads Tds Gds Tds Gds Gds Gks mCks mCe | 159 |
| 566223 | 192 | 207 | AGTGTTTCCCATGTGG | Aes Ges Tks Gds Tds Tds Tds mCds mCds mCds Ads Tds Gds Tks Gks Ge | 160 |
| 566224 | 201 | 216 | GCTAATAACAGTGTTT | Ges mCes Tks Ads Ads Tds Ads Ads mCds Ads Gds Tds Gds Tks Tks Te | 161 |
| 566225 | 204 | 219 | AGTGCTAATAACAGTG | Aes Ges Tks Gds mCds Tds Ads Ads Tds Ads Ads mCds Ads Gks Tks Ge | 162 |
| 566226 | 207 | 222 | ACAAGTGCTAATAACA | Aes mCes Aks Ads Gds Tds Gds mCds Tds Ads Ads Tds Ads Aks mCks Ae | 163 |
| 562911 | 218 | 241 | CATTTCCCCCATCTTAAAAACAG | Cdo Ado Tdo Tdo Tdo Cdo Cdo Cdo Cdo Cdo Ado Tdo Cdo Tdo Tdo Ado Ado Ado Ado Ado Cdo Ado Ado Gd | 164 |
| 566227 | 224 | 239 | TTTCCCCCATCTTAAA | Tes Tes Tks mCds mCds mCds mCds mCds Ads Tds mCds Tds Tds Aks Aks Ae | 165 |
| 566228 | 231 | 246 | CCTACCATTTCCCCCA | mCes mCes Tks Ads mCds mCds Ads Tds Tds Tds mCds mCds mCds mCks mCks Ae | 166 |
| 566229 | 234 | 249 | CAACCTACCATTTCCC | mCes Aes Aks mCds mCds Tds Ads mCds mCds Ads Tds Tds Tds mCks mCks mCe | 167 |
| 566230 | 237 | 252 | ACACAACCTACCATTT | Aes mCes Aks mCds Ads Ads mCds mCds Tds Ads mCds mCds Ads Tks Tks Te | 168 |
| 566231 | 240 | 255 | TCGACACAACCTACCA | Tes mCes Gks Ads mCds Ads mCds Ads Ads mCds mCds Tds Ads mCks mCks Ae | 169 |
| 566232 | 243 | 258 | CTATCGACACAACCTA | mCes Tes Aks Tds mCds Gds Ads mCds Ads mCds Ads Ads mCds mCks Tks Ae | 170 |
| 566233 | 246 | 261 | CAGCTATCGACACAAC | mCes Aes Gks mCds Tds Ads Tds mCds Gds Ads mCds Ads mCds Aks Aks mCe | 171 |

TABLE 24-continued

Antisense oligonucleotides targeted targeted to SEQ ID NO: 202
(GENBANK Accession number NT_039207.7 truncated from 105809967 to 105810417).

| ISIS No | Start Site | Stop Site | Sequence | Chemistry Notation | SEQ ID NO |
|---|---|---|---|---|---|
| 566234 | 249 | 264 | CCCCAGCTATCGACAC | mCes mCes mCks mCds Ads Gds mCds Tds Ads Tds mCds Gds Ads mCks Aks mCe | 172 |
| 566235 | 252 | 267 | TGACCCCAGCTATCGA | Tes Ges Aks mCds mCds mCds mCds Ads Gds mCds Tds Ads Tds mCks Gks Ae | 173 |
| 566236 | 255 | 270 | GTGTGACCCCAGCTAT | Ges Tes Gks Tds Gds Ads mCds mCds mCds mCds Ads Gds mCds Tks Aks Te | 174 |
| 566237 | 258 | 273 | ATTGTGTGACCCCAGC | Aes Tes Tks Gds Tds Gds Tds Gds Ads mCds mCds mCds mCds Aks Gks mCe | 2 |
| 566238 | 261 | 276 | CTCATTGTGTGACCCC | mCes Tes mCks Ads Tds Tds Gds Tds Gds Tds Gds Ads mCds mCks mCks mCe | 175 |
| 566239 | 264 | 279 | CAGCTCATTGTGTGAC | mCes Aes Gks mCds Tds mCds Ads Tds Tds Gds Tds Gds Tds Gks Aks mCe | 176 |
| 566240 | 268 | 283 | GCTTCAGCTCATTGTG | Ges mCes Tks Tds mCds Ads Gds mCds Tds mCds Ads Tds Tds Gks Tks Ge | 177 |
| 566241 | 271 | 286 | CAAGCTTCAGCTCATT | mCes Aes Aks Gds mCds Tds Tds mCds Ads Gds mCds Tds mCds Aks Tks Te | 3 |
| 566242 | 274 | 289 | ATCCAAGCTTCAGCTC | Aes Tes mCds mCds Ads Ads Gds mCds Tds Tds mCds Ads Gds mCks Tks mCe | 178 |
| 566243 | 280 | 295 | GCCGAAATCCAAGCTT | Ges mCes mCks Gds Ads Ads Ads Tds mCds mCds Ads Ads Gds mCks Tks Te | 179 |
| 566244 | 283 | 298 | ACTGCCGAAATCCAAG | Aes mCes Tks Gds mCds mCds Gds Ads Ads Ads Tds mCds mCds Aks Aks Ge | 180 |
| 566245 | 286 | 301 | TGGACTGCCGAAATCC | Tes Ges Gks Ads mCds Tds Gds mCds mCds Gds Ads Ads Ads Tks mCks mCe | 181 |
| 566246 | 289 | 304 | GATTGGACTGCCGAAA | Ges Aes Tks Tds Gds Gds Ads mCds Tds Gds mCds mCds Gds Aks Aks Ae | 182 |
| 566247 | 292 | 307 | TGGGATTGGACTGCCG | Tes Ges Gks Gds Ads Tds Tds Gds Gds Ads mCds Tds Gds mCks mCks Ge | 183 |
| 566248 | 295 | 310 | CTCTGGGATTGGACTG | mCes Tes mCks Tds Gds Gds Gds Ads Tds Tds Gds Gds Ads mCks Tks Ge | 184 |
| 566249 | 298 | 313 | CCACTCTGGGATTGGA | mCes mCes Aks mCds Tds mCds Tds Gds Gds Gds Ads Tds Tds Gks Gks Ae | 185 |
| 566250 | 302 | 317 | GCTCCCACTCTGGGAT | Ges mCes Tks mCds mCds mCds Ads mCds Tds mCds Tds Gds Gds Gks Aks Te | 186 |
| 566251 | 319 | 334 | TGAGTAGGCCAATGGG | Tes Ges Aks Gds Tds Ads Gds Gds mCds mCds Ads Ads Tds Gks Gks Ge | 187 |
| 566252 | 322 | 337 | GAGTGAGTAGGCCAAT | Ges Aes Gks Tds Gds Ads Gds Tds Ads Gds Gds mCds mCds Aks Aks Te | 188 |
| 566253 | 325 | 340 | GCAGAGTGAGTAGGCC | Ges mCes Aks Gds Ads Gds Tds Gds Ads Gds Tds Ads Gds Gks mCks mCe | 189 |
| 566254 | 343 | 358 | GAGGCCAGGACTTGGC | Ges Aes Gks Gds mCds mCds Ads Gds Gds Ads mCds Tds Tds Gks Gks mCe | 190 |
| 566255 | 353 | 368 | AAGTTCAGCAGAGGCC | Aes Aes Gks Tds Tds mCds Ads Gds mCds Ads Gds Ads Gds Gks mCks mCe | 191 |
| 566256 | 356 | 371 | AACAAGTTCAGCAGAG | Aes Aes mCks Ads Ads Gds Tds Tds mCds Ads Gds mCds Ads Gks Aks Ge | 192 |

TABLE 24-continued

Antisense oligonucleotides targeted targeted to SEQ ID NO: 202
(GENBANK Accession number NT_039207.7 truncated from 105809967 to 105810417).

| ISIS No | Start Site | Stop Site | Sequence | Chemistry Notation | SEQ ID NO |
|---|---|---|---|---|---|
| 566257 | 365 | 380 | AGATGTGGAAACAAGT | Aes Ges Aks Tds Gds Tds Gds Gds Ads Ads Ads mCds Ads Aks Gks Te | 193 |
| 566258 | 387 | 402 | ATTCTAATTTCCTTCG | Aes Tes Tks mCds Tds Ads Ads Tds Tds Tds mCds mCds Tds Tks mCks Ge | 194 |
| 566259 | 392 | 407 | CATCTATTCTAATTTC | mCes Aes Tks mCds Tds Ads Tds Tds mCds Tds Ads Ads Tds Tks Tks mCe | 195 |
| 566260 | 395 | 410 | CCCCATCTATTCTAAT | mCes mCes mCks mCds Ads Tds mCds Tds Ads Tds Tds mCds Tds Aks Aks Te | 196 |
| 566261 | 398 | 413 | TGTCCCCATCTATTCT | Tes Ges Tks mCds mCds mCds mCds Ads Tds mCds Tds Ads Tds Tks mCks Te | 197 |
| 566262 | 401 | 416 | AGGTGTCCCCATCTAT | Aes Ges Gks Tds Gds Tds mCds mCds mCds mCds Ads Tds mCds Tks Aks Te | 198 |
| 566263 | 404 | 419 | TGGAGGTGTCCCCATC | Tes Ges Gks Ads Gds Gds Tds Gds Tds mCds mCds mCds mCds Aks Tks mCe | 199 |
| 566264 | 410 | 425 | CACACATGGAGGTGTC | mCes Aes mCks Ads mCds Ads Tds Gds Gds Ads Gds Gds Tds Gks Tks mCe | 200 |
| 566265 | 432 | 447 | GAGTCAACAGAAATAC | Ges Aes Gks Tds mCds Ads Ads mCds Ads Gds Ads Ads Ads Tks Aks mCe | 201 |

---

What is claimed is:

1. A method of inhibiting MMP9 gene expression in a mammalian cell comprising contacting the mammalian cell with a single-stranded antisense compound consisting of the sequence of SEQ ID NO: 3, wherein the antisense compound comprises:
   a gap segment consisting of linked deoxynucleosides;
   a 5' wing segment consisting of linked nucleosides; and
   a 3' wing segment consisting of linked nucleosides;
   wherein the gap segment is positioned between the 5' wing segment and the 3' wing segment, wherein each nucleoside of each wing segment comprises a modified sugar, wherein the antisense compound targets an enhancer RNA (eRNA) transcribed from a genomic enhancer sequence or region, wherein the eRNA is an MMP9 eRNA sequence comprising the nucleic acid sequence of SEQ ID NO: 1, thereby inhibiting expression of the MMP9 gene in the mammalian cell.

2. The method of claim 1, wherein the eRNA transcription is initiated from a RNA polymerase II (PolII) binding site and is capable of elongating bidirectionally.

3. The method of claim 2, wherein the eRNA is capable of enhancing transcription of the MMP9 gene.

4. The method of claim 3, wherein the genomic enhancer sequence or region has a higher level of monomethylated lysine 4 of histone 3 (H3K4me1) than trimethylated lysine 4 of histone 3 (H3K4me3).

5. The method of claim 3, wherein the genomic enhancer sequence or region is enriched for bound RNA polymerase II (PolII).

6. The method of claim 3, wherein the genomic enhancer sequence or region is enriched for bound Rev-Erbα or Rev-Erbβ.

7. The method of claim 1, wherein the transcriptional start site of the MMP9 gene is located on a chromosome at least about 1 kilobase (kb) from the genomic enhancer sequence or region.

8. The method of claim 1, wherein the mammalian cell is a hematopoietic cell, a monocyte, a macrophage, a neuron, a breast cell, or a cancer cell.

9. The method of claim 8, wherein the mammalian cell contacted with the antisense compound is in a subject.

10. A compound comprising a single-stranded antisense compound consisting of the sequence of SEQ ID NO: 3, wherein the antisense compound comprises:
   a gap segment consisting of linked deoxynucleosides;
   a 5' wing segment consisting of linked nucleosides; and
   a 3' wing segment consisting of linked nucleosides;
   wherein the gap segment is positioned between the 5' wing segment and the 3' wing segment, wherein each nucleoside of each wing segment comprises a modified sugar, targeting an enhancer RNA (eRNA) transcribed from a genomic enhancer sequence or region, wherein the eRNA is an MMP9 eRNA sequence comprising the nucleic acid sequence of SEQ ID NO:1.

\* \* \* \* \*

UNITED STATES PATENT AND TRADEMARK OFFICE
CERTIFICATE OF CORRECTION

| | | |
|---|---|---|
| PATENT NO. | : 9,518,261 B2 | Page 1 of 1 |
| APPLICATION NO. | : 14/403103 | |
| DATED | : December 6, 2016 | |
| INVENTOR(S) | : Susan M. Freier et al. | |

It is certified that error appears in the above-identified patent and that said Letters Patent is hereby corrected as shown below:

In the Specification

Column 1, Line 13, before "SEQUENCE LISTING", insert:

--STATEMENT AS TO FEDERALLY SPONSORED RESEARCH

This invention was made with Government support under Grant No. CA52599, DK091183, DK062434, and DK039949, awarded by the National Institutes of Health, and Grant No. W81XWH-08-01-0665 and W81XWH-12-1-0015, awarded by the ARMY/MRMC. The Government has certain rights in the invention.--

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*